US008747321B2

(12) United States Patent
Sankar

(10) Patent No.: US 8,747,321 B2
(45) Date of Patent: Jun. 10, 2014

(54) STRUCTURED RANDOM PERMUTATION PULSE COMPRESSION SYSTEMS AND METHODS

(71) Applicant: Pat Sankar, Tustin, CA (US)

(72) Inventor: Pat Sankar, Tustin, CA (US)

(73) Assignee: Scidea Research, Inc., Tustin, CA (US)

( * ) Notice: Subject to any disclaimer, the term of this patent is extended or adjusted under 35 U.S.C. 154(b) by 0 days.

(21) Appl. No.: 13/657,736

(22) Filed: Oct. 22, 2012

(65) Prior Publication Data
US 2014/0114191 A1 Apr. 24, 2014

Related U.S. Application Data

(60) Provisional application No. 61/683,613, filed on Aug. 15, 2012.

(51) Int. Cl.
A61B 8/14 (2006.01)
G01N 29/34 (2006.01)
H03K 7/00 (2006.01)
H03C 1/00 (2006.01)
H03C 7/00 (2006.01)
H03C 99/00 (2006.01)

(52) U.S. Cl.
CPC  A61B 8/14 (2013.01); G01N 29/34 (2013.01); G01N 29/346 (2013.01); H03K 7/00 (2013.01); H03C 1/00 (2013.01); H03C 7/00 (2013.01); H03C 99/00 (2013.01)
USPC .......................................... 600/443; 600/437

(58) Field of Classification Search
None
See application file for complete search history.

(56) References Cited

U.S. PATENT DOCUMENTS

| 2,939,017 | A | | 5/1960 | Teague, Jr. et al. |
| 4,318,019 | A | | 3/1982 | Teasley et al. |
| 4,851,848 | A | | 7/1989 | Wehner |
| 4,973,967 | A | | 11/1990 | David et al. |
| 5,315,159 | A | | 5/1994 | Gribnau |
| 5,387,918 | A | | 2/1995 | Wiesbeck et al. |
| 5,719,579 | A | | 2/1998 | Torre et al. |
| 5,808,580 | A | | 9/1998 | Andrews, Jr. |
| 5,963,042 | A | * | 10/1999 | Suyama et al. ............... 324/637 |
| 6,188,147 | B1 | | 2/2001 | Hazelton et al. |
| 7,042,109 | B2 | | 5/2006 | Gabrys |
| 7,358,624 | B2 | | 4/2008 | Bacon |

(Continued)

FOREIGN PATENT DOCUMENTS

RU       2367068 C1    9/2009

OTHER PUBLICATIONS

Rao et al., Medical ultrasound imaging using pulse compression, Electronic Letters vol. 29, No. 8, Apr. 1993, pp. 649-651.*

(Continued)

Primary Examiner — Long V. Le
Assistant Examiner — Bradley Impink
(74) Attorney, Agent, or Firm — Knobbe, Martens, Olson & Bear LLP

(57) ABSTRACT

A structured randomly permutated pulse compression system comprises an FM transmitter configured to receive an input signal and transmit an output signal. The FM transmitter is configured to modulate the frequency of the output signal by modulating the frequency of the output signal according to a structured random permutation of time samples of the input signal. At least one antenna interfaces with the FM transmitter. The FM receiver is configured to auto-correlate the output signal with a return signal.

20 Claims, 60 Drawing Sheets

(56) References Cited

U.S. PATENT DOCUMENTS

| | | |
|---|---|---|
| 7,425,772 B2 | 9/2008 | Novo Vidal |
| 7,652,389 B2 | 1/2010 | Farmer |
| 7,679,210 B2 | 3/2010 | Zhu |
| 7,715,166 B2 | 5/2010 | Schultz et al. |
| 7,841,982 B2 | 11/2010 | Johnson et al. |
| 8,009,001 B1 | 8/2011 | Cleveland |
| 8,035,551 B1 | 10/2011 | Govoni |
| 8,049,663 B2 | 11/2011 | Frank et al. |
| 8,264,314 B2 | 9/2012 | Sankar |
| 2005/0135190 A1* | 6/2005 | Katou et al. ............ 367/99 |
| 2008/0013245 A1 | 1/2008 | Schultz et al. |
| 2008/0074223 A1 | 3/2008 | Pribonic |
| 2008/0084071 A1 | 4/2008 | Zhu |
| 2008/0231052 A1 | 9/2008 | Farmer |
| 2008/0315709 A1 | 12/2008 | Uchiyama |
| 2010/0133853 A1 | 6/2010 | Masi et al. |
| 2011/0031760 A1 | 2/2011 | Lugg |
| 2011/0241349 A1 | 10/2011 | Sankar |
| 2011/0267924 A1* | 11/2011 | Horsky et al. ............ 367/99 |
| 2012/0209113 A1 | 8/2012 | Sankar |

OTHER PUBLICATIONS

Misaridis et al., Use of modulated excitation signals in medical ultrasound. Part I: basic concepts and expected benefits, IEEE Transactions on Ultrasonics, Ferroelectrics, and Frequency Control, vol. 52, No. 2, Feb. 2005, pp. 177-191.*

Misaridis et al., Use of modulated excitation signals in medical ultrasound. Part II: design and performance for medical imaging applications, IEEE Transactions on Ultrasonics, Ferroelectrics, and Frequency Control, vol. 52, No. 2, Feb. 2005, pp. 192-207.*

Misaridis et al., Use of modulated excitation signals in medical ultrasound. Part III: high frame rate imaging, IEEE Transactions on Ultrasonics, Ferroelectrics, and Frequency Control, vol. 52, No. 2, Feb. 2005, pp. 208-219.*

International Search Report mailed by the Russian Patent Office on Nov. 21, 2013 in the corresponding PCT Application No. PCT/US2013/054725 (7 pages).

U.S. Appl. No. 13/607,595, including its prosecution history, the cited references, and then Office Actions therein, Not yet published, Sankar.

U.S. Appl. No. 13/674,869, including its prosecution history, the cited references, and the Office Actions therein, Not yet published, Sankar.

U.S. Appl. No. 13/657,664, including its prosecution history, the cited references, and the Office Actions therein, Not yet published, Sankar.

Doerry, Armin W. "Generating Nonlinear FM Chrip Waveforms for Radar," Sandia National Laboratories, 34 pages, Sep. 2006.

* cited by examiner

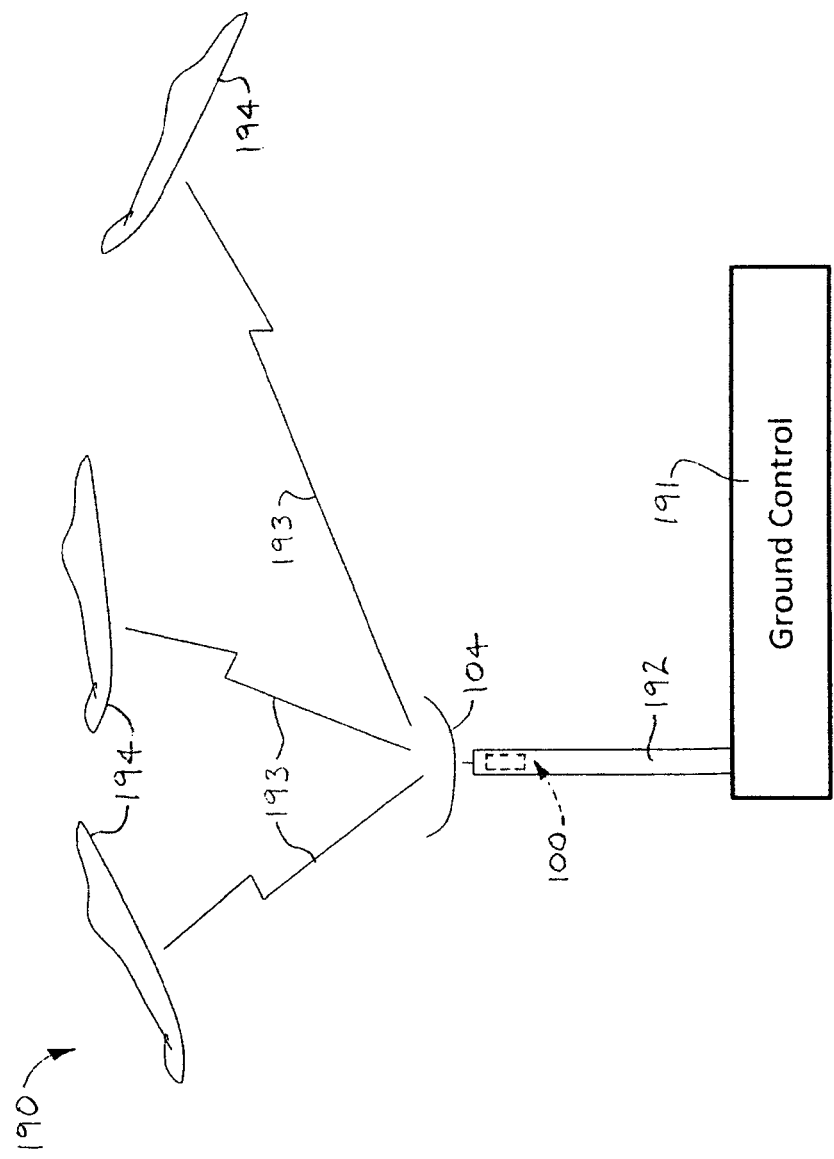

Cross Ambiguity of
Rectangular Pulse
(Threshold 0.5 Max Value)

Cross Ambiguity of
Rectangular Pulse

Cross Ambiguity of
LFM Pulse
(Threshold 0.5 Max Value)

Cross Ambiguity of
LFM Pulse

Cross Ambiguity of
Barker Pulse
(Threshold 0.5 Max Value)

Cross Ambiguity of
Barker Pulse

Cross Ambiguity of
PRN Pulse
(Threshold 0.5 Max Value)

Cross Ambiguity of PRN
Pulse

Cross Ambiguity of
SP1 Pulse
(Threshold 0.5 Max Value)

Cross Ambiguity of
SP1 Pulse

Cross Ambiguity of
SP2 Pulse
(Threshold 0.5 Max Value)

Cross Ambiguity of
SP2 Pulse

Cross Ambiguity of
SP3 Pulse
(Threshold 0.5 Max Value)

Cross Ambiguity of
SP3 Pulse

Cross Ambiguity of
SP4 Pulse
(Threshold 0.5 Max Value)

Cross Ambiguity of
SP4 Pulse

Cross Ambiguity of
SP5 Pulse
(Threshold 0.5 Max Value)

Cross Ambiguity of
SP5 Pulse

Cross Ambiguity of
SP6 Pulse
(Threshold 0.5 Max Value)

Cross Ambiguity of
SP6 Pulse

Cross Ambiguity of
SP7 Pulse
(Threshold 0.5 Max Value)

Cross Ambiguity of
SP7 Pulse

Cross Ambiguity of
SP8 Pulse
(Threshold 0.5 Max Value)

Cross Ambiguity of
SP8 Pulse

Cross Ambiguity of Rectangular Pulse (Threshold 0.5 Max Value)

Cross Ambiguity of Rectangular Pulse

Cross Ambiguity of
LFM Pulse

Cross Ambiguity of
LFM Pulse
(Threshold 0.5 Max Value)

Cross Ambiguity of
NLFM Pulse
(Threshold 0.5 Max Value)

Cross Ambiguity of
NLFM Pulse

Cross Ambiguity of
Barker Pulse
(Threshold 0.5 Max Value)

Cross Ambiguity of
Barker Pulse

Cross Ambiguity of
PRN Pulse
(Threshold 0.5 Max Value)

Cross Ambiguity of PRN
Pulse

Cross Ambiguity of
SP1 Pulse
(Threshold 0.5 Max Value)

Cross Ambiguity of
SP1 Pulse

Cross Ambiguity of
SP3 Pulse
(Threshold 0.5 Max Value)

Cross Ambiguity of
SP3 Pulse

Cross Ambiguity of
SP4 Pulse
(Threshold 0.5 Max Value)

Cross Ambiguity of
SP4 Pulse

Cross Ambiguity of
SP5 Pulse
(Threshold 0.5 Max Value)

Cross Ambiguity of
SP5 Pulse

Cross Ambiguity of
SP6 Pulse
(Threshold 0.5 Max Value)

Cross Ambiguity of
SP6 Pulse

Cross Ambiguity of
SP7 Pulse
(Threshold 0.5 Max Value)

Cross Ambiguity of
SP7 Pulse

Cross Ambiguity of
SP8 Pulse
(Threshold 0.5 Max Value)

Cross Ambiguity of
SP8 Pulse

STRUCTURED RANDOM PERMUTATION PULSE COMPRESSION SYSTEMS AND METHODS

CROSS-REFERENCES TO RELATED APPLICATIONS

The present application claims the benefit of U.S. Provisional Application No. 61/683,613, filed Aug. 15, 2012, the entire disclosure of which is hereby incorporated herein by reference in its entirety.

BACKGROUND

1. Field

The disclosure relates to high resolution RADAR, LIDAR and other applications. More particularly, the disclosure relates to a non-linear FM pulse compression system and method which enhances target resolution in RADAR, LIDAR and other applications.

2. Description

The word RADAR is an acronym derived from the phrase RAdio Detection And Ranging and applies to electronic equipment designed for detecting and tracking objects (targets) at considerable distances. The basic principle behind radar is simple—extremely short bursts of radio energy (traveling at the speed of light) are transmitted, reflected off a target and then returned as an echo. The RADAR system correlates the return signal (appropriately corrected for gain) with the transmitted pulse to indicate the location of the target within a two or three dimensional framework. Among the various radar processing techniques, pulse compression is a signal processing technique mainly used not only in radar but also in sonar and echography to enhance the range resolution as well as the signal-to-noise ratio.

The rectangular pulse of an electromagnetic signal is given by [1]

$$P_r(t) = A\exp(-j2\pi f_c t) \quad T/2 \le t < T \quad (1)$$

where $f_c$ is the carrier frequency.

The linear FM chirp of an RF signal is given by $$P_{FM}(t) = A\exp(-j2\pi f_c t^2) \quad T/2 \le t < T \quad (2)$$

Various techniques for pulse compression of electromagnetic signals using variants of frequency modulation are known in the art. These include an AM-FM laser for improved accuracy of target range measurements and a LASER RADAR system which uses an optically linear modulated FM chirp signal (also known as a compressed high intensity radar pulse). Another method proposes a random FM scheme for mobile radios including a non-linear FM modulation which is carried out by driving an FM modulator with random or chaotic sequences and deriving theoretical expressions for the spectral properties of the FM waveforms.

The conventional FM chirp techniques mentioned above either use linear FM modulation or propose the use of random input sequences to create non-linear FM signals with the perfect auto correlation function properties. However, these techniques are either too complicated to implement in many applications or do not result in optimal pulse compression. Moreover, conventional pulse compression techniques may not result in a range resolution which is optimal for the application. Therefore, a non-linear FM pulse compression system and method which can result in an order of magnitude improvement in pulse compression and hence dramatically improve the resolution as well as the precision of range of detected targets in RADAR, LADAR and other applications is needed.

SUMMARY

The disclosure is generally directed to a non-linear FM pulse compression system. This application relates to U.S. application Ser. No. 12/804,379, titled "Pulse Compression System and Method" and filed on Jul. 19, 2010, the entire contents of which are incorporated herein by reference. An illustrative embodiment of the system includes a non-linear FM transmitter adapted to receive an input signal and transmit an output signal. The non-linear FM transmitter is adapted to modulate a frequency of the output signal by at least one of the following: increasing the frequency of the output signal as a logarithmic function of the frequency of samples in the input signal; modulating the frequency of the output signal in an inversely proportional relationship to the frequency of samples in the input signal; and modulating the frequency of the output signal according to a random permutation of the frequency of the input signal. At least one antenna interfaces with the non-linear FM transmitter. The non-linear FM receiver is adapted to auto-correlate the output signal with a return signal.

The disclosure is further generally directed to a non-linear FM pulse compression method. An illustrative embodiment of the method includes providing an input signal; forming an output signal by modulating the frequency of the input signal by at least one of the following: increasing the frequency of the output signal as a logarithmic function of the frequency of samples in the input signal; modulating the frequency of the output signal in an inversely proportional relationship to the frequency of samples in the input signal; and modulating the frequency of the output signal according to a random permutation of the frequency of the input signal; transmitting the output signal against a target; receiving a return signal from the target; and auto-correlating the output signal with the return signal.

The disclosure is further generally directed to a free electron laser system. An illustrative embodiment of the free electron laser system includes an undulator having a pair of spaced-apart parallel series of magnets having alternating poles; a laser cavity defined between the spaced apart parallel series of magnets; and an electron source adapted to emit an electron beam through the laser cavity.

In some embodiments, a structured randomly permutated pulse compression generating system comprises: an FM transmitter configured to receive an input signal and transmit an output signal, wherein the FM transmitter is configured to modulate a frequency of the input signal according to a structured random permutation of time samples of the input signal; at least one antenna interfacing with the FM transmitter; and an FM receiver interfacing with the at least one antenna, wherein the FM receiver is configured to auto-correlate the output signal with a return signal. In certain embodiments, the system above further comprises a display interfacing with the FM receiver and the at least one antenna. The system above can further comprise a synchronizer interfacing with the FM transmitter and the display. In certain embodiments, the input signal in the system above is a linear frequency modulation (LFM) signal. In certain embodiments, the input signal in the system above is a rectangular pulse. In certain embodiments, the input signal above is a barker code modulating a rectangular pulse. In certain embodiments, the input signal above is a pseudo random number code modulating a rectangular pulse. In certain embodiments, the input signal in the system above is a non-linear frequency modulation signal.

In some embodiments, a radar system comprises: at least one antenna; a transmitter configured to be connected to the at least one antenna, the transmitter configured to generate an output signal by modulating an input signal according to a structured random permutation pulse compression method, the transmitter further configured to transmit the output signal through the at least one antenna; a receiver configured to be connected to the at least one antenna, the receiver configured to receive a return signal through the at least one antenna; a data processor configured to communicate with the receiver, the data processor configured to correlate the return signal with the output signal; an image generator configured to communicate with the data processor, the image generator configured to generate an image based on the correlation of the return signal with the output signal; and a display configured to communicate with the image generator, the display configured to display the generated image. In certain embodiments, the radar system above is a bistatic system such that the at least one antenna comprises a first antenna and a second antenna, wherein the transmitter is connected to the first antenna and the receiver is connected to the second antenna. In certain embodiments, the radar system above is a monostatic system such that the transmitter and the receiver are connected to a single antenna, and the radar system further comprises a duplexer configured to connect the transmitter and the receiver to the single antenna. In certain embodiments, the input signal in the radar system above is a linear frequency modulation (LFM) signal. In certain embodiments, the input signal in the radar system above is a rectangular pulse. In certain embodiments, the input signal in the radar system above is a barker code modulating a rectangular pulse. In certain embodiments, the input signal in the radar system above is a pseudo random number code (PRN) modulating a rectangular pulse. In certain embodiments, the input signal in the radar system above is a non-linear frequency modulation signal. In certain embodiments, the correlation of the return signal with the output signal is an image signal, and the image generator is further configured to generate an image using only image signal values above a threshold value.

In some embodiments, a radar system comprises: at least one antenna; a transmitter configured to be connected to the at least one antenna, the transmitter configured to generate an output signal by modulating an input signal according to a structured random permutation pulse compression method, the transmitter further configured to transmit the output signal through the at least one antenna; a receiver configured to be connected to the at least one antenna, the receiver configured to receive a return signal through the at least one antenna, the receiver further configured to correlate the return signal with the output signal; an image generator configured to generate an image based on the correlation of the return signal with the output signal; and a display configured to display the generated image to a user. In certain embodiments, the radar system above is a bistatic system such that the at least one antenna comprises a first antenna and a second antenna, wherein the transmitter is connected to the first antenna and the receiver is connected to the second antenna. In certain embodiments, the radar system above is a monostatic system such that the transmitter and the receiver are connected to a single antenna, and the radar system further comprises a duplexer configured to connect the transmitter and the receiver to the single antenna. In certain embodiments, the input signal in the radar system above is a linear frequency modulation (LFM) signal. In certain embodiments, the input signal in the radar system above is a rectangular pulse. In certain embodiments, the input signal in the radar system above is a barker code modulating a rectangular pulse. In certain embodiments, the input signal in the radar system above is a pseudo random number code (PRN) modulating a rectangular pulse. In certain embodiments, the input signal in the radar system above is a non-linear frequency modulation signal. In certain embodiments, the correlation of the return signal with the output signal is an image signal, and the image generator is further configured to generate an image using only image signal values above a threshold value.

In some embodiments, a radar system comprises: at least one antenna; a transmitter configured to be connected to the at least one antenna, the transmitter configured to generate an output signal by modulating an input signal according to a structured random permutation pulse compression method, the transmitter further configured to transmit the output signal through the at least one antenna; a receiver configured to communicate with the at least one antenna, the receiver configured to receive a return signal through the at least one antenna and correlate the return signal with the output signal to generate a display signal; and a display configured to receive and display the display signal. In certain embodiments, the radar system above is a bistatic system such that the at least one antenna comprises a first antenna and a second antenna, wherein the transmitter is connected to the first antenna and the receiver is connected to the second antenna. In certain embodiments, the radar system above is a monostatic system such that the transmitter and the receiver are connected to a single antenna, and the radar system further comprises a duplexer configured to connect the transmitter and the receiver to the single antenna. In certain embodiments, the input signal in the radar system above is a linear frequency modulation (LFM) signal. In certain embodiments, the input signal in the radar system above is a rectangular pulse. In certain embodiments, the input signal in the radar system above is a barker code modulating a rectangular pulse. In certain embodiments, the input signal in the radar system above is a pseudo random number code (PRN) modulating a rectangular pulse. In certain embodiments, the input signal in the radar system above is a non-linear frequency modulation signal. In certain embodiments, the display is further configured to display only image signal values above a threshold value.

In some embodiments, an ultrasound-based diagnostic medical imaging system comprises: at least one transducer, the transducer configured to be placed adjacent a tissue surface, the transducer comprising a piezoelectric crystal configured to produce ultrasound waves for transmission into the tissue surface, the transducer further comprising a scanner configured to receive reflected ultrasound waves reflected off structures below the tissue surface; a modulator configured to be connected to the piezoelectric crystal, the modulator configured to generate an output signal by modulating an input signal according to a structured random permutation pulse compression method, the modulator further configured to transmit the output signal through the piezoelectric crystal; a data processing module configured to be connected to the scanner, the data processing module configured to receive the reflected ultrasound waves through the scanner, the data processing module further configured to correlate the reflected sound waves with the produced ultrasound waves; an image generator configured to generate an image based on the correlation of the reflected sound waves with the produced ultrasound waves; and a display configured to display the generated image to a user. In certain embodiments, the input signal in the ultrasound-based diagnostic medical imaging system above is a linear frequency modulation (LFM) signal. In certain embodiments, the input signal in the ultrasound-based diagnostic medical imaging system above is a rectangular pulse. In certain embodiments, the input signal in the ultrasound-based diagnostic medical imaging system above is a barker code modulating a rectangular pulse. In certain embodiments, the input signal in the ultrasound-based diagnostic medical imaging system above is a pseudo random number code modulating a rectangular pulse. In certain embodiments, the input signal in the ultrasound-based diagnostic medical imaging system above is a non-linear frequency modulation signal.

In some embodiments, an active sonar system comprises a transmitter configured to generate an output acoustic signal by modulating an input signal according to a structured random permutation pulse compression method, the transmitter further configured to transmit the output acoustic signal into a body of water. The active sonar system can also include: a scanner configured to receive a reflected acoustic signal from an object in the body of water; a data processing module configured to be connected to the scanner, the data processing module configured to receive the reflected acoustic signal through the receiver and to correlate the reflected acoustic signal with the output acoustic signal; an image generator configured to generate an image based on the correlation of the reflected acoustic signal with the output acoustic signal; and a display configured to display the generated image to a user. In certain embodiments, the input signal in the active sonar system can be a linear frequency modulation (LFM) signal. In certain embodiments, the input signal in the active sonar system can be a rectangular pulse. In certain embodiments, the input signal in the active sonar system can be a barker code modulating a rectangular pulse. In certain embodiments, the input signal in the active sonar system can be a pseudo random number code modulating a rectangular pulse. In certain embodiments, the input signal in the active sonar system can be a non-linear frequency modulation signal.

BRIEF DESCRIPTION OF THE DRAWINGS

The disclosure will now be made, by way of example, with reference to the accompanying drawings, in which:

FIG. 19 is a schematic diagram which illustrates implementation of an illustrative embodiment of the non-linear FM pulse compression system in a high resolution air traffic control system application;

DETAILED DESCRIPTION OF THE PREFERRED EMBODIMENT

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

The disclosure is generally directed to an FM pulse compression system and method and in some embodiments to a non-linear FM pulse compression system. Some embodiments may include non-linear mapping of the time sequence which in a randomly frequency modulated signal. Some embodiments may accomplish the same result by random permutation of the carrier pulse signal.

In some embodiments, the frequency of the output non-linear FM chirp signal increases as a logarithmic function of the frequency of the samples in the input signal and is given by (referred to as SP1):

$$P_{LogFM}(t) = A\exp(-j2\pi f_c \log_2(t)) \quad T/2 \le t < T/2 \quad (3)$$

In some embodiments, the frequency changes in the non-linear FM chirp signal are inversely proportional to the frequency of the samples in the input pulse signal and are given by (referred to as SP2):

$$P_{InvFM}(t)=A\exp(-j2\pi f_c/t) \quad T/2 \leq t < T/2 \quad (4)$$

In some embodiments, the frequency changes of the non-linear FM chirp signal are produced by a random permutation of the input pulse signal to create a random sinusoid (referred to as SP3):

$$P_{RandomFM}(t)=\text{Random Permutation}\{A\exp(-j2\pi f_c/t)\}$$
$$T/2 \leq t < T/2 \quad (5a)$$

In some embodiments, the random permutation may be performed on the input to the sinusoid rather than the output (also referred to as SP3):

$$P_{RandomFM}(t)=A\exp(\text{Random Permutation}\{-j2\pi f_c/t\})$$
$$T/2 \leq t < T/2 \quad (5b)$$

For some applications, however, performing the random permutation on the output of the sinusoidal pulse may be simpler.

Figure 1:
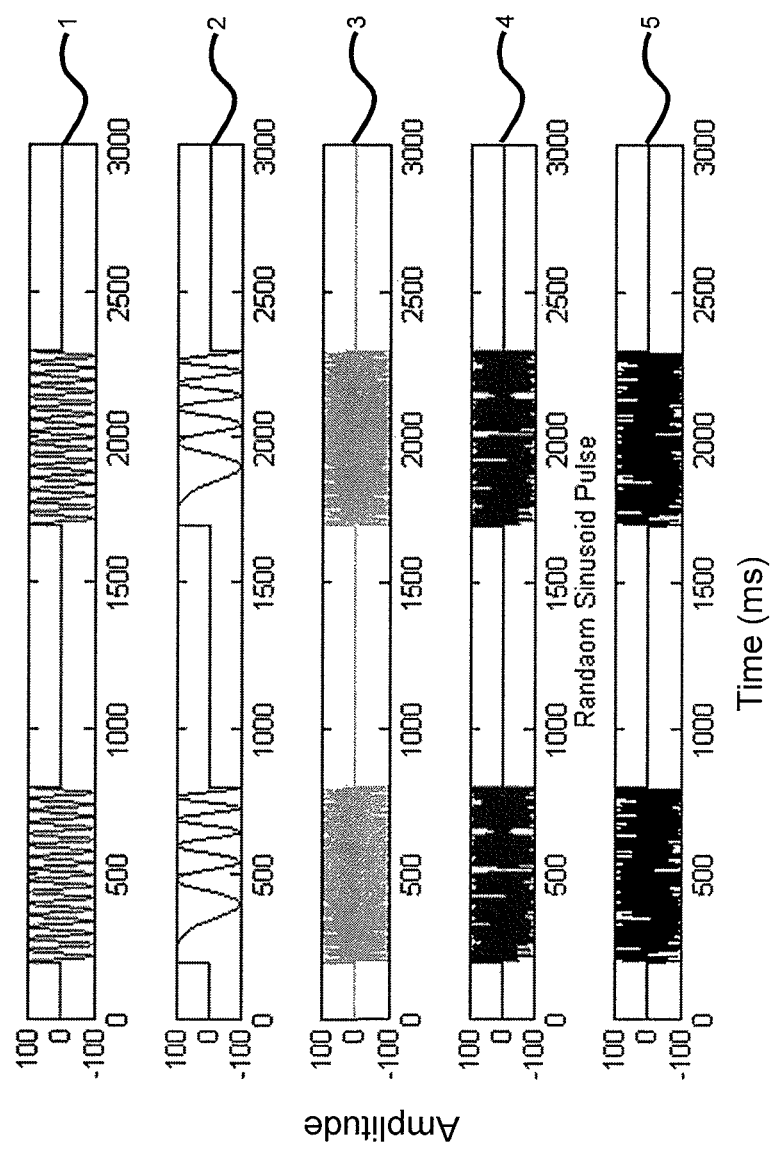
FIG. 1 is a graph which illustrates various types of pulse waveforms.
Figure 3:
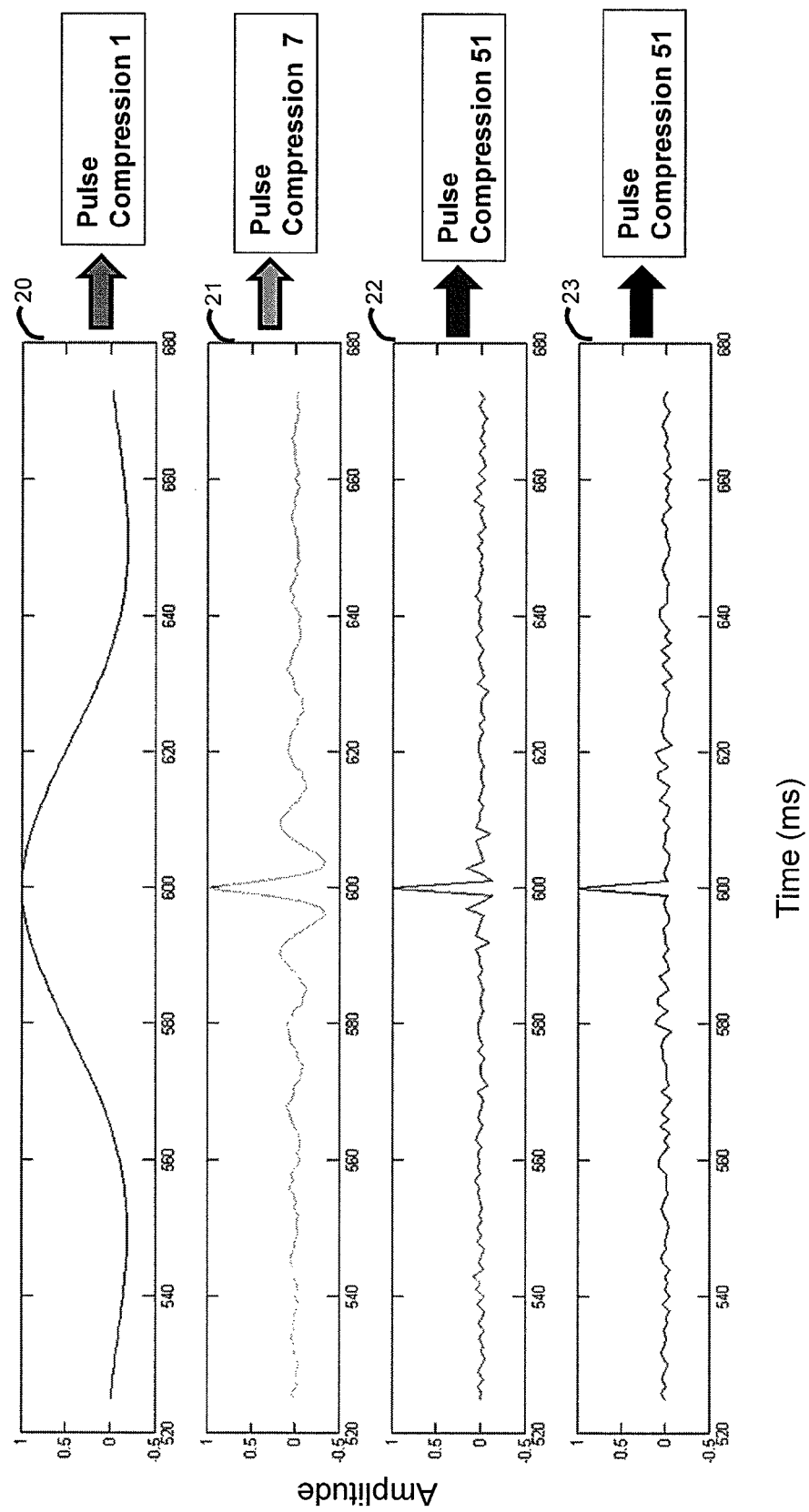
FIG. 3 is a graph which illustrates autocorrelation functions of the pulse waveforms illustrated in FIG. 1 with pulse compression factors.

Referring initially to FIG. 1 of the drawings, a graph which illustrates various types of pulse waveforms is illustrated. The graph includes a square pulse waveform 1, a linear FM pulse waveform 2, a non-linear log FM pulse waveform 3, a non-linear inverse pulse waveform 4 and a non-linear random sinusoid FM pulse waveform 5. The non-linear log FM pulse waveform 3, the non-linear inverse pulse waveform 4 and the non-linear random sinusoid FM pulse waveform 5 have a near-random appearance, which is the fundamental reason why the auto correlation functions of the signals 21-23 which correspond to these waveforms almost resemble a delta function as shown in FIG. 3, whereas the auto correlation function of the signal which corresponds to the linear waveform 20 does not.

Figure 2:
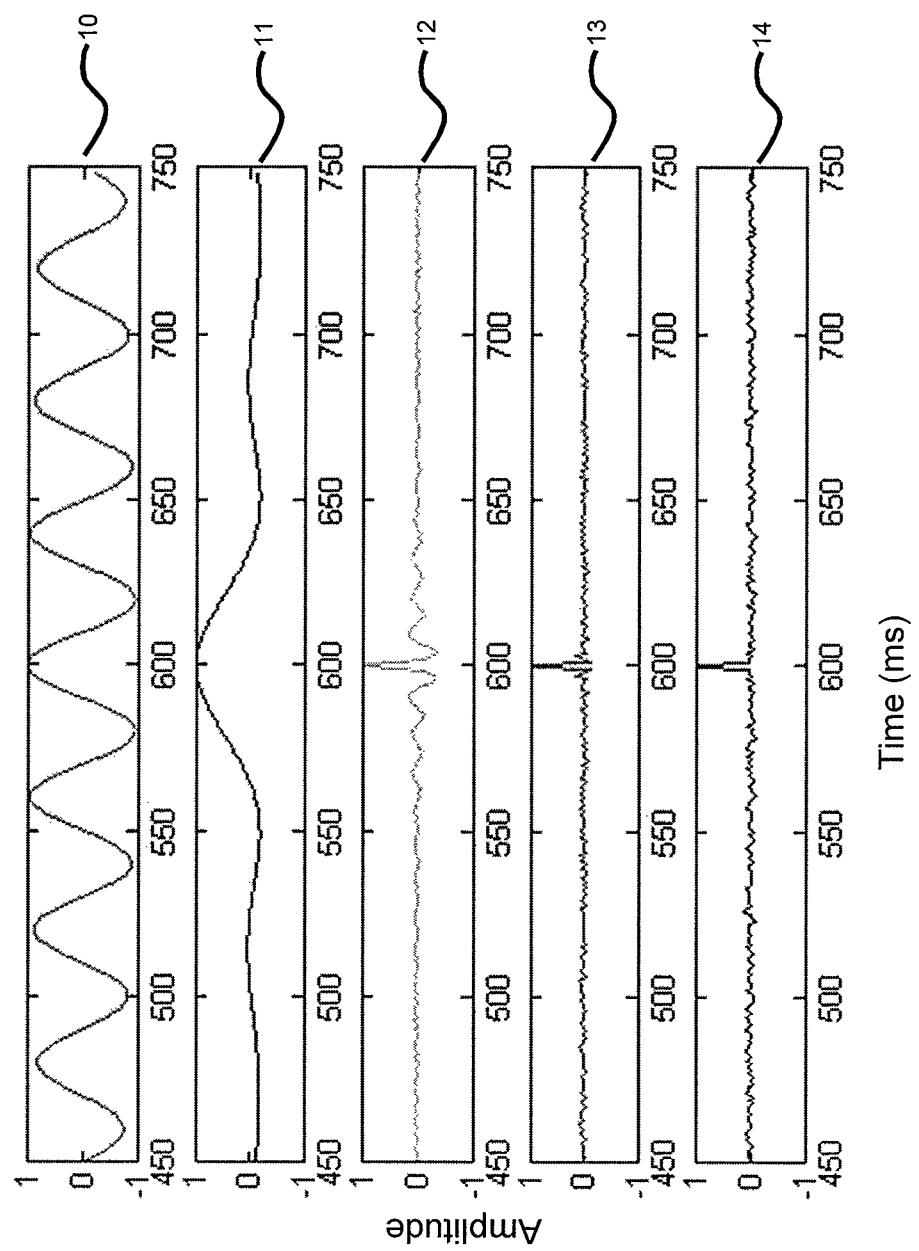
FIG. 2 is a graph which illustrates autocorrelation functions of the pulse waveforms illustrated in FIG. 1.

Referring next to FIG. 2 of the drawings, a graph is illustrated which shows autocorrelation functions of the pulse waveforms illustrated in FIG. 1. Reference numerals 10-14 respectively illustrate autocorrelation functions of the square pulse waveform 1, the linear FM pulse waveform 2, the non-linear log FM pulse waveform 3, the non-linear inverse FM pulse 4 and the non-linear random sinusoidal FM pulse 5 of FIG. 1. When the auto correlation functions 11-14 in FIG. 2 are compared, it is apparent that the auto correlation signal corresponding to the inverse FM chirp pulse 13 and the random sinusoidal chirp pulse 14 most resemble the delta function, a desired property for the optimally-compressed pulse. FIG. 3 illustrates the auto correlation functions of the various non-linear chirp signals 20-23, respectively, with the corresponding pulse compression factors.

Figure 5:
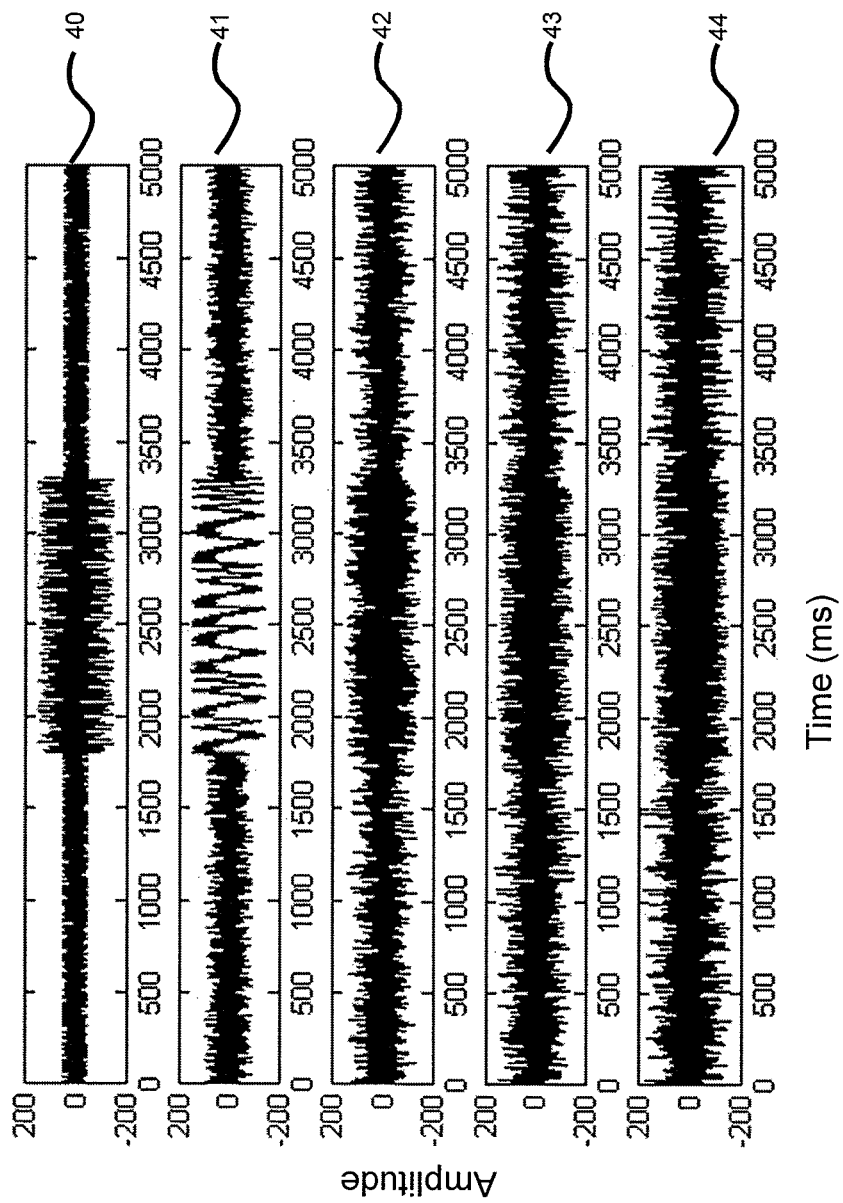
FIG. 5 is a graph which illustrates automatic gain control (AGC) corrected return echo signals for the pulse waveforms illustrated in FIG. 1.
Figure 6:
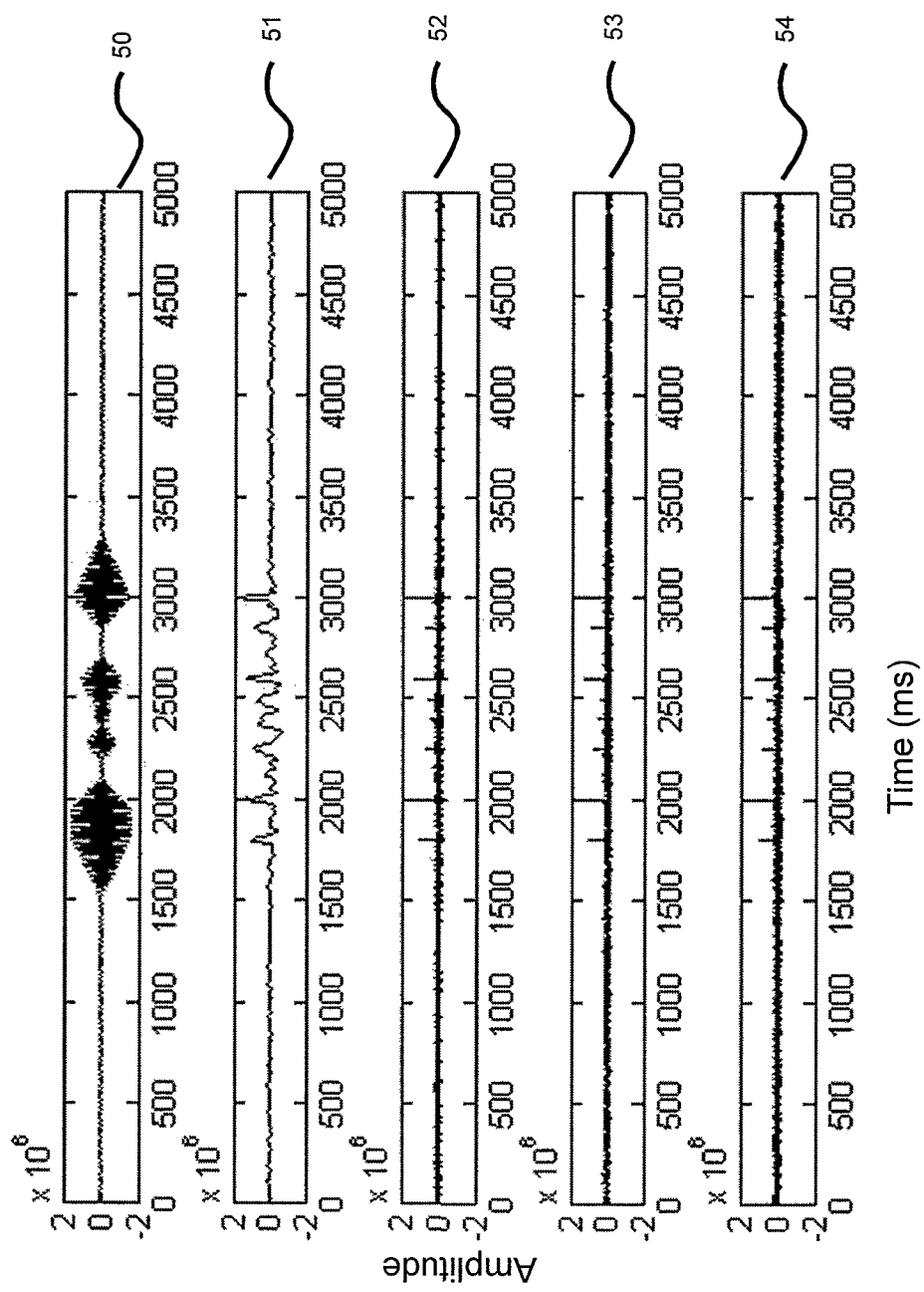
FIG. 6 is a graph which illustrates matched filter outputs for the pulse waveforms illustrated in FIG. 1.

It is possible to infer from FIG. 5 that the auto correlation function of the non-linear log FM pulse 42 and the non-linear inverse FM pulse 43 are compressed versions of the auto correlation functions of the linear square pulse 40 and linear FM pulse 41. If the compression ratio between the two sinc functions is 4*T/fc where T is the pulse width in terms of the number of samples in the pulse, and fc is the base frequency of the FM modulation of the pulse, the plot of the theoretical and computed compression factors versus the various values of fc are shown in FIG. 6 and also in Table 1.

TABLE I

| Carrier Frequency | Theoretical Pulse Compression Factor | Pulse Compression Factor Log FM | Pulse Compression Factor Inverse FM | Pulse Compression Factor Random FM |
|---|---|---|---|---|
| 25 | 96 | 15.86 | 55.5 | 111 |
| 50 | 48 | 14.57 | 51 | 51 |
| 100 | 24 | 12.5 | 25 | 25 |
| 200 | 12 | 4 | 8 | 8 |

TABLE I-continued

| Carrier Frequency | Theoretical Pulse Compression Factor | Pulse Compression Factor Log FM | Pulse Compression Factor Inverse FM | Pulse Compression Factor Random FM |
|---|---|---|---|---|
| 400 | 6 | 3 | 6 | 6 |
| 800 | 3 | 3 | 3 | 3 |

The analytical expression for the auto correlation of the linear FM modulated signal 41 (FIG. 5) is given by the following equation [5]:

$$\langle s_{c'}, s_{c'}\rangle(t) = T\Lambda\left(\frac{t}{T}\right)\text{sinc}\left[\pi\Delta ft\Lambda\left(\frac{t}{T}\right)\right]e^{2i\pi f_0 t} \quad (5)$$

where T is the width of the pulse, and $\Lambda(t/T)$ is the triangle weighting function.

The maximum of the autocorrelation function of $S_{c'}$ is reached at zero. Around zero, this function behaves as the sinc term. The −3 dB temporal width of that cardinal sine is approximately equal $$T' = \frac{1}{\Delta f}.$$

Everything happens as if, after matched filtering, the resolution that would have been reached with a simple pulse of duration T' is obtained. For the common values of $\Delta f$, t' is smaller than T, hence the pulse compression name.

Figure 4:
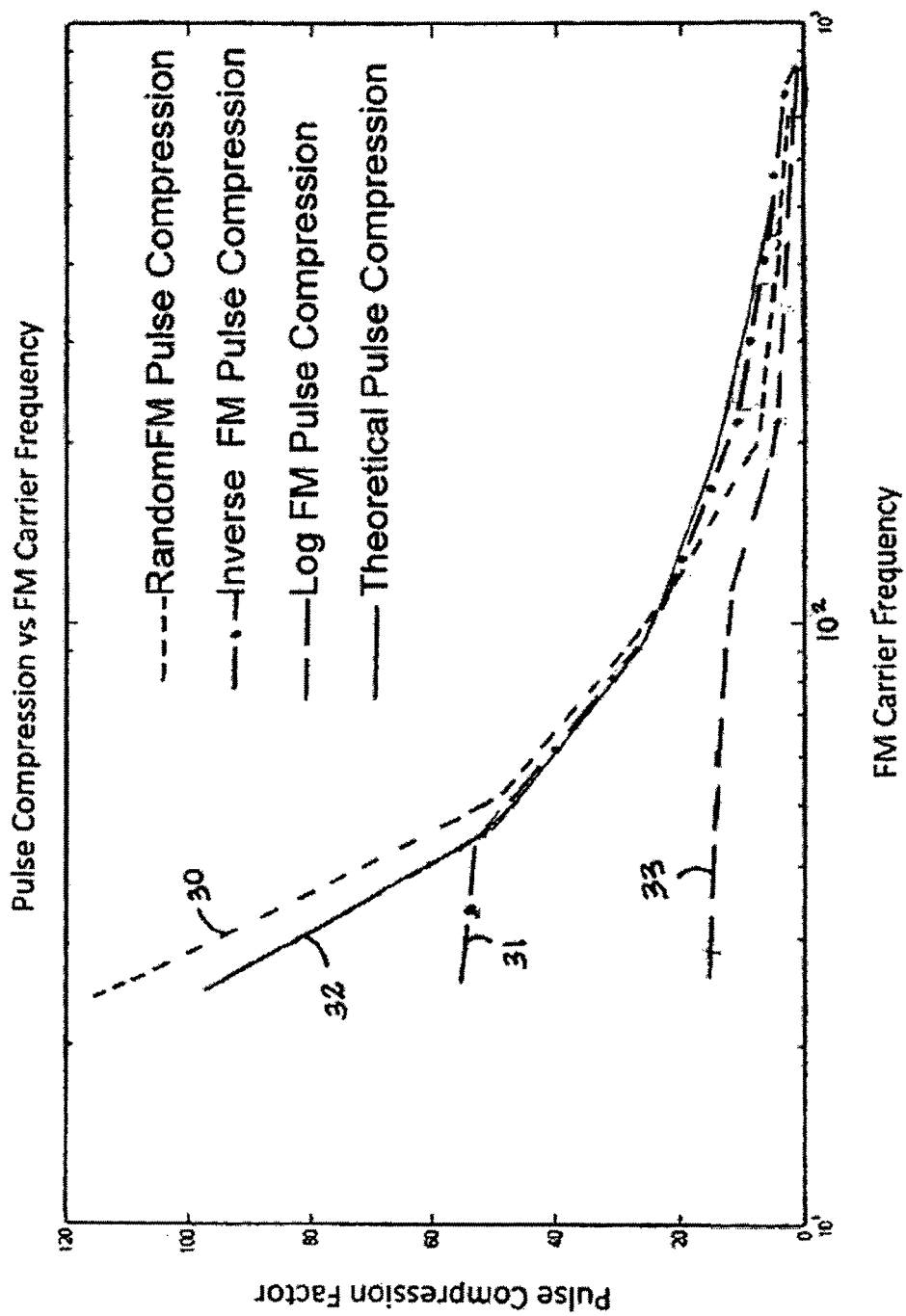
FIG. 4 is a line graph which illustrates theoretical estimates and computed pulse compression factors (y-axis) for non-linear FM signals for various values of the carrier frequency (x-axis)

Even though it cannot be rigorously proven, based on the comparisons of FIG. 3 and the non-linear vs. linear FM modulation of the random FM pulse compression the inverse FM pulse compression 31, the log FM pulse compression 32 and the theoretical pulse compression 33, as illustrated in FIG. 4, the autocorrelation function of the non-linear FM modulated signal is very similar to that of the linear FM modulated signal but with a width of the main lobe further compressed as shown below:

$$T_{nfm}=T_{fm}/(M/f_c) \quad (6)$$

where M is the number of samples in the pulse and $f_c$ is the base frequency of the linear FM modulator and $T_{fm}=T'$.

Since energy is conserved for all three types of pulse waveforms $$P_r T_r = P_{fm} T_{fm} = P_{nfm} T_{nfm}$$

where $P_r$, $T_r$, $P_{fm}$, $T_{fm}$, $P_{nfm}$ and $T_{nfm}$ are the power required and the main lobe half width of the rectangular pulse, linear FM modulated pulse and the nonlinear modulated FM pulse. Hence, the power required to transmit the non-linear FM modulated signal is given by $$P_{nfm}=P_{fm}(T_{fm}/T_{nfm})=P_r(T_r/T_{nfm}) \quad (8)$$

The Radar range equation states that if τ is the time of travel of the pulse echo from the target, then the range r from the target is given by:

$$R=(c\tau)/2 \quad (9)$$

where c is the speed of light given by $3\times10^8$ m/s.

As an example, a radar experiment may include four targets closely separated by distances 270, 300, 337.5, 360, 373.5, 390.0, 427.5 and 450 meters, respectively. Assuming a sampling rate of 1 Giga Hertz, the echo locations of these targets will be approximately 1800, 2000, 2250, 2400, 2490, 2600, 2850 and 3000, respectively.

In FIG. 5, the automatic gain control of corrected return signals in the presence of 0 dB background noise for all five types of pulse waveforms 40-44, respectively, is illustrated. The targets are buried in the return echo RF signal.

In FIG. 6, the automatic gain matched filter output in the presence of 0 dB background noise for all the five types of pulse waveforms 50-54, respectively, is illustrated. A careful examination clearly demonstrates the advantages of the linear FM signal 51 over the rectangular pulse 50 and the higher resolution provided by the non-linear FM modulated signals 52, 53, 54 over the linear FM signal.

Figure 7:
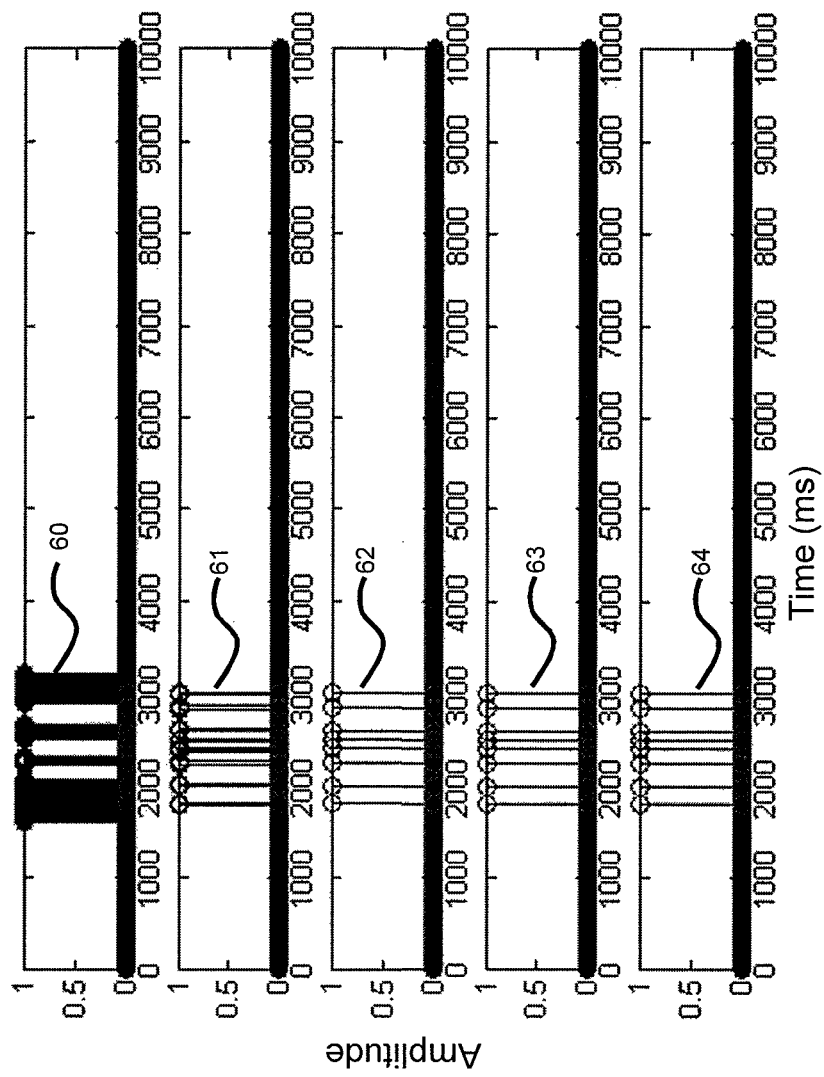
FIG. 7 is a graph which illustrates detected targets for the pulse waveforms illustrated in FIG. 1.
Figure 8:
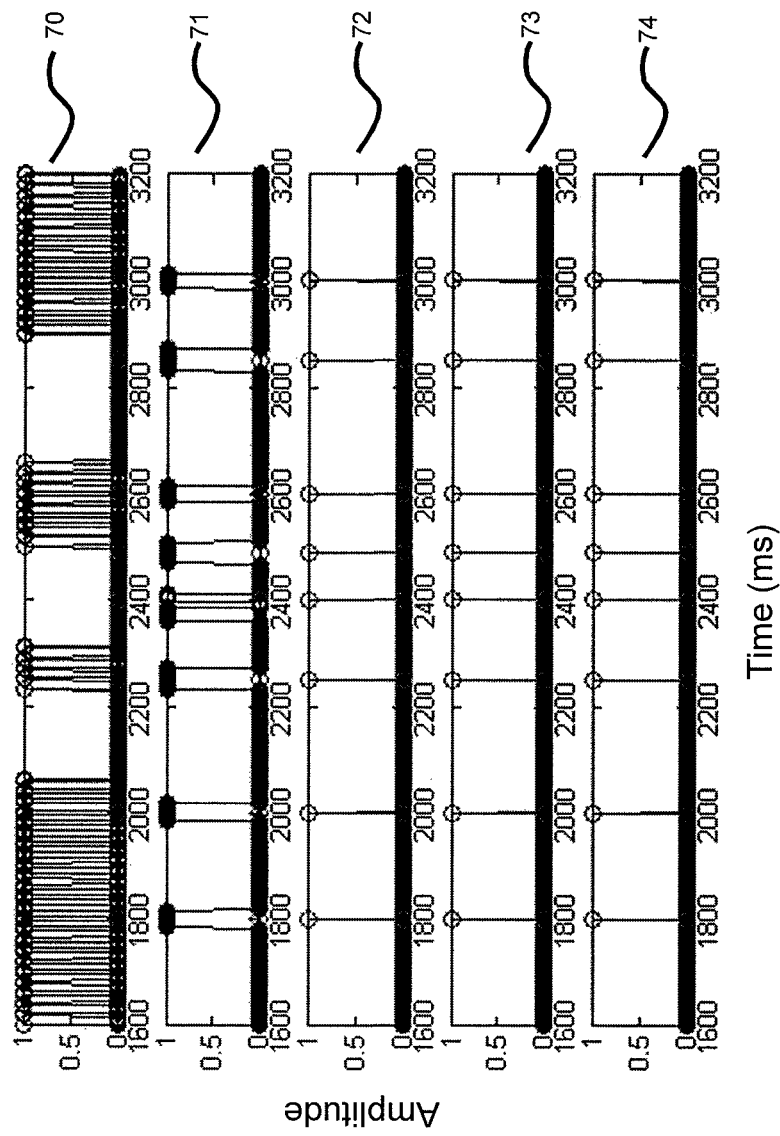
FIG. 8 is a close-up view of the detected targets for the pulse waveforms illustrated in FIG. 1.

In FIG. 7, the detected targets for each of the five signals 60-64, respectively, and a closeup of the same 70-74, respectively, are illustrated in FIG. 8. It is more clear from FIGS. 7 and 8 that the non-linear FM pulses (62-64, respectively, in FIG. 7 and 72-74, respectively, in FIG. 8) provide the highest resolution in addition to improved accuracy for the targets over the rectangular pulse 60, 70 and the linear FM pulse 61, 71.

If a continuous pulse waveform is transmitted at a base frequency of $f_c$ and the measured frequency of the received pulse is $f_t$, then the Doppler shift $f_d$ in frequency is defined by $$f_t = f_c f_d \text{ for approaching targets} \tag{10}$$

$$f_t = f_c - f_d \text{ for receding targets} \tag{11}$$

Radar Doppler shift frequency is a function of radar transmit frequency ($f_t$) speed of wave (c=speed of light), and target velocity ($v_t$). Note, $v_t$ is positive (+) for approaching targets and negative (−) for receding targets:

$$f_d = \pm 2 v_t f_o / c \tag{12}$$

$$v_t = \pm c f_d / 2 f_o \tag{13}$$

It is also possible to use a CW radar system to measure range instead of range rate by frequency modulation, the systematic variation of the transmitted frequency. What this does in effect is to put a unique "time stamp" on the transmitted wave at every instant. By measuring the frequency of the return signal, the time delay between transmission and reception can be measured and therefore the range determined as before. Of course, the amount of frequency modulation must be significantly greater than the expected Doppler shift or the results will be affected.

Figure 9:
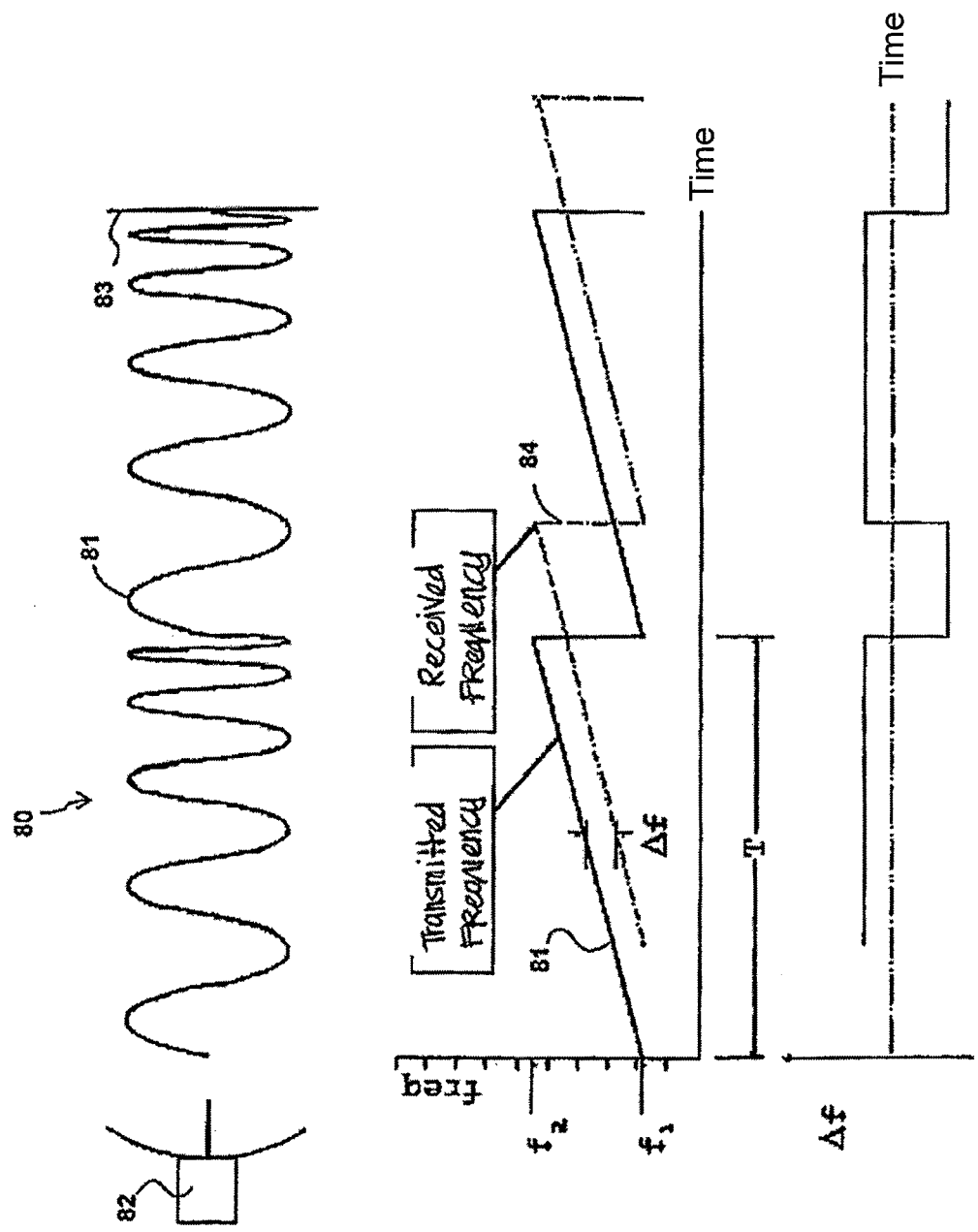
FIG. 9 is a schematic diagram which illustrates theory of operation for frequency modulated continuous wave (FMCW) RADAR.

Referring next to FIG. 9 of the drawings, a schematic diagram which illustrates theory of operation for a frequency modulated continuous wave (FMCW) RADAR system 80 is illustrated. A transmitted frequency 81 is emitted from a transmitter 82. A received frequency 84 is returned from the target 83. The simplest way to modulate the wave is to linearly increase the frequency such that the transmitted frequency 81 will change at a constant rate Δf, as illustrated in FIG. 9.

Figure 10:
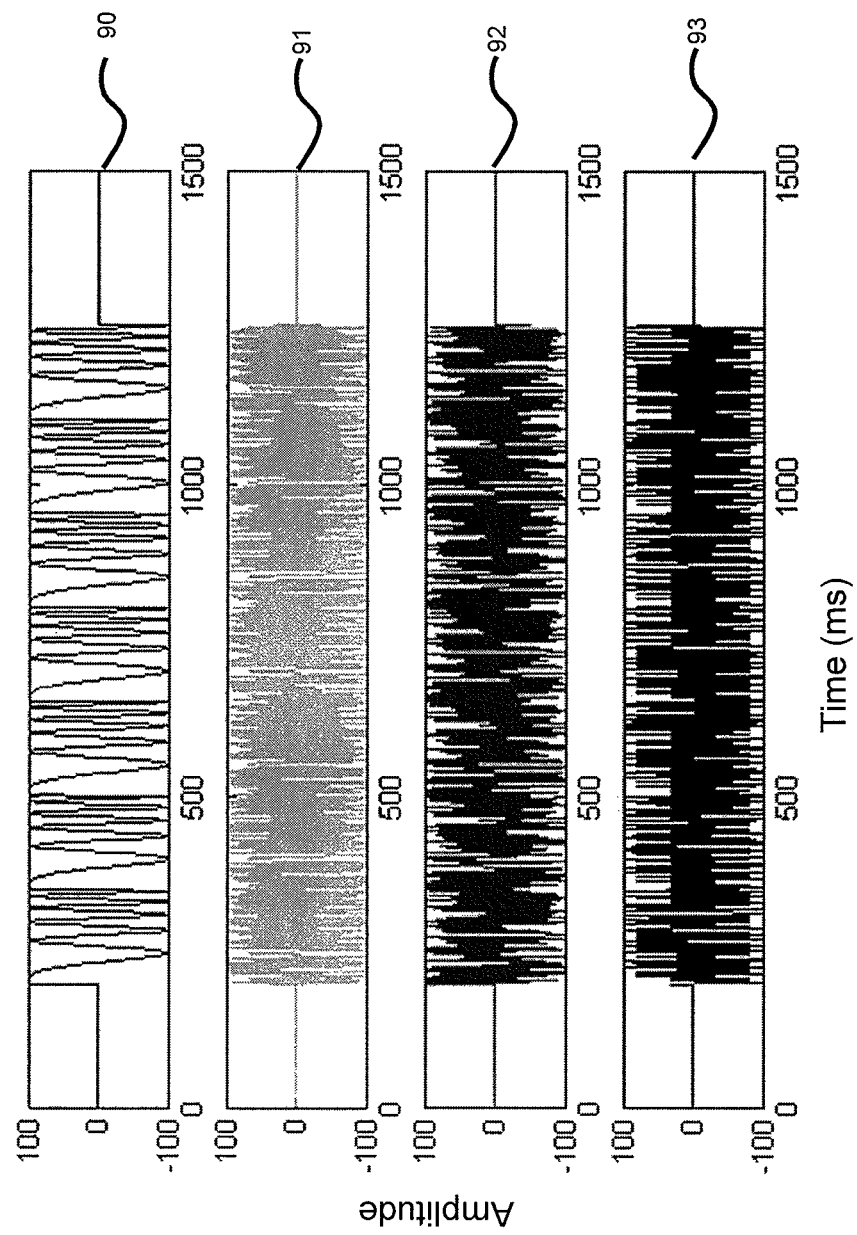
FIG. 10 is a graph which illustrates FMCW RADAR for each of the pulse waveforms illustrated in FIG. 1.

The FMCW RADAR system 80 measures the instantaneous difference between the transmitted frequency 81 and the received frequency 84, Δf. This difference is directly proportional to the time delay, Δt, which is what it takes the radar signal to reach the target 83 and return. From this the range can be found using the usual formula, R=cΔt/2. The time delay can be found as follows:

$$\Delta t = T \Delta f / (f_2 - f_1) \tag{14}$$

where:
$f_2$=maximum frequency.
$f_1$=minimum frequency
T=period of sweep from $f_1$ to $f_2$,
and Δf=the difference between transmitted and received.
Combining these equations into a single form for the range $$R = 2 c t \Delta f / (f_2 - f_1) \tag{15}$$

where Δf is the difference between the transmitted frequency 81 and the received frequency 84 (when both are from the same sweep, i.e. when it is positive). The linear FMCW pulse 90, the log FM FMCW pulse 91, the inverse FM FMCW pulse 92 and the random sinusoid FM FMCW pulse 93 are shown in FIG. 10.

Figure 11:
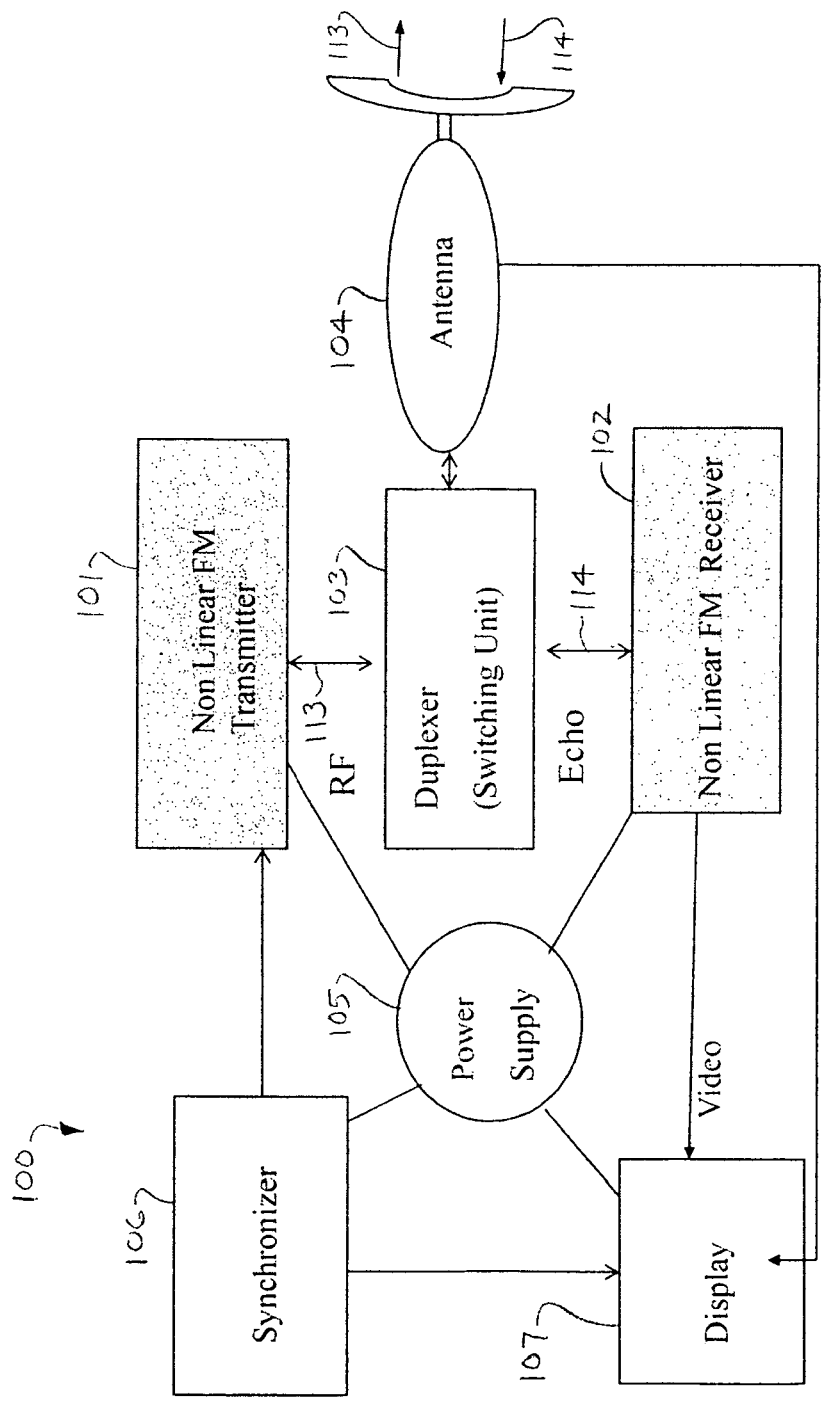
FIG. 11 is a block diagram of an illustrative embodiment of a non-linear FM pulse compression system.

Referring next to FIG. 11 of the drawings, a block diagram 100 of an illustrative embodiment of a non-linear FM pulse compression system (hereinafter "system"), is illustrated. The system 100 may include a non-linear FM transmitter 101 and a non-linear FM receiver 102. A duplexer or switching unit 103 may interface with the non-linear FM transmitter 101 and the non-linear FM receiver 102. An antenna 104 may interface with the duplexer 103. A synchronizer 106 may interface with the non-linear FM transmitter 101. A display 107 may interface with the non-linear FM receiver 102, the antenna 104 and the synchronizer 106. A power supply 105 may be connected to the non-linear FM transmitter 101, the non-linear FM receiver 102, the synchronizer 106 and the display 107.

In some embodiments, the non-linear FM transmitter 101 may be adapted to modulate the frequency of an input pulse signal by increasing the frequency of the input pulse signal as a logarithmic function of the frequency of the samples in the input pulse signal, as expressed by equation (3) above, to generate an output non-linear FM chirp signal 113. In some embodiments, the non-linear FM transmitter 101 may be adapted to modulate the frequency of an input pulse signal such that the frequency changes in the non-linear FM chirp signal 113 are inversely proportional to the frequency of the samples in the input pulse signal as expressed by equation (4) above. In some embodiments, the non-linear FM transmitter 101 may be adapted to modulate the frequency of the sinusoidal input pulse signal such that the non-linear FM chirp signal 113 is a random permutation of the output of the sinusoidal input pulse signal as expressed by equation (5a) above. In some embodiments, the non-linear FM transmitter 101 may be adapted to modulate the frequency of the input pulse signal such that the non-linear FM chirp signal 113 is a random permutation of the input to the sinusoidal input pulse signal as expressed by equation (5b) above.

The non-linear FM transmitter 101 may be adapted to emit the non-linear FM signal 113 to the duplexer 103. Through the duplexer 103, the antenna 104 may be adapted to emit the nonlinear FM chirp signal 113 which is generated by the non-linear FM transmitter 101 to a target (not illustrated). The non-linear FM receiver 102 may be adapted to receive a return signal 114 from the target through the duplexer 103. The synchronizer 106 may ensure that the return signal 114 is reliably interpreted by the non-linear FM receiver 102. The non-linear FM receiver 102 may additionally be adapted to auto-correlate the return signal 114 with the non-linear FM chirp signal 113 which is emitted by the antenna 104. The display 107 may be adapted to receive the auto-correlated return signal from the non-linear FM receiver 102 and display the image of the target which is generated from the auto-correlated return signal.

Figure 13:
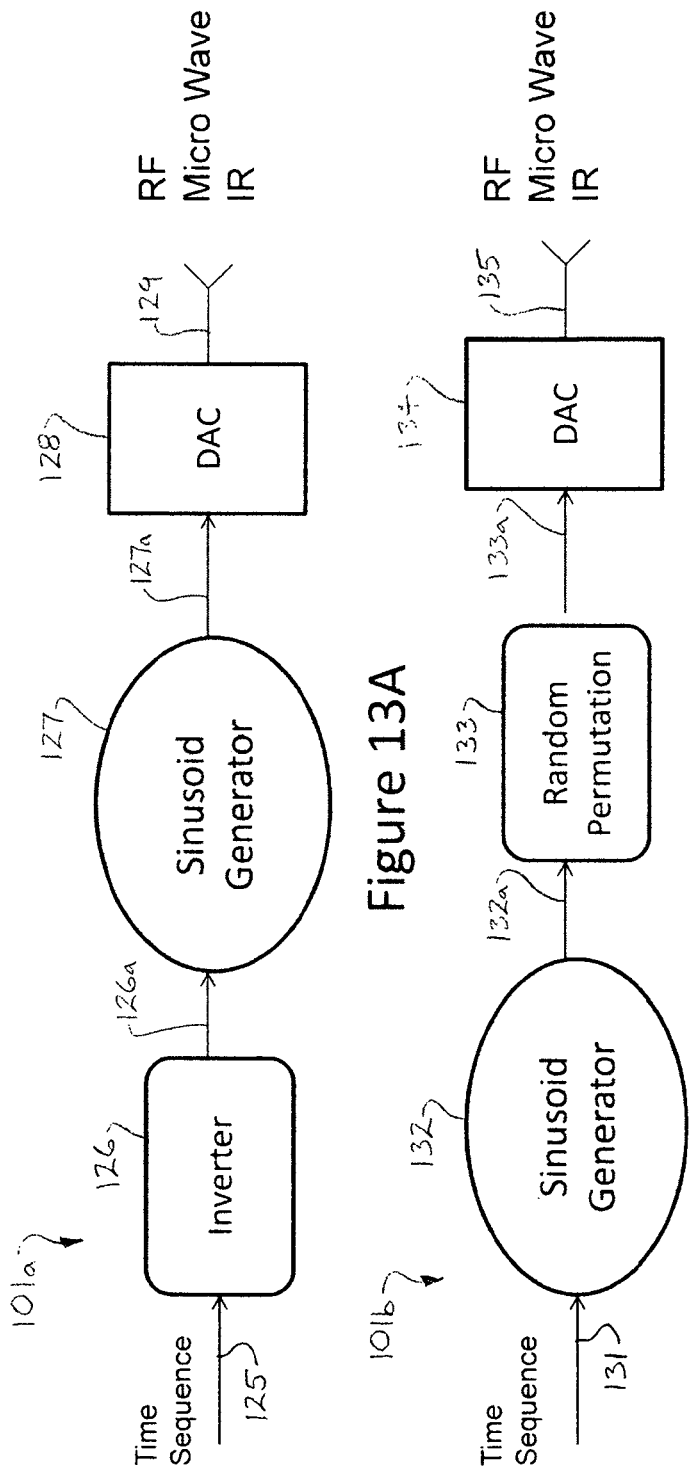
FIG. 13A is a block diagram of an inverse FM modulator pulse generator which is suitable for implementation of an illustrative embodiment of the non-linear FM pulse compression system.
FIG. 13B is a block diagram of a random sinusoid pulse generator which is suitable for implementation of an illustrative embodiment of the non-linear FM pulse compression system.

Referring next to FIG. 13A of the drawings, in some embodiments, the non-linear FM transmitter 101 may include an inverse FM modulator pulse generator 101a. The inverse FM modulator pulse generator 101a may be adapted to modulate the frequency changes in an input pulse signal such that the frequency changes in the output non-linear FM chirp signal are inversely proportional to the frequency of the samples in the input pulse signal as expressed by equation (4) above. The inverse FM modulator pulse generator 101a may include an inverter 126, a sinusoid generator 127 which interfaces with the inverter 126 and a digital to analog converter (DAC) 128 which interfaces with the sinusoid generator 127. An antenna 129 may interface with the DAC 128.

The inverter 126 may be adapted to invert the time sequence 125 of an input pulse signal and emit an inverter output signal 126a having the inverted time sequence. The sinusoid generator 127 may be adapted to receive the inverter output signal 126a from the inverter 126 and generate a sinusoidal pulse 127a having the inverted time sequence. The digital to analog converter (DAC) 128 may be adapted to receive the sinusoidal pulse 127a from the sinusoid generator 127 and convert the sinusoidal pulse 127a from a digital signal to an analog non-linear FM chirp signal. The antenna 129 may be adapted to emit the non-linear FM chirp signal which is received from the DAC 128. Therefore, the frequency changes in the output non-linear FM chirp signal are inversely proportional to the frequency of the samples corresponding to the original time sequence 125 in the input sinusoidal pulse.

Referring next to FIG. 13B of the drawings, in some embodiments, the non-linear FM transmitter 101 may include a random sinusoid pulse generator 101b. The random sinusoid pulse generator 101b may be adapted to produce frequency changes of the non-linear FM chirp signal by a random permutation of the input pulse signal to generate a random sinusoidal nonlinear FM chirp signal as expressed by equation (5a) above. The random sinusoid pulse generator 101b may include a sinusoid generator 132, a random permutation component 133 which interfaces with the sinusoid generator 132, a digital to analog converter (DAC) 134 which interfaces with the random permutation component 133 and an antenna 135 which interfaces with the DAC 134.

The sinusoid generator 132 may be adapted to generate a sinusoidal input pulse signal 132a having a time sequence 131. The random permutation component 133 may be adapted to produce a random permutation of the input sinusoidal pulse signal 132a and transmit a random sinusoidal pulse signal 133a to the DAC 134. The DAC 134 may be adapted to convert the digital random sinusoidal pulse signal 133a into an analog non-linear FM chirp signal which is emitted by the antenna 135.

Figure 12:
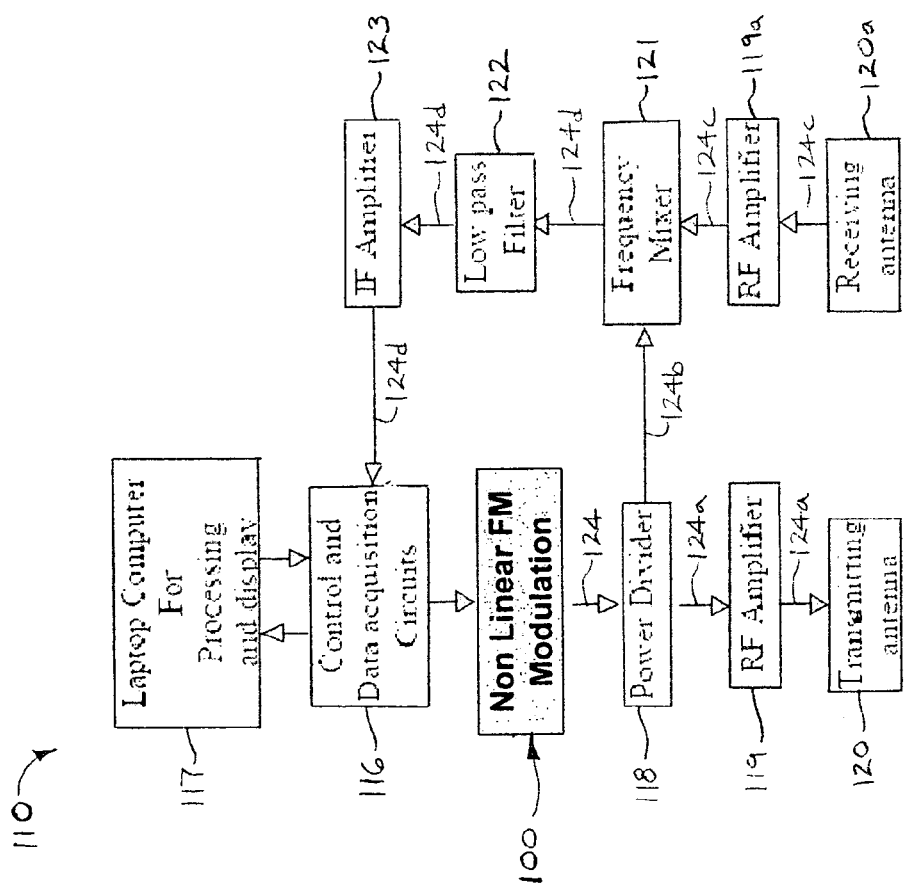
FIG. 12 is a block diagram of an illustrative embodiment of a non-linear FMCW laser.

Referring next to FIG. 12 of the drawings, a block diagram of an illustrative embodiment of a non-linear FM CW laser is generally indicated by reference numeral 110. The non-linear FM CW laser 110 may include a non-linear FM pulse compression system 100. Control and data acquisition circuits 116 may interface with the system 100. A laptop or other computer 117 may interface with the control and data acquisition circuits 116 for data processing and display purposes. A power divider 118 may also interface with the system 100. An RF amplifier 119 may interface with the power divider 118. A transmitting antenna 120 may interface with the RF amplifier 119.

The non-linear FM CW laser 110 may also include a receiving antenna 120a. An RF amplifier 119a may interface with the receiving antenna 120a. A frequency mixer 121 may interface with the RF amplifier 119a and with the power divider 118. A low pass filter 122 may interface with the frequency mixer 121. An IF amplifier 123 may interface with the low pass filter 122. The control and data acquisition circuits 116 may interface with the IF amplifier 123.

In operation of the non-linear FM CW laser 110, the oscillator of the system 100 emits a non-linear frequency-modulated sinusoidal wave signal 124. The power divider 118 divides the signal 124 into a transmitted signal 124a which is received by the RF amplifier 119 and a reference signal 124b which is received by the frequency mixer 121. After the RF amplifier 119 amplifies the transmitted signal 124a, the transmitting antenna 120 transmits the transmitted signal 124a to a target (not illustrated).

The receiving antenna 120a receives the reflected signal 124c from the target. The RF amplifier 119a amplifies the reflected signal 124c, and the frequency mixer 121 receives the amplified reflected signal 124c. At the frequency mixer 121, the reflected signal 124c mixes with the reference signal 124b. A mixed signal 124d, which is a modulated low frequency sinusoidal signal the main frequency of which is equal to the frequency difference between the reference signal 124b and the reflected signal 124c, is obtained from the output of the frequency mixer 121 and passes through the low pass filter 122 and the IF amplifier 123, respectively. At the control and data acquisition circuits 116, the mixed signal 124d is Fourier transformed into a frequency domain. The spectrum which appears on the laptop computer 117 displays all the reflection events and travel time delays between reflection events which can be calculated using the parameters such as the start and stop frequencies of the modulated oscillator of the system 100, the scanning time period and the frequency difference between reflection events.

Figure 14:
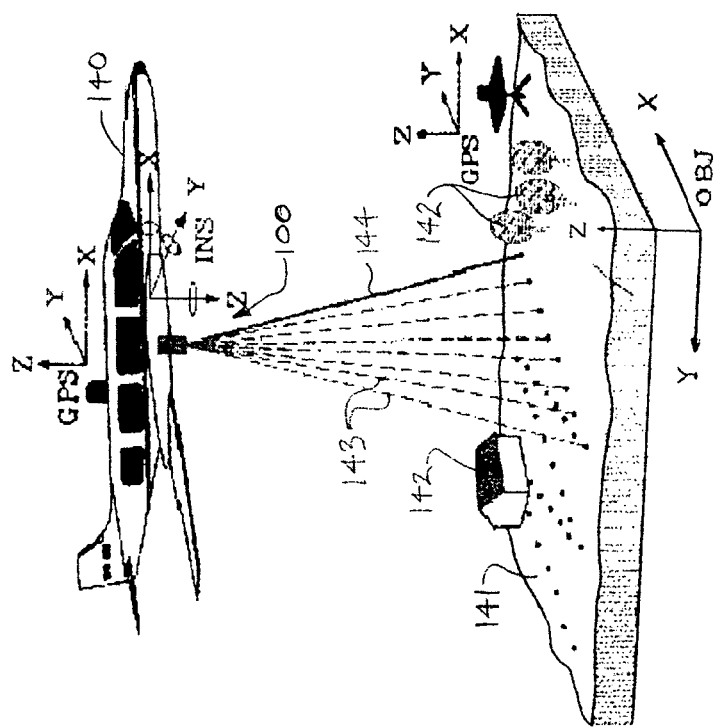
FIG. 14 is a schematic diagram which illustrates implementation of an illustrative embodiment of the non-linear FM pulse compression system in imaging targets on the ground from an aircraft.

Referring to FIG. 14 of the drawings, a schematic diagram which illustrates implementation of an illustrative embodiment of the non-linear FM pulse compression system 100 in imaging targets on the ground 141 from an aircraft 140 via LIDAR (Light Detection And Ranging) is illustrated. LIDAR is an optical remote sensing technology that measures properties of scattered light to find range and/or other information of a distant target. The prevalent method to determine distance to an object 142 or surface 141 is to use laser pulses 143. Like radar technology, which uses radio waves, the range to an object 142 is determined by measuring the time delay between transmission of a pulse 143 and detection of the reflected signal 144.

A recent addition to a police officer's speed detection arsenal is LIDAR (Laser Infrared Detection And Ranging). To measure a vehicle's speed, LIDAR determines how long it takes a light pulse to travel from the LIDAR gun to the vehicle and back. From this information, LIDAR can quickly find the distance between the gun and the vehicle. By making several measurements and comparing the distance the vehicle traveled between measurements, LIDAR very accurately determines the vehicle's speed. LIDAR uses a laser beam of invisible infrared light. The beam reflects off any flat surface on the vehicle. Since the beam is very narrow, it is impossible for any laser detector to determine the distance between the LIDAR source and the vehicle.

Just as there are two types of RADAR, there are also two types of lasers: Pulsed Lasers and Continuous Wave (CW) Lasers, which are used in LIDAR applications. The present disclosure includes use of the non-linear FM pulse compression system 100 for use in ranging and Doppler measurement applications.

Figure 15:
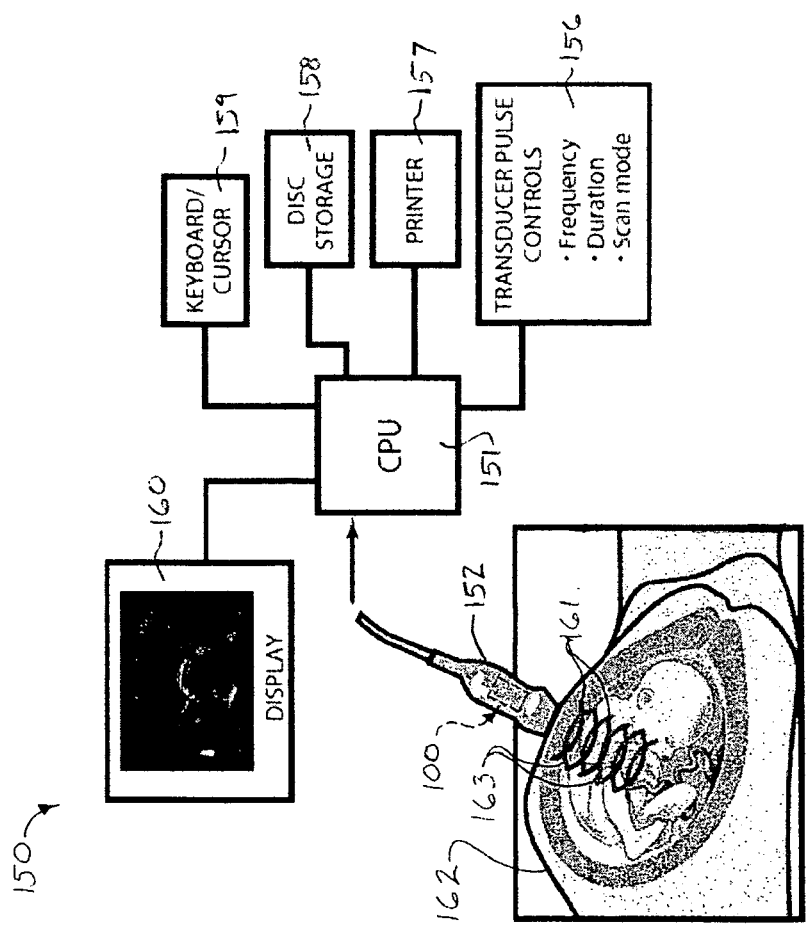
FIG. 15 is a schematic diagram which illustrates implementation of an illustrative embodiment of the non-linear FM pulse compression system in an ultrasonic imaging application.

Referring next to FIG. 15 of the drawings, a high-resolution medical ultrasound system 150 which utilizes an illustrative embodiment of the pulse compression system 100 is illustrated. The system 150 may include an ultrasound transducer 152 into which the pulse compression system 100 is installed. A CPU 151 may interface with the ultrasound transducer 152. External devices may interface with the CPU 151. The external devices may include transducer pulse controls 156, a printer 157, a disc storage device 158, a keyboard/cursor 159 and a display 160, for example and without limitation.

The pulse compression system 100 in the ultrasound transducer 152 transmits high frequency sound pulses 161 into a patient's body 162. The sound pulses 161 travel through the patient's body 162, passing through different types of tissue. Although the average speed of sound through human tissues is 1540 m/s, it does vary with exact tissue type. While the speed of sound through fat is 1459 m/s, it passes through bone at 4080 m/s. When sound encounters two adjacent tissue types with different acoustic properties, a proportion of the sound energy is reflected as reflected sound pulses 163. These boundaries between different tissue types are called acoustic interfaces.

The amount of reflected sound pulses 163 reflected back from an acoustic interface depends on a property of the materials on either side of the interface called acoustic impedance. The acoustic impedance of a material is simply the density of the material multiplied by the speed at which sound travels through the material.

Figure 16:
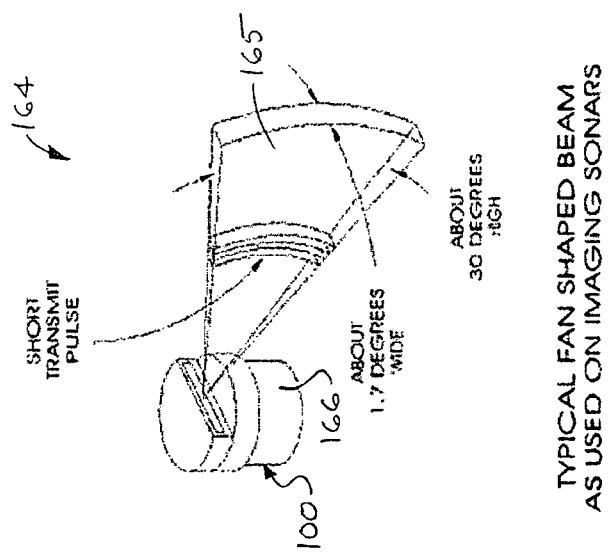
FIG. 16 is a schematic diagram which illustrates implementation of an illustrative embodiment of the non-linear FM pulse compression system in a high resolution sonar application.

Referring next to FIG. 16 of the drawings, a high resolution sonar system 164 which utilizes an illustrative embodiment of the pulse compression system 100 is illustrated. The pulse compression system 100 of the high resolution sonar system 164 can be used to power and drive the sonar beam generators 166 of the pulse compression system 100 to emit a sonar pulse 165 which may have a fan shape, as illustrated. The high resolution sonar system 164 uses sound propagation (usually underwater, as in submarine navigation) to navigate, communicate with or detect other vessels. There are two types of technology which share the name "sonar": passive sonar is essentially listening for the sound made by vessels; active sonar is emitting pulses of sounds and listening for echoes. Sonar may be used as a means of acoustic location and of measurement of the echo characteristics of "targets" in the water. Acoustic location in air was used before the introduction of radar.

Figure 17:
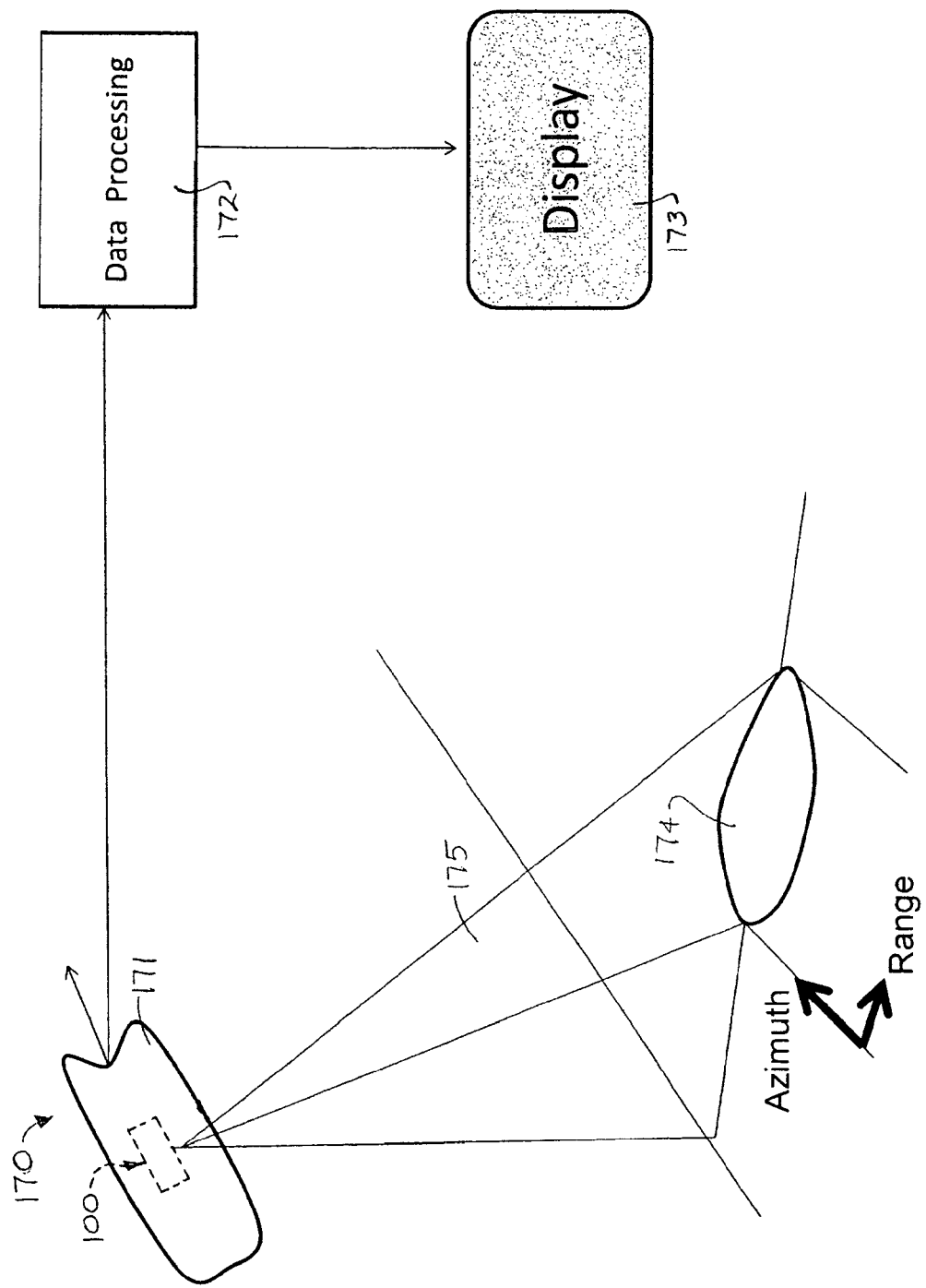
FIG. 17 is a schematic diagram which illustrates implementation of an illustrative embodiment of the non-linear FM pulse compression system in a high resolution synthetic aperture application.

Referring next to FIG. 17 of the drawings, a high resolution synthetic radar system 170 which utilizes an illustrative embodiment of the pulse compression system 100 is illustrated. The pulse compression system 100 may be provided in a spacecraft 171 and emits a high resolution synthetic radar pulse 175 against a target 174. A reflected signal (not illustrated) is reflected from the target 174 back to the pulse compression system 100. A data processor 172 interfaces with the system 100 and auto-correlates the reflected signal and the emitted high resolution synthetic radar pulse 175. A high resolution image of the target 174 is shown on a display 173 which interfaces with the data processor 172.

Beginning with the launch of SESAT in 1978, Synthetic Aperture Radar (SAR) have provided a wealth of information on such diverse phenomena as surface waves, internal waves, currents, upwelling, shoals, sea ice, wind and rainfall. SAR is the premier sensor for such phenomena because it is sensitive to small surface roughness changes of the order of Radar wavelength (1 millimeter down to several centimeters). It is also independent of solar illumination and is generally unaffected by cloud cover. Most modern RADARs (including SARs) transmit a pulse 175 known as linear modulated waveform and use the standard RADAR principles of range resolution and Doppler shift. Hence the linear FM pulse generator can be replaced with the pulse compression system 100 to produce higher solution in SAR images on the display 173.

Figure 18A:
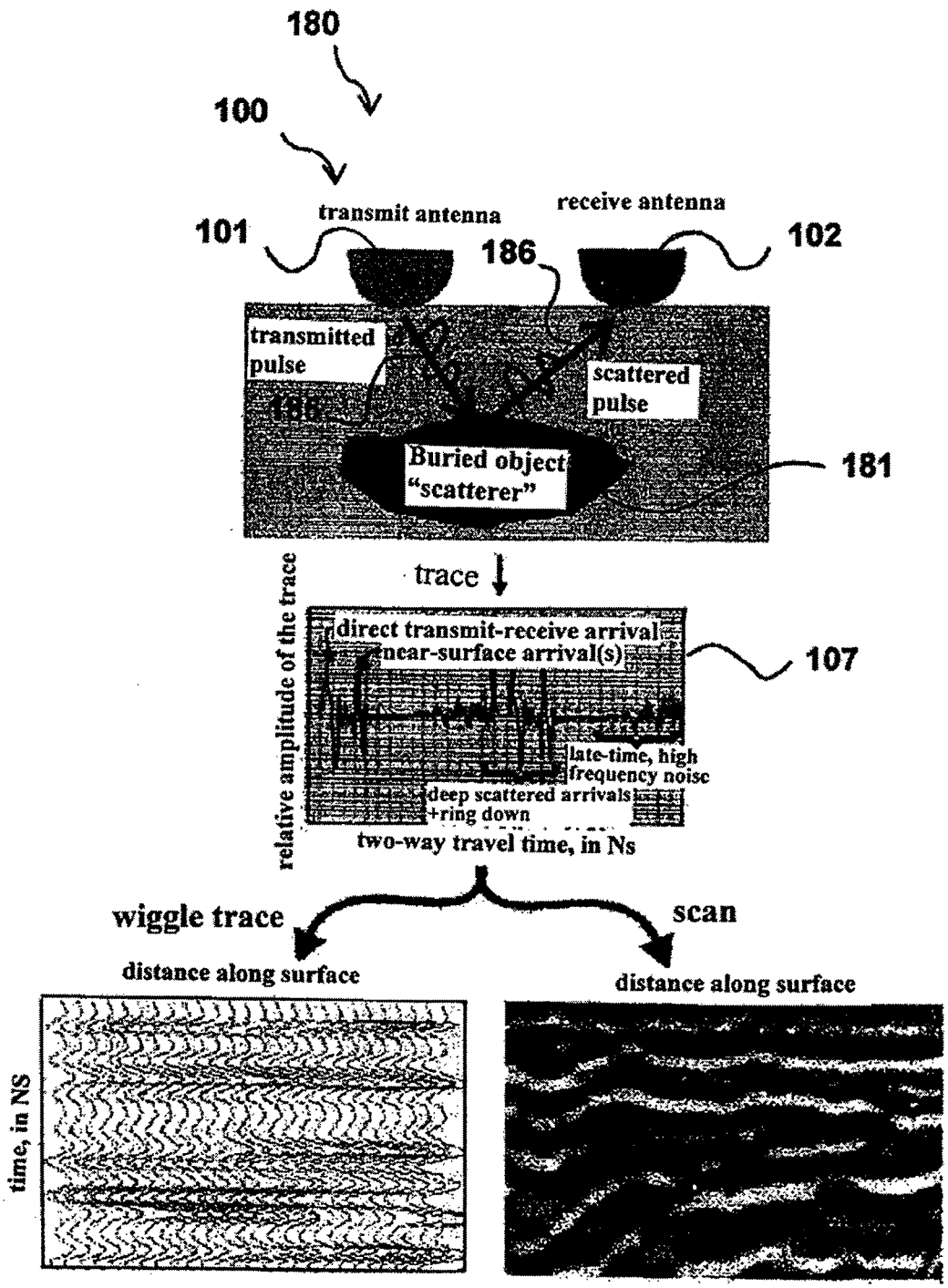
FIGS. 18A-18C are schematic diagrams which illustrate implementation of an illustrative embodiment of the non-linear FM pulse compression system in a high resolution ground penetrating radar application.
Figure 18B:
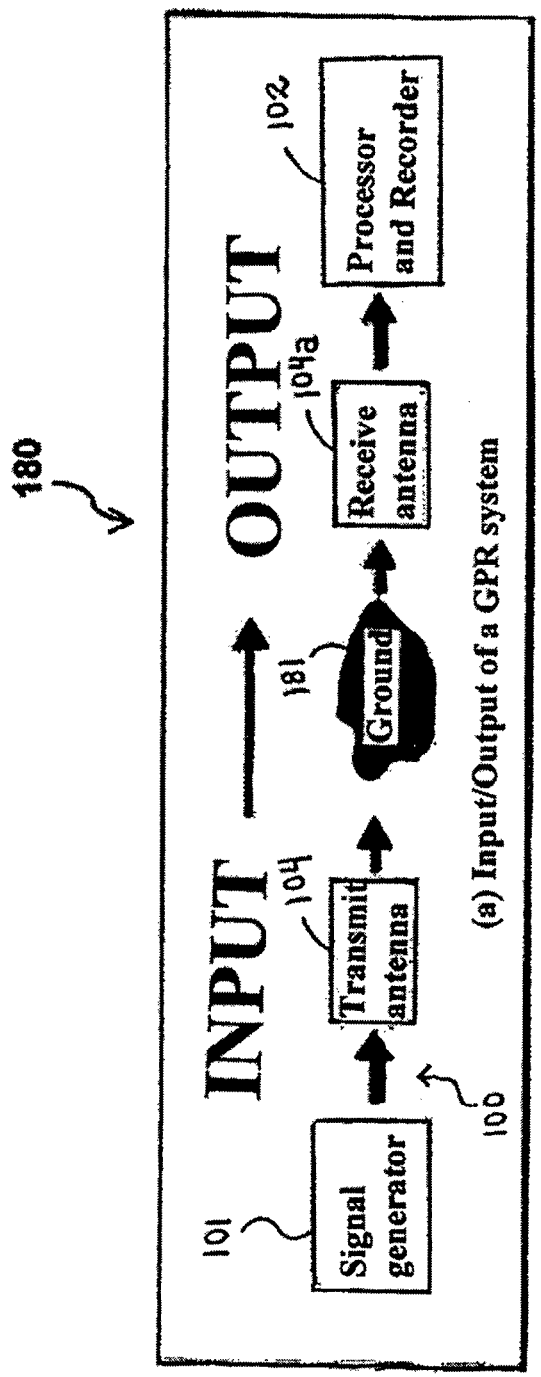
Figure 18C:
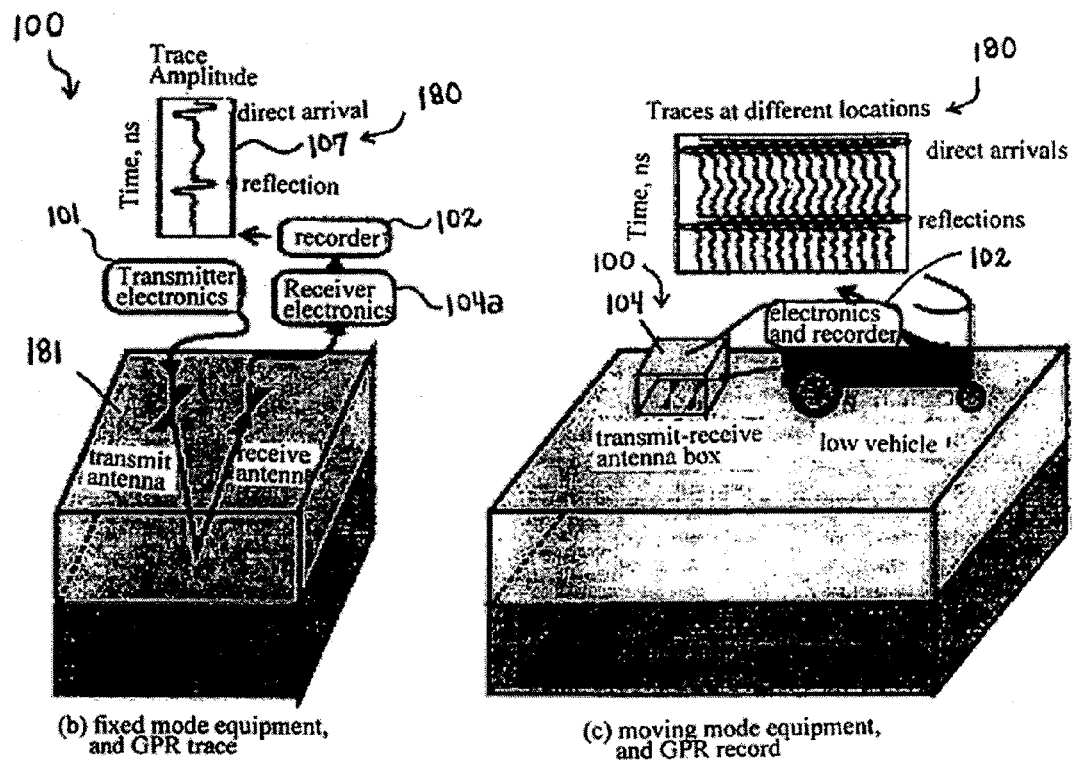

Referring next to FIGS. 18A-18C of the drawings, a high resolution ground penetrating radar system 180 which utilizes an illustrative embodiment of the pulse compression system 100 is illustrated. Ground Penetrating RADAR (GPR) utilizes a very short burst of radio-frequency energy as a pulse 185 which is transmitted from the non-linear FM transmitter 101 via the transmit antenna 104 (FIG. 18B) of the pulse compression system 100 and radiated into the ground 181 to detect discontinuities in the ground 181. The scattered pulse 186 is reflected from the ground 181 and detected by a receive antenna 104a. A signal processor and recorder 102 auto-correlates the scattered pulse 186 and the transmitted pulse 185 and records or displays a high-resolution image of the ground 181 or objects or discontinuities in the ground 181 on a display 107, as illustrated in FIGS. 18A and 18B. Alternative applications of the pulse compression system 100 in implementation of the high resolution ground penetrating radar system 180 are illustrated in FIG. 18C.

The objects or discontinuities in the ground 181 can be cavities, voids, transitions between soil and rock, filled areas and/or buried objects. The performance of conventional GPRs is limited by attenuation of the transmitted pulse in moist soils, especially soils having high clay content. GPRs are used to detect a boundary between rock and air (a cave or cavity) or between one type of soil and another (for example undisturbed soil-to back-filled soil). The strength of the echo signal is dependent on the absorption of the signal to and from the radar to the target, the size and shape of the target, and the degree of discontinuity at the reflecting boundary.

Referring next to FIG. 19 of the drawings, a high resolution air traffic control system 190 which utilizes an illustrative embodiment of the pulse compression system 100 is illustrated. The air traffic control system 190 may include a ground control 191 having a ground control tower 192. The pulse compression system 100 may be provided in the ground control tower 192. An antenna 104 of the pulse compression system 100 emits pulses 193 which are reflected from flying aircraft 194. Return pulses (not illustrated) reflected from the aircraft 194 are received by the antenna 104 and processed as was heretofore described with respect to FIG. 11 to generate a high-resolution image of the aircraft 194.

Air traffic control systems are critically dependent on the use of RADAR technology for the safety of tens of thousands of aircrafts and millions of passengers every day. With the increase in air traffic, there is need for high resolution air traffic tracking systems. Currently, pulsed radars and FMCW radars are used for range measurement and Doppler measurements. With the use of the non-linear FM pulse compression system 100, the performance of the air traffic systems 190 can be significantly improved with more accurate estimation and detection of aircraft 194. In particular, the relative positions of those aircraft 194 which would otherwise come within dangerously close proximity to each other may be detected sufficiently early to prevent such close proximity and avert potential aviation accidents.

A free electron laser (FEL) is a laser which shares the same optical properties as conventional lasers such as emission of an electron beam having coherent electromagnetic radiation which can reach high power but which uses some very different operating principles to form the beam. Unlike gas, liquid or solid-state lasers such as diode lasers, in which electrons are excited in bound atomic or molecular states, FELs use a relativistic electron beam as the lasing medium which moves freely through a magnetic structure (hence the term free electron). The free electron laser has the widest frequency range of any laser type and can be widely tunable, currently ranging in the wavelength from microwaves through terahertz radiation and infrared, to the visible spectrum, to ultraviolet, to X-ray.

Figure 20:
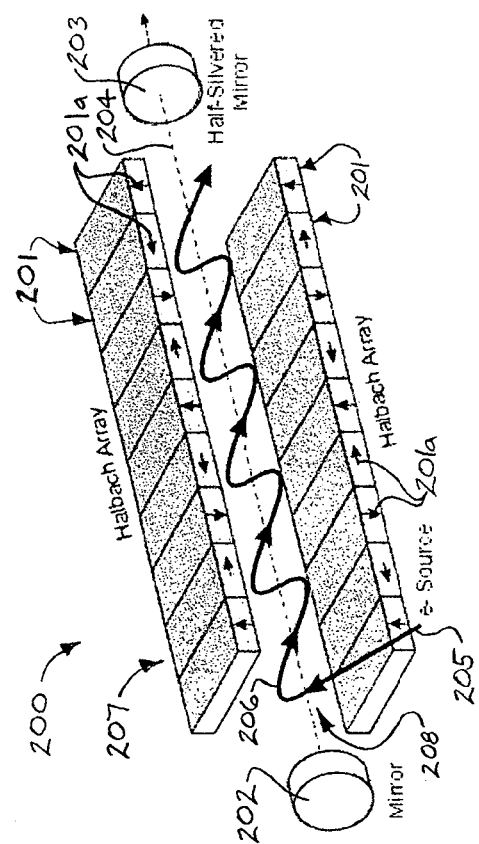
FIG. 20 is a schematic diagram which illustrates implementation of an illustrative embodiment of a free electron laser system.

Referring next to FIG. 20 of the drawings, a free electron laser system 200 is illustrated. In the free electron laser system 200, an FEL oscillator in the form of a "wiggler" or undulator 207 includes two parallel series of permanent magnets 201 having alternating poles 201a. A full-silvered mirror 202 and a half-silvered mirror 203 may be placed at opposite ends of the undulator 207. An electron source 205 is adapted to emit an electron beam 206 to almost light speed (relativistic speed) into a laser cavity 208 between the parallel series of magnets 201 and within a path of light 204 between the full-silvered mirror 202 and the half-silvered mirror 203.

The array of magnets 201 of the undulator 207 forces the electrons in the electron beam 206 to follow a sinusoidal path. The acceleration of the electrons along the sinusoidal path of the electron beam 206 results in a release of a photon (synchroton radiation). Since the electron motion is in phase with the field of the light 204 already emitted, the fields add together coherently. Whereas conventional undulators would cause the electrons to radiate independently, instabilities in the undulators and the radiation they emit leads to bunching of the electrons, which continue to radiate in phase with each other.

Figure 21:
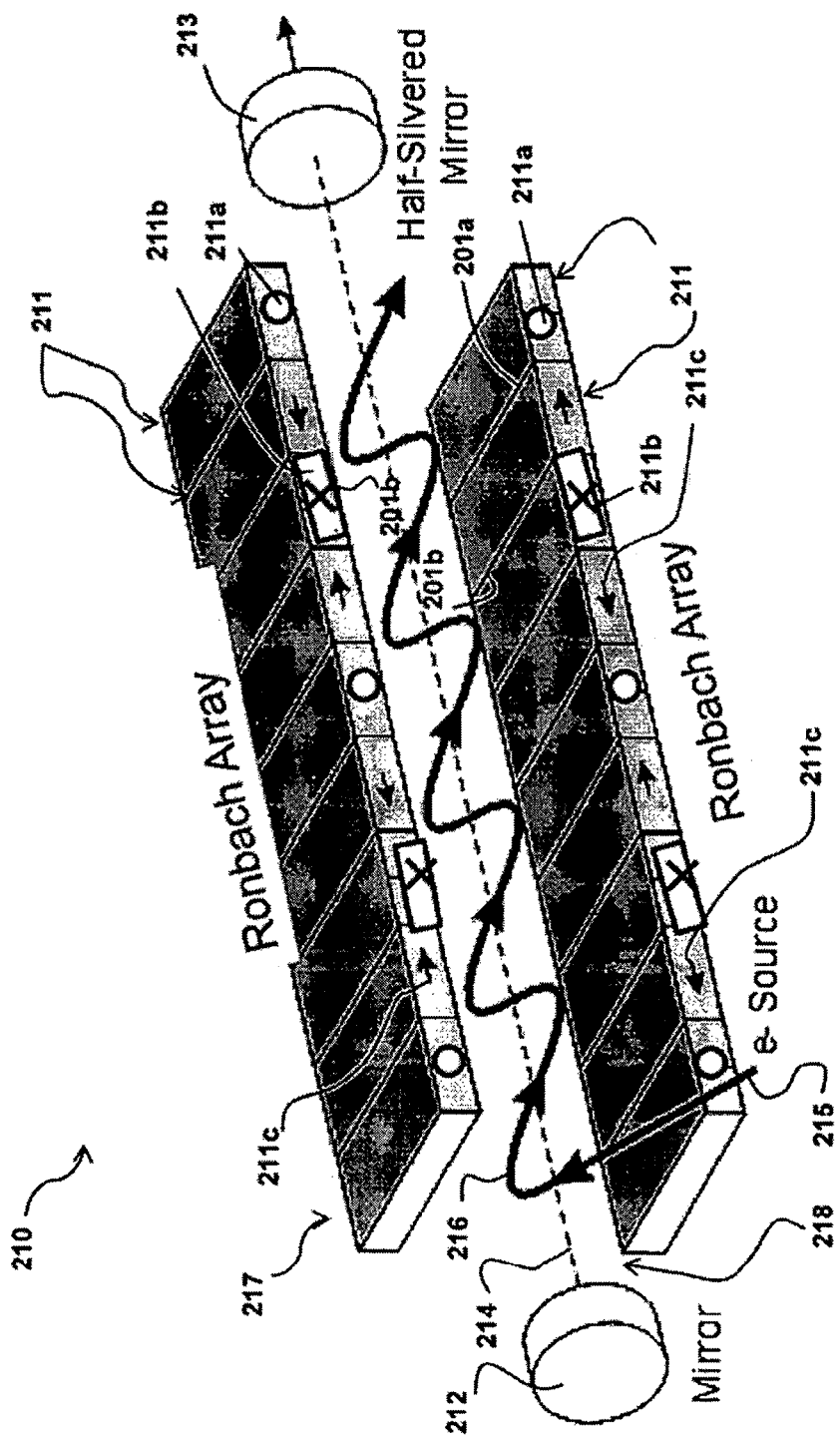
FIG. 21 is a schematic diagram which illustrates implementation of an alternative illustrative embodiment of a free electron laser system.

Referring next to FIG. 21 of the drawings, a schematic diagram which illustrates implementation of an alternative illustrative embodiment of a free electron laser system 210 is illustrated. In the free electron laser 210, each undulator 217 includes two parallel series of permanent magnets 211 each of which is a modified Halbach array (hereinafter referred to as a "Ronbach" array) in which the magnetic north pole 211a and the magnetic south pole 211b of alternating magnets face the same direction. A full-silvered mirror 212 and a half-silvered mirror 213 may be placed at opposite ends of the undulator 217. An electron source 215 is adapted to emit an electron beam 216 to almost light speed (relativistic speed) into a laser cavity 218 between the parallel series of magnets 201 and within a path of light 214 between the fullsilvered mirror 212 and the half-silvered mirror 213. The Ronbach magnetic array of the undulator 217 may result in 71% increase of magnetic field as opposed to 41% increase of magnetic field for Halbach magnetic arrays.

Figure 22:
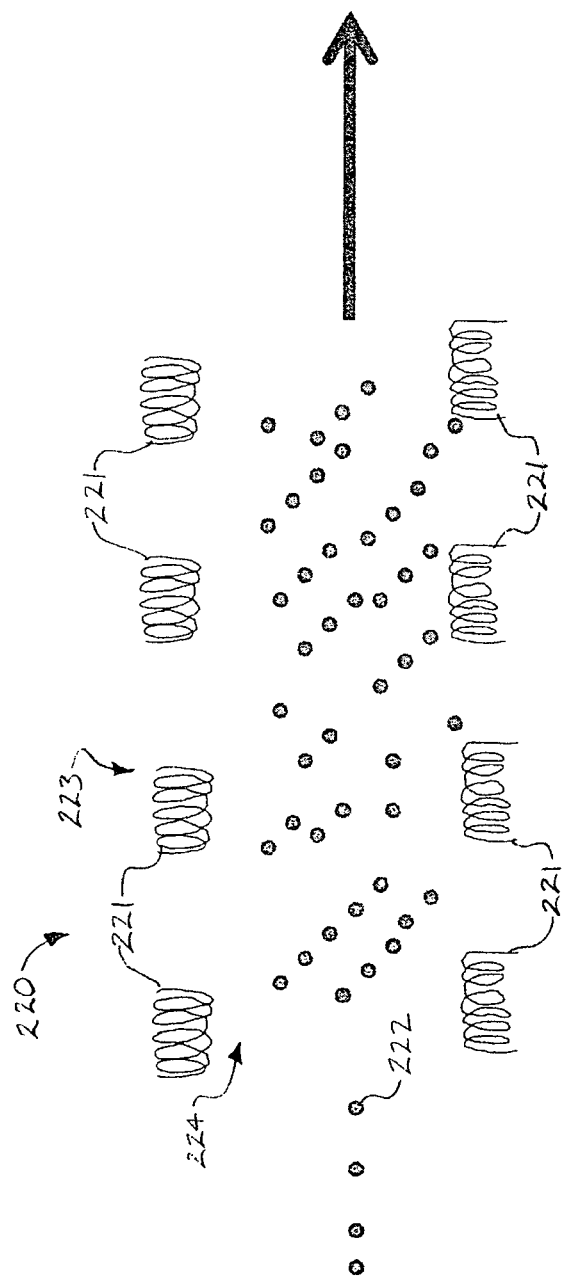
FIG. 22 is a schematic diagram which illustrates implementation of another alternative illustrative embodiment of a free electron laser system.

Referring next to FIG. 22 of the drawings, a schematic diagram which illustrates implementation of another alternative illustrative embodiment of a free electron laser system 220 is illustrated. The undulator 223 of the free electron laser system 220 may include two parallel series of electromagnets with random phase distribution 221. A laser cavity 220 may be defined between the parallel series of electromagnets with random phase distribution 221. Accordingly, the magnetic polarity of the electromagnets with random phase distribution 221 is changed at random, inducing a random modulation of the electron beam 222 as it is emitted through the laser cavity 220.

Figure 23:
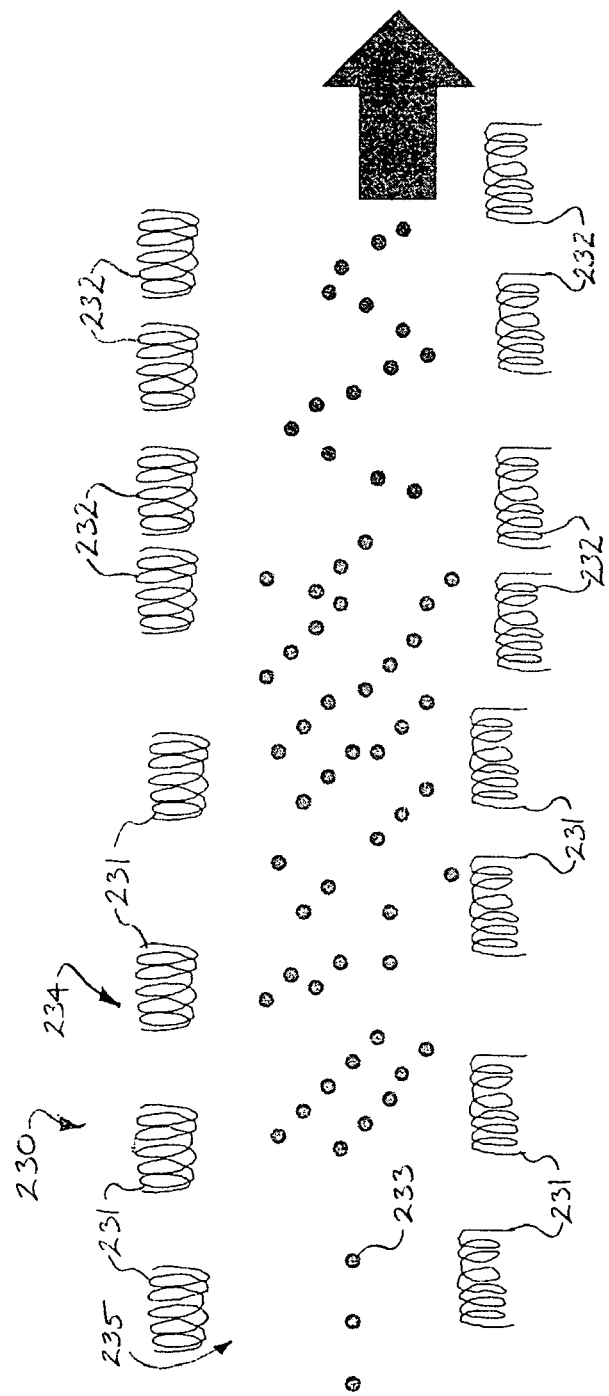
FIG. 23 is a schematic diagram which illustrates implementation of an illustrative embodiment of a free electron laser system.

Referring next to FIG. 23 of the drawings, a schematic diagram which illustrates implementation of an illustrative embodiment of a free electron laser system 230 is illustrated. The undulator 234 of the free electron laser system 230 may include two parallel series of electromagnets with random phase distribution 231 and electromagnets with alternating north and south poles 232. A laser cavity 235 may be defined between the parallel series of electromagnets with random phase distribution 221. Accordingly, the free electron laser system 230 may be operated in a two-cycle operation in which the electromagnets with random phase distribution 221 are energized during the first cycle and the electromagnets with alternating north and south poles 232 are energized during the second cycle. This causes the electron beam 233 to undergo several oscillations, resulting in radiation of intense concentrated energy in narrow energy bands of the spectrum as it is emitted through the laser cavity 235.

Structured Randomly Permutated Pulse Compression Generating System

In some embodiments, a structured randomly permuted pulse compression generating system can be utilized to modulate an input signal to generate a modulated output signal to be directed toward a target. Such systems can more easily distinguish targets that are close together. These targets can be moving and/or stationary targets.

More specifically, the systems can be utilized to more easily distinguish signals generated from targets that are close together. For example, in the context of air traffic control, such systems can distinguish planes that are close together which can allow air traffic controllers to more easily track arriving and departing planes, or other planes that are located closer together. This in turn can allow more planes to fly in the sky at the same time and thereby increase bandwidth in the air and also bandwidth at an airport for allowing a greater number of departures and arrivals of planes. In the context of missiles, these systems can easily identify a multitude of missiles flying close together and target each individually for destruction. In the context of ultrasound, by utilizing these systems one can more easily and clearly identify and view body structures that are positioned close together. For example, small body parts of a developing baby that are located close to each other and/or other tissue in a human body can be observed despite their close proximity. Further, in the context of star gazing into space, these systems can be utilized to distinguish one or more stars that are located close to each other. The advantage of systems disclosed herein is that they can distinguish and identify targets and/or objects that are close together, whereas other systems that do not have such capability can display objects that are close together as a single object. By achieving greater resolution of targets and/or objects, the systems disclosed herein can produce better and clearer images for users to view and allow other systems to perform tasks not otherwise achievable with lower resolution systems.

In some embodiments, a structured random permutation pulse compression system is configured to take an input signal and modulate the input signal by randomly selecting time samples of the input signal to generate an output signal such that none of the selected time samples are reused in generating the output signal. The input signals into the system can comprise any known pulse compression signal and/or uncompressed signal, for example, LFM, NLFM, barker code, random pseudo number algorithm, and rectangular pulse, among others. In some embodiments, a structured randomly permutated pulse compression generating system generally works only with digital radar systems because analog radar systems continuously produce signals and therefore cannot be stopped in order to randomize the signal. However, in other embodiments, a structured randomly permutated pulse compression generating system can be used in conjunction with analog radar systems as well.

A structured randomly permutated pulse compression generating system is generally superior to a conventional pulse compression technique such as linear frequency modulation, non-linear frequency modulation, Barker code and random pseudo number algorithms, resulting in a far superior range and Doppler resolution. Also the system can be far more robust in the presence of noise and can be less affected by the speed of moving targets.

Figure 24:
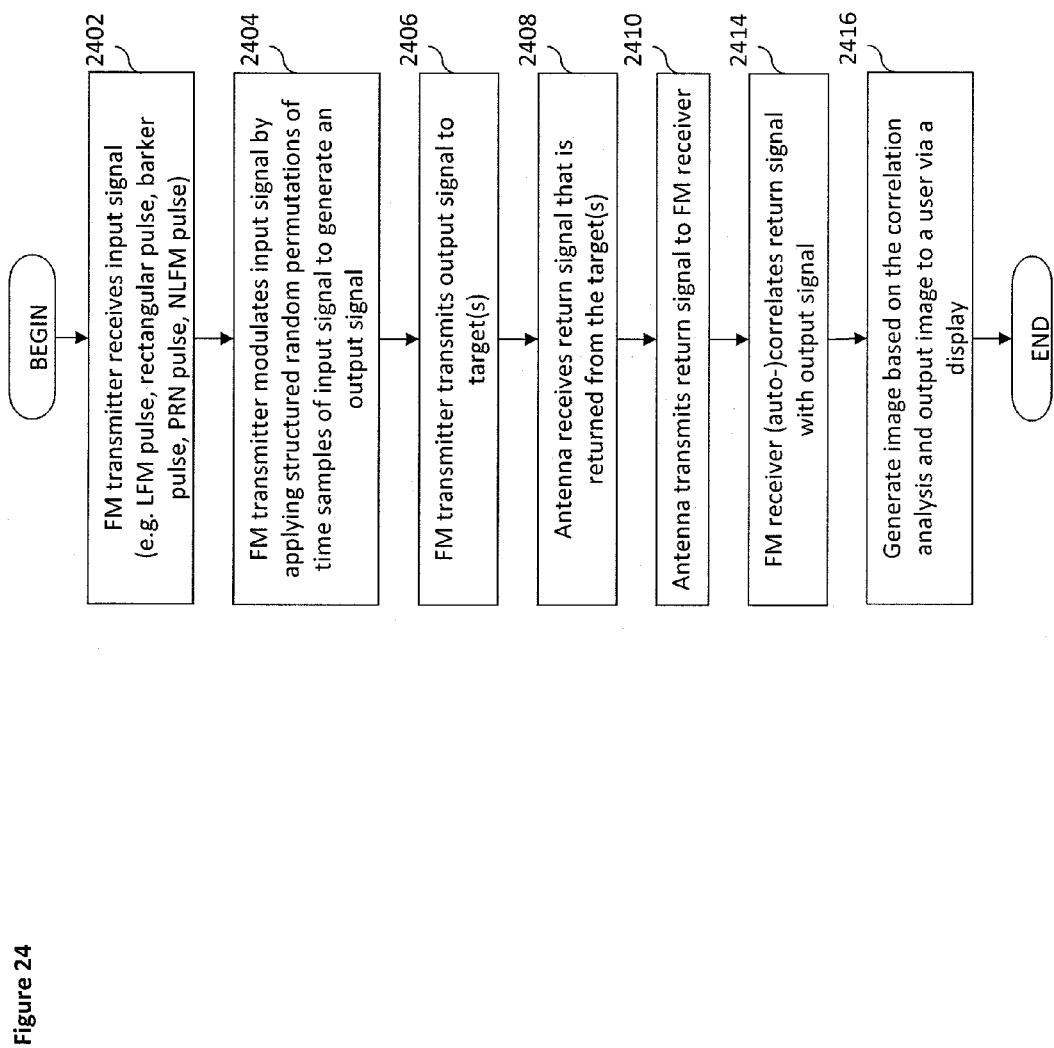
FIG. 24 depicts an embodiment of a process flow diagram illustrating an example of generating an image based on a structured randomly permutated pulse compression signal.

FIG. 24 is a flow diagram illustrating an embodiment of the structured randomly permutated pulse compression generating system. In an embodiment the method can begin at block

2402 when an FM transmitter receives an input signal. The input signal can be any type of radio signal that is currently known or to be developed in the future. In some embodiments, the input signal is already compressed by one or more methods. For example, the input signal can be an FM pulse, a rectangular pulse, a Barker pulse, a PRN pulse and/or an NLFM pulse. The input signal can also be compressed by one or more other pulse compression techniques that are currently known or to be developed in the future.

At block 2404 the FM transmitter can modulate the input signal by applying structured random permutations of time samples of the input signal to generate an output signal. By doing so the spectrum can become sufficiently small and/or narrow to recognize or identify closely positioned objects. In contrast to a simple random permutation where a set of numbers are randomized with the same number potentially appearing more than once, in a structured random permutation a set of numbers are randomized while ensuring that a same number appears only once after the random permutation process. The time sample of the input signal can comprise any number of time samples. For example, a structured random permutation can be applied to time samples from 1 through N to obtain an output signal. For example, the system can be configured to take a plurality of time samples from 1 through N from an input signal and determine the amplitude of the signal at the randomly selected time samples to generate a structured randomly permutated output signal, wherein no previously selected time samples are reused.

In some embodiments, this output signal is then transmitted to one or more targets by an FM transmitter at block 2406. After the output signal reaches the one or more targets, in some embodiments one or more antennas at block 2408 receives a return signal that is reflected from the one or more targets. The return signal can generally be a destructive wave that is generated as a result of the output wave hitting a target and being reflected back to the one or more antennas. In some embodiments, the one or more antennas then transmit the return signal to an FM receiver at block 2410.

In certain embodiments, the FM receiver can be configured to correlate and/or auto correlate the return signal with the output signal that was initially transmitted to the one or more targets at block 2414. In other words, the FM receiver can be configured to compare the destructive return signal to the output signal that was sent to the one or more targets to determine differences between the two signals. Based on the determined differences, an image can be generated and displayed to a user via one or more displays at block 2416. This image can be a representation of the location of the one or more targets, whether the targets are moving or are stationary.

Figure 25:
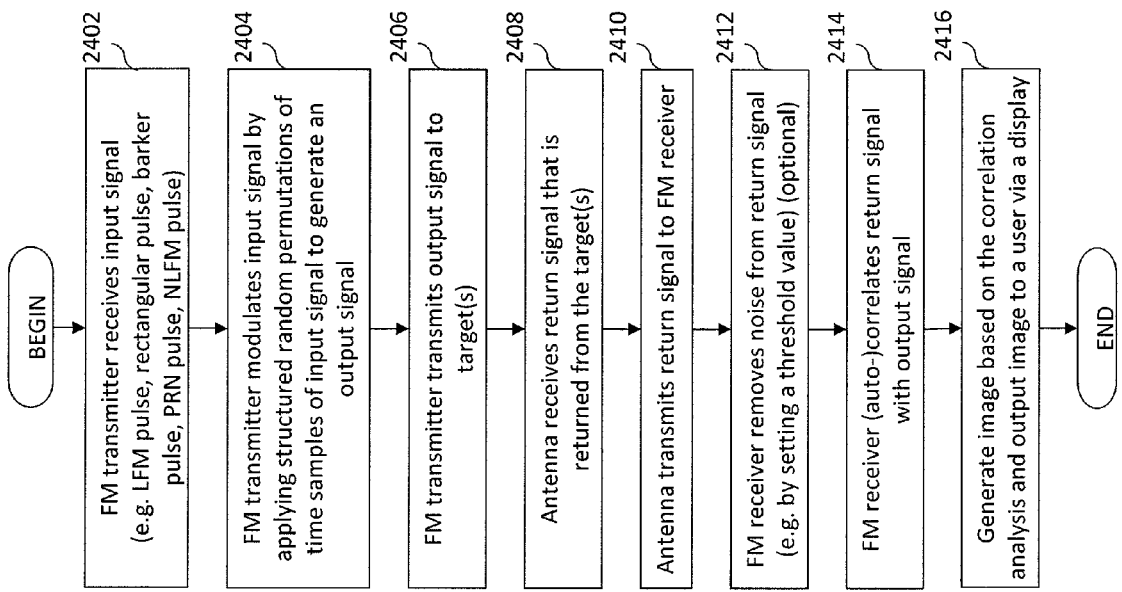
FIG. 25 depicts an embodiment of a process flow diagram illustrating an example of generating an image based on a structured randomly permutated pulse compression signal.

FIG. 25 is a flow diagram illustrating an embodiment of the structured randomly permutated pulse compression generating system. The flow diagram illustrated in FIG. 24 can optionally be amended as shown in FIG. 25 to include an optional block 2412 to remove noise from the return signal. As illustrated, in some embodiments, the FM receiver can be configured to remove noise from the return signal at block 2412. For example, the FM receiver can be configured to set a threshold value to remove at least a portion of the noise. This threshold value, for example, can be set at 0.5 or at any other value, for example, 0.1, 0.2, 0.3, 0.4, 0.6, 0.7, 0.8, 0.9, 1.0, or the like. If the threshold value is set at 0.5, then any data that exceeds the threshold value of 0.5 is thereby removed creating a cleaner image of data. By removing the noise or a portion thereof, the system can more effectively compare the return signal to the output signal in some embodiments and/or generate a substantially cleaner image.

Performance of Structured Randomly Permutated Pulse Compression Generating Systems Experiments have been conducted to highlight the advantages of the structured random permutation systems described herein. A summary of these experiments is discussed below. In order to systematically compare the range and Doppler resolution capabilities of the structured randomly permutated pulse compression generating system to those pulse compression systems that are currently known, a cross ambiguity function can be utilized as a tool for analysis. For example, a radar pulse can be cross-correlated with two closely separated echo pulses of the same type but corrupted by adding random noise to the return pulses. Also, the effect of motion of the targets can be simulated by altering the center frequency of the return echo proportionally to the speed of a target.

For analysis, one or more parameters estimated from the cross ambiguity function can be considered. For example, some of these parameters can include the range resolution of the closely spaced targets, the Doppler resolution of the closely spaced targets, the maximum probability defined as the maximum value of cross ambiguity multiplied by the number of pixels in the cross ambiguity function, and the maximum to second peak ratio defined as the ratio of the maximum value of the cross ambiguity functions to the second non-target maximum value expressed in decibels, namely 20 log 10 (Maximum Value/Second Non Target Maximum value) among others.

In an experiment, a pulse comprising a width of 100 microseconds and operating at 128 megahertz can be considered. Further, noise at a value of three decibels, namely where the average noise power is twice that of the signal power, can be added. The targets can be assumed to be spaced apart by 1% of the pulse width. The radar cross sections of the targets can be assumed to be 100%.

Figure 26:
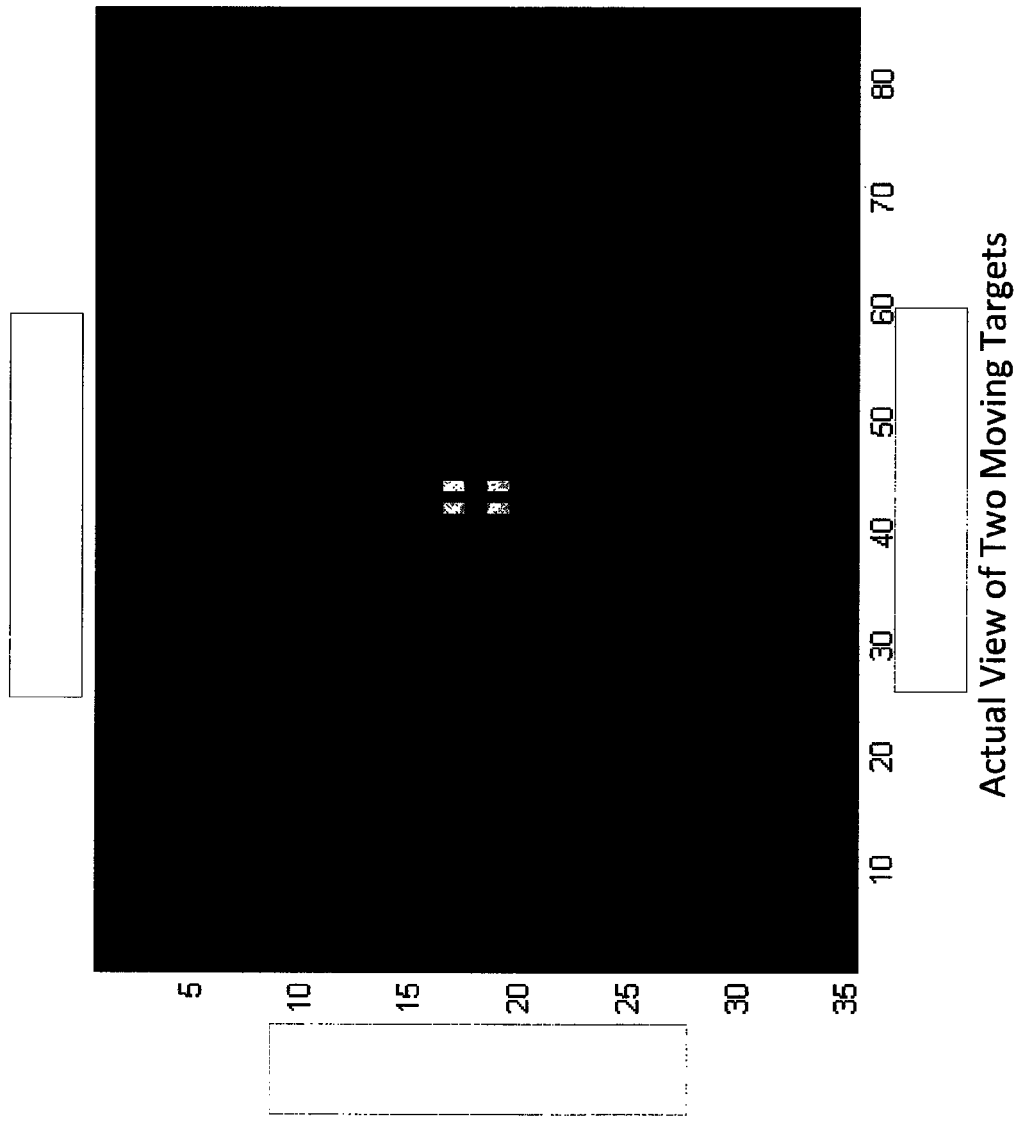
FIG. 26 is an embodiment of a schematic diagram illustrating a view of two moving targets.

Performance of Structured Randomly Permutated Pulse Compression Generating Systems—Two Moving Targets In an experiment, two moving targets spaced apart at 1% of the pulse width moving at 700 miles per hour and in the presence of noise of three decibels were analyzed and evaluated using pulse compression systems currently known with the structured random permutation systems described herein. FIG. 26 illustrates an actual view of two moving targets 2602, 2604. As illustrated, two vertical lines corresponding to the two moving targets 2602, 2604 are located in the center of the screen, depicting the approximate location and distance of separation between the two moving objects 2602, 2604. An ideal detection system will generate an image of the moving targets that is substantially similar to the illustrated actual view of the moving targets as illustrated in FIG. 26.

FIGS. 27A through 31B illustrate the effects of various pulse compression technologies that are existing today. In contrast, FIGS. 32A through 39B illustrate the effects of various structured randomly permutated pulse compressions systems discussed herein.

Figure 27B:
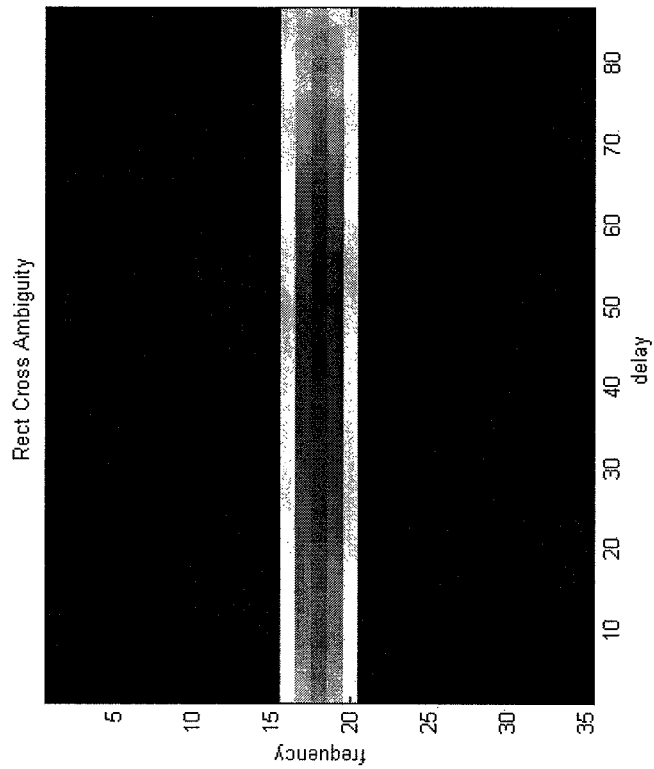
FIGS. 27A and 27B are embodiments of schematic diagrams illustrating images, generated by a rectangular pulse, of the two moving targets.
Figure 27A:
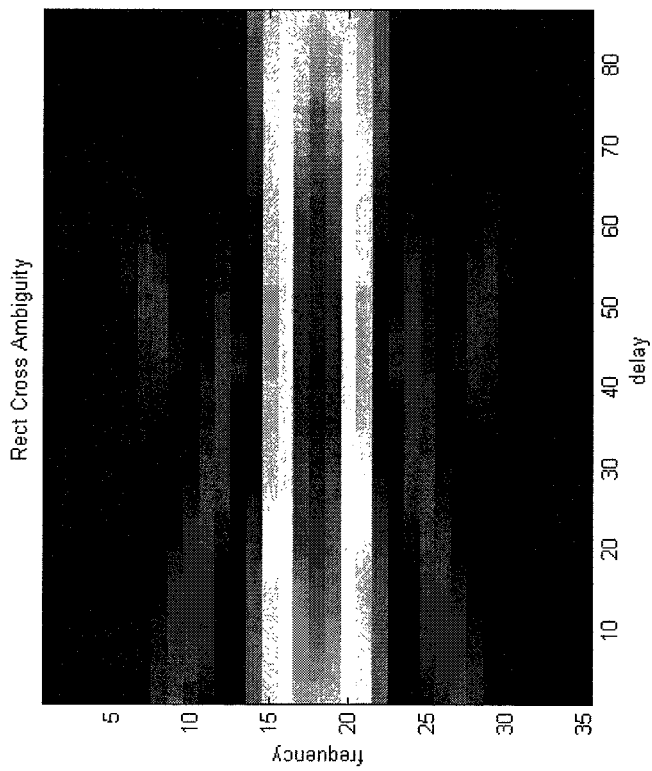

More specifically FIGS. 27A and 27B illustrate the effects of a rectangular pulse. As illustrated in FIG. 27A, what should be two vertical lines located in the center are smeared horizontally thereby making it almost impossible to detect and/or identify the two moving objects from each other. Even after removing some of the noise by setting a threshold maximum value at 0.5, as illustrated in FIG. 27B, the horizontal smears of the two vertical lines are still present.

Figure 28B:
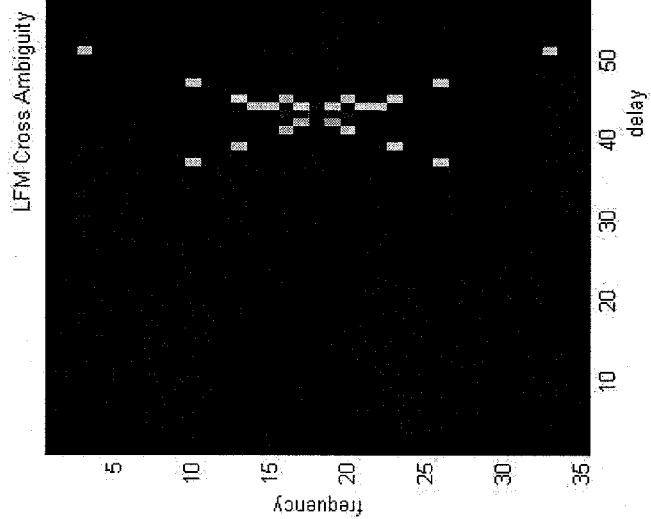
FIGS. 28A and 28B are embodiments of schematic diagrams illustrating images, generated by an LFM pulse, of the two moving targets.
Figure 28A:
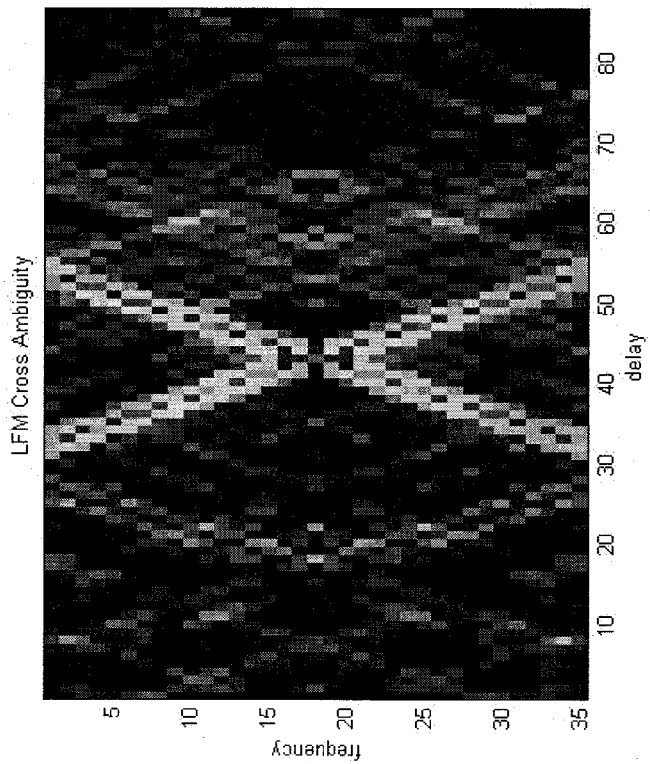

FIGS. 28A and 28B illustrate the effects of a radio signal compressed by linear frequency modulation. As illustrated in FIG. 28A even with LFM the cross ambiguity results in a substantial amount of noise thereby making it difficult if not impossible to ascertain the location of the two moving objects and distinguish one from the other. As shown in FIG. 28B removing the noise by setting the threshold maximum value at 0.5 does not completely resolve this issue. As shown in FIG. 28B a substantial amount of noise is still present around the two vertical lines in the center.

Figure 29B:
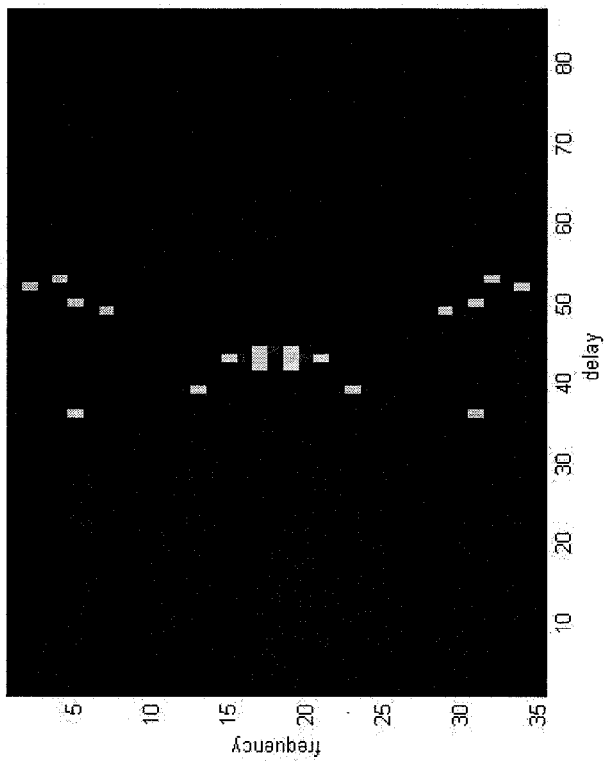
FIGS. 29A and 29B are embodiments of schematic diagrams illustrating images, generated by an NLFM pulse, of the two moving targets.
Figure 29A:
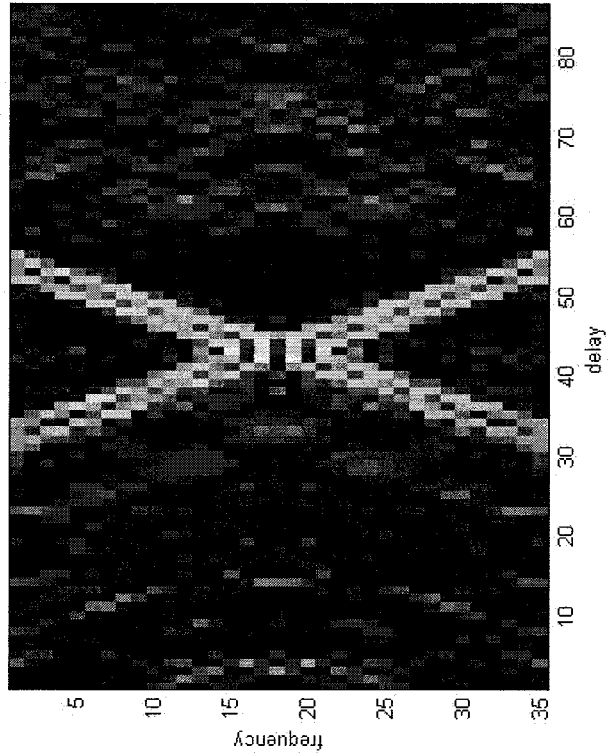

FIGS. 29A and 29B illustrate the effects of applying nonlinear frequency modulation to a radio signal. Again as shown in FIG. 29A a substantial amount of noise is present around the two vertical lines. Even after removing parts of the noise by setting the threshold maximum value at 0.5 a substantial amount of noise is still present in addition to the two vertical lines in the center.

Figure 30B:
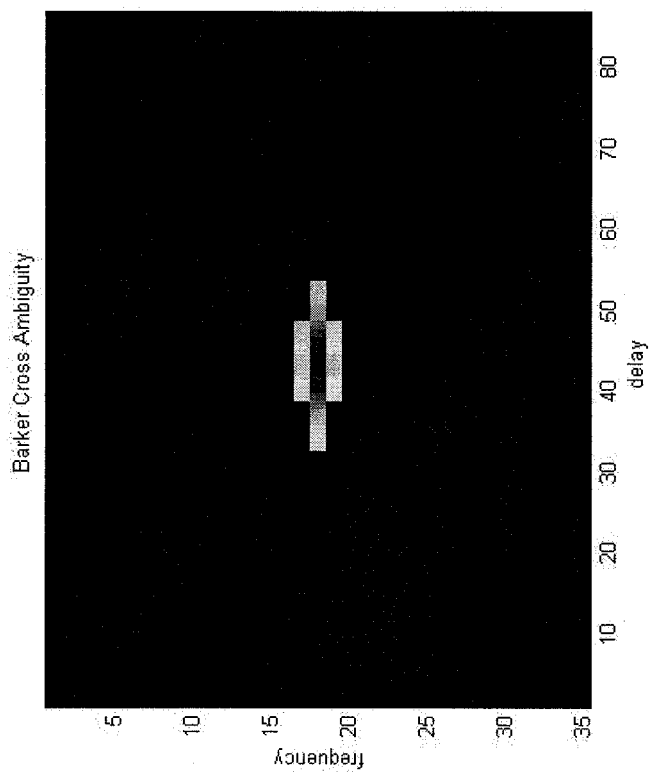
FIGS. 30A and 30B are embodiments of schematic diagrams illustrating images, generated by a Barker pulse, of the two moving targets.
Figure 30A:
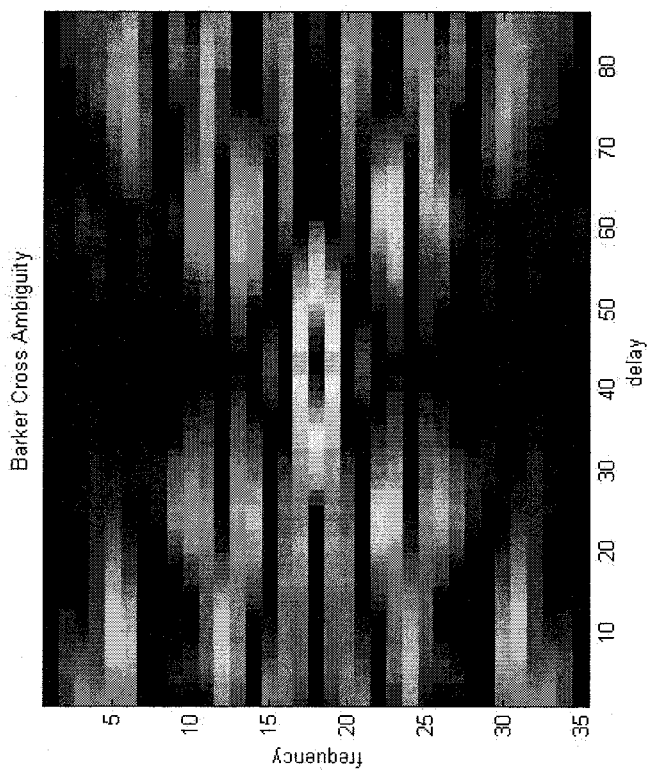

FIGS. 30A and 30B illustrate the effects of Barker code applied to a radio signal. As illustrated in FIG. 30A the two vertical lines in the center are again smeared horizontally. Even after removing a substantial amount of noise by setting the threshold maximum value at 0.5 as shown in FIG. 30B the two vertical lines are still smeared making it still difficult to ascertain the location of the two moving objects and/or isolating one from another.

Figure 31B:
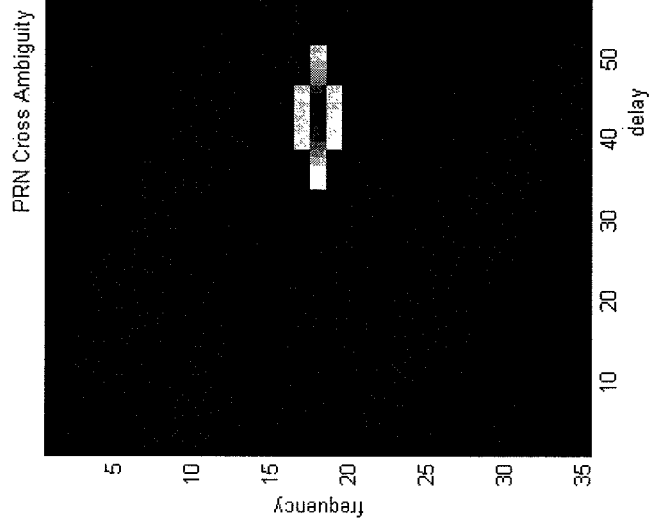
FIGS. 31A and 31B are embodiments of schematic diagrams illustrating images, generated by a PRN pulse, of the two moving targets.
Figure 31A:
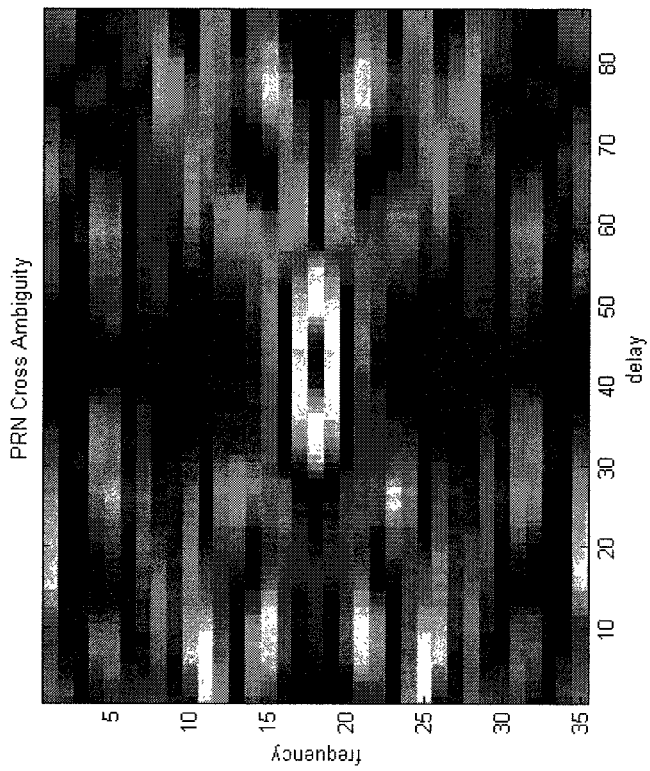

FIGS. 31A and 31B illustrate the effects of random pseudo number algorithms applied to a radio signal. As shown in FIG. 31A the cross ambiguity of a PRN pulse is similarly smeared resulting in a substantial amount of noise. Even after removing some of the noise by setting the threshold maximum value at 0.5 the two vertical lines in the center are still smeared making it difficult to ascertain the location of the two moving objects and/or being able to isolate one from the other.

In comparison, FIGS. 32A through 39B illustrate the effects of applying a structured randomly permutated pulse compression generating system and/or method to one or more pulse compression techniques and/or an uncompressed radio signal.

Figure 32B:
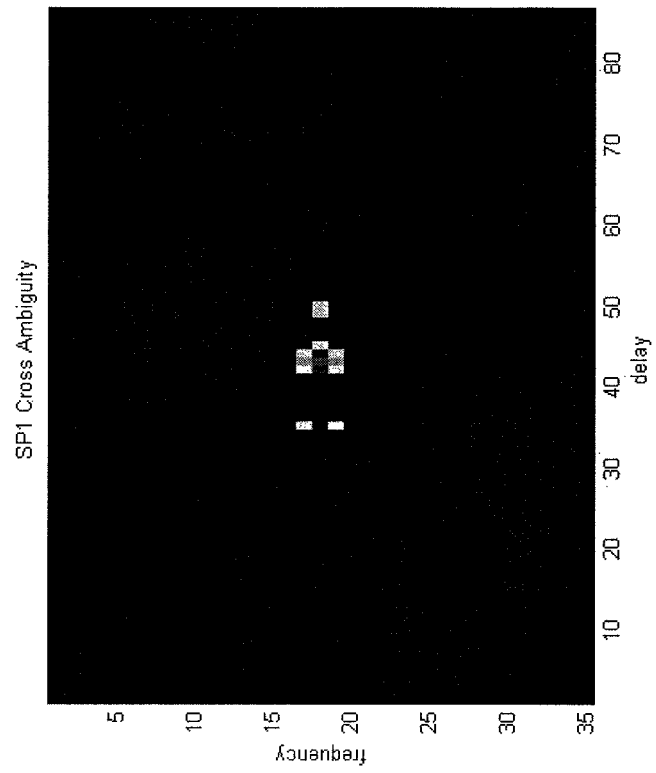
FIGS. 32A and 32B are embodiments of schematic diagrams illustrating images, generated by a chirp signal that increases as a logarithmic function of the frequency of the time samples in the input signal, of the two moving targets.
Figure 32A:
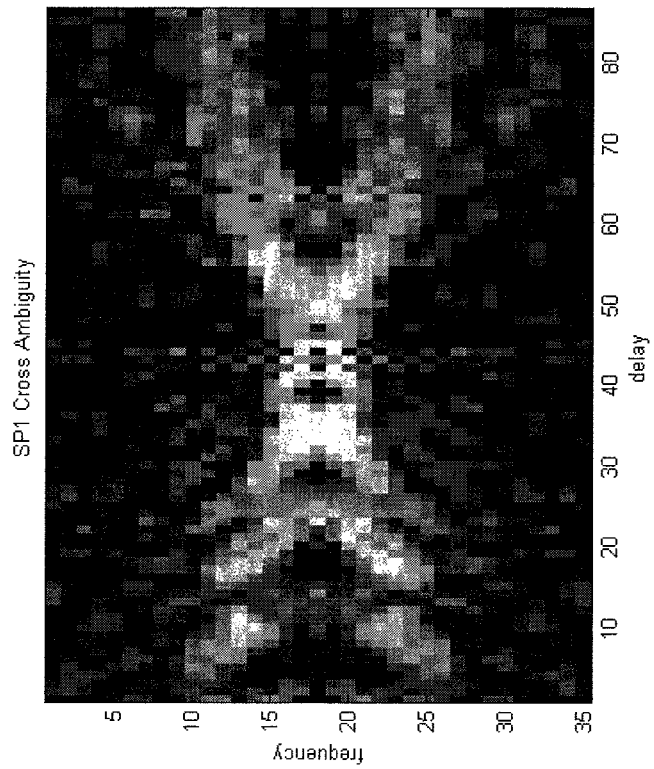

The cross ambiguity analysis illustrated in FIGS. 32A and 32B correspond to an output nonlinear FM chirp signal having a frequency that increases as a logarithmic function of the frequency of the samples in the input signal. This relationship can be described as in Formula 3 discussed above. As shown in FIG. 32A the cross ambiguity analysis of this pulse compression technique (namely "SP1") results in some amount of noise. However by simply setting the threshold maximum value at 0.5, a substantial amount of this noise can be removed, thereby producing a substantially clearer image of the two vertical lines in addition to a few remaining points of noise.

Figure 33B:
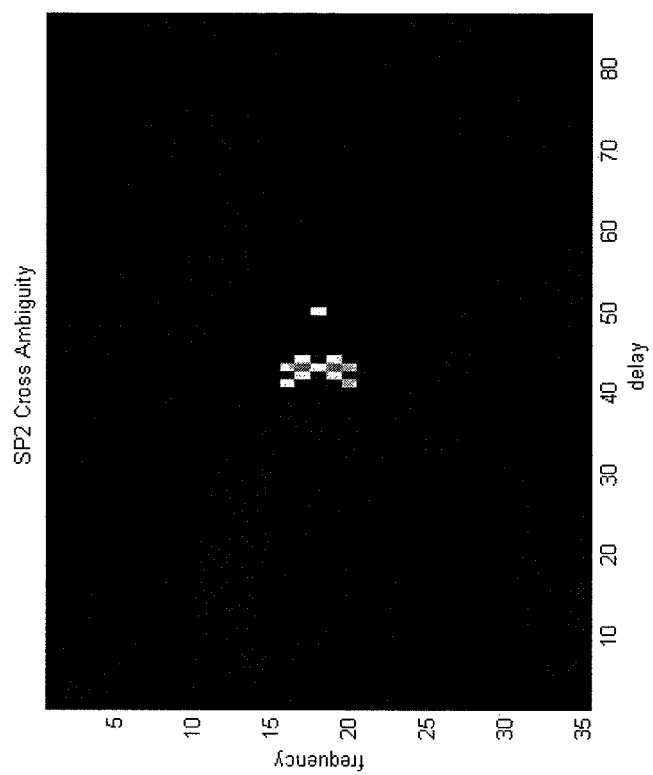
FIGS. 33A and 33B are embodiments of schematic diagrams illustrating images, generated by a chirp signal that is inversely proportional to the frequency of the time samples in the input signal, of the two moving targets.
Figure 33A:
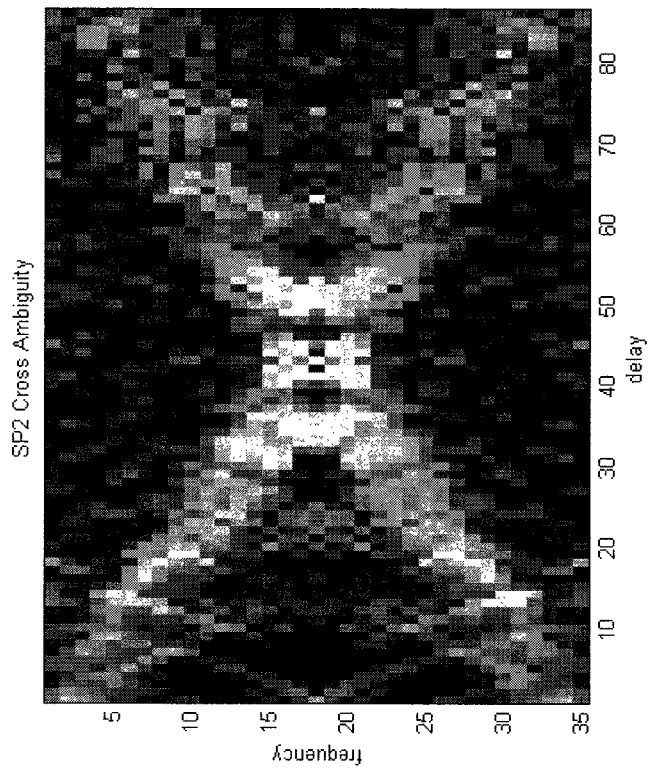

FIGS. 33A and 33B illustrate the ambiguity of another pulse compression technique, namely "SP2." In this pulse compression technique, the frequency changes in the nonlinear FM chirp signal are inversely proportional to the frequency of the samples in the input pulse signal and are given by Formula 4, noted above. As shown in FIG. 33A, there is some amount of noise present in the cross ambiguity of the SP2 pulse. However, similar to SP1, by simply setting the threshold maximum value at 0.5, a substantial amount of this noise can be removed thereby resulting in a substantially cleaner image of the two vertical lines in addition to a few remaining points of noise.

Figure 34B:
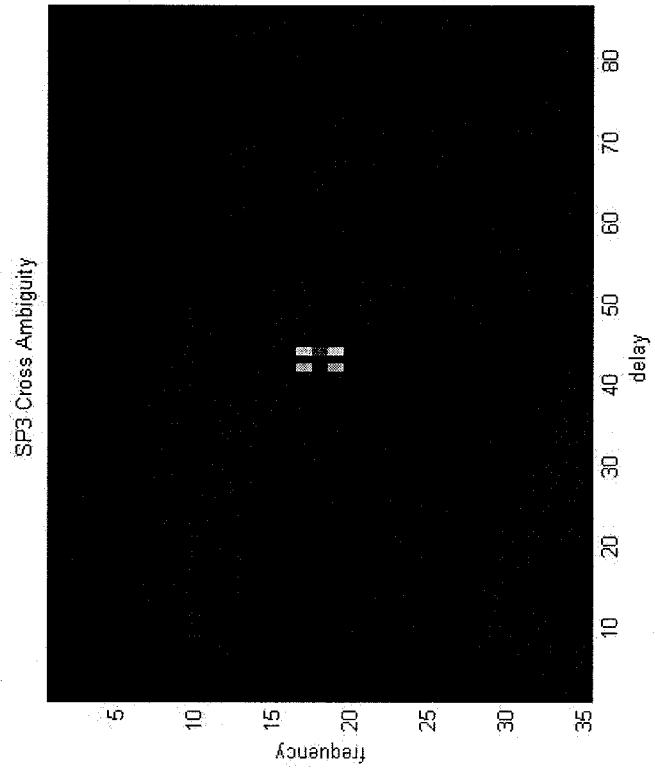
FIGS. 34A and 34B are embodiments of schematic diagrams illustrating images, generated by a chirp signal produced by a random permutation of the input signal, of the two moving targets.
Figure 34A:
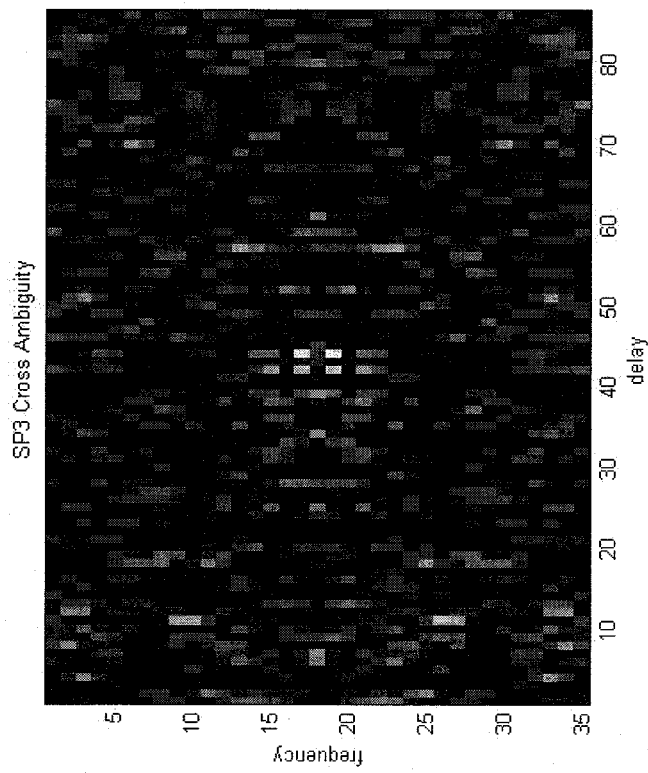

FIGS. 34A and 34B illustrate the cross ambiguity effects of another pulse compression technique, namely "SP3." In this pulse compression technique, the frequency changes of the nonlinear FM chirp signal are produced by a random permutation of the input pulse signal to create a random sinusoid and are given by Formula 5A above. In some embodiments, the structured random permutation may be performed on the input to the sinusoid rather than the output and can be represented by formula 5B above. However, for some applications, performing the random permutation on the output of the sinusoidal pulse may be simpler. As shown in FIG. 34A, some amount of noise is present after utilizing the SP3 pulse compression technique. However, by setting the threshold value at a maximum of 0.5 almost all of the noise is removed, thereby producing a substantially clean image of the two vertical lines as illustrated in FIG. 34B.

Figure 35B:
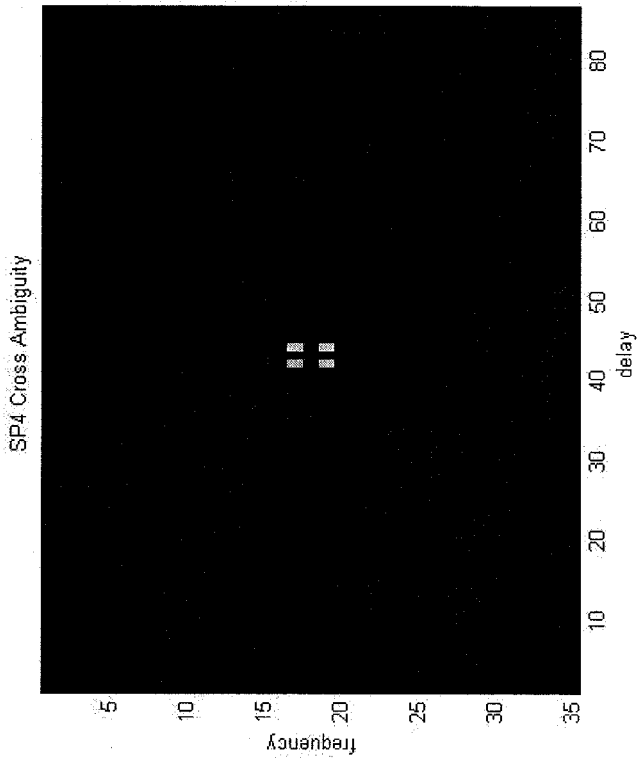
FIGS. 35A and 35B are embodiments of schematic diagrams illustrating images, generated by a randomly permutated LFM pulse signal, of the two moving targets.
Figure 35A:
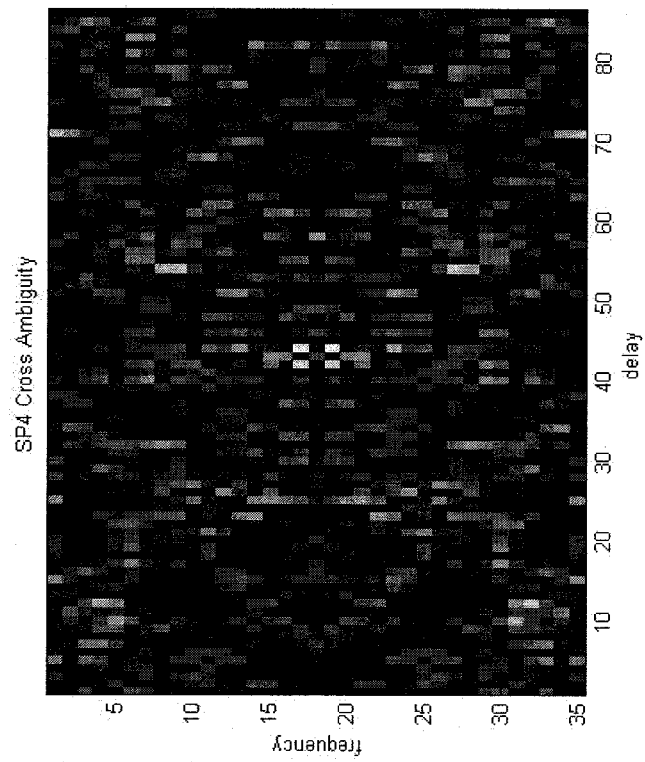

FIGS. 35A and 35B illustrate the effects of structured random permutation of the output of an LFM signal, namely "SP4." As shown in FIG. 35A, some amount of noise is present in the cross ambiguity of this SP4 pulse. However, by setting the threshold maximum value at 0.5, substantially all of the noise is removed, thereby producing a substantially clean image of the two vertical lines as illustrated in FIG. 35B.

Figure 36B:
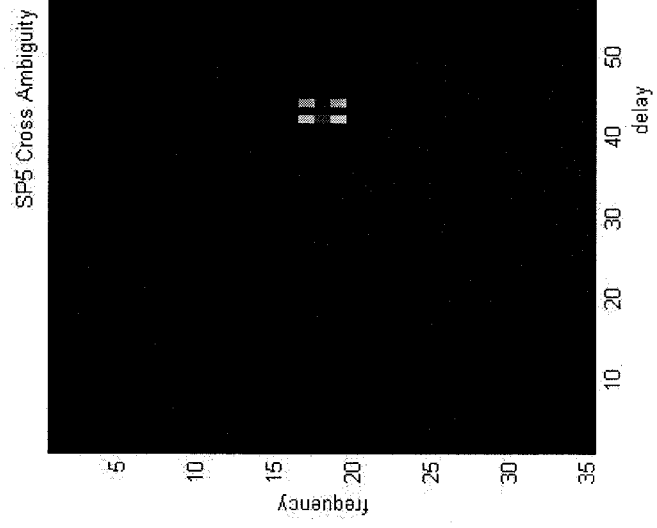
FIGS. 36A and 36B are embodiments of schematic diagrams illustrating images, generated by a structured randomly permutated rectangular pulse signal, of the two moving targets'.
Figure 36A:
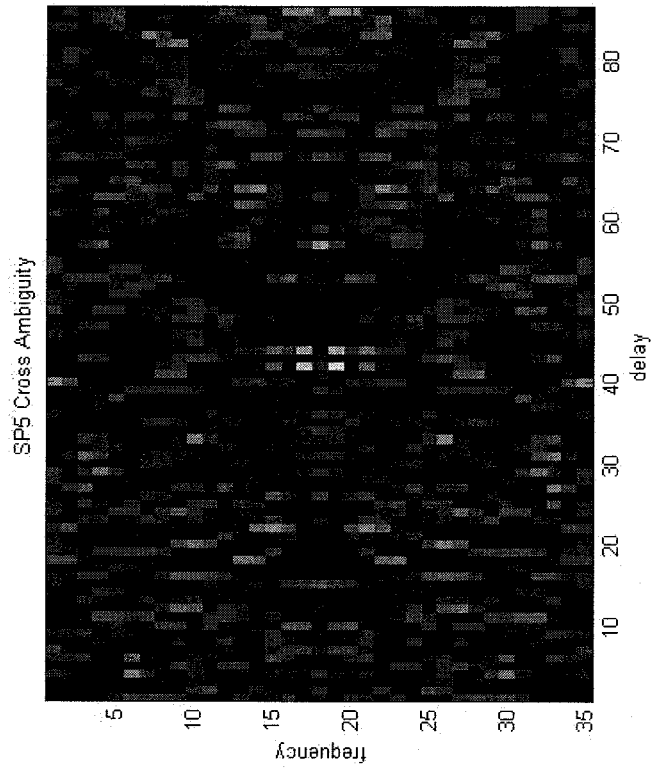

FIGS. 36A and 36B illustrate the effects of applying the structured random permutation algorithm to a rectangular pulse, namely "SP5." As shown in FIG. 36A, some amount of noise is present in the cross ambiguity of an SP5 pulse. However, by setting the threshold maximum value at 0.5, substantially all of the noise is removed, thereby producing a substantially clean image of the two vertical lines as illustrated in FIG. 36B.

Figure 37B:
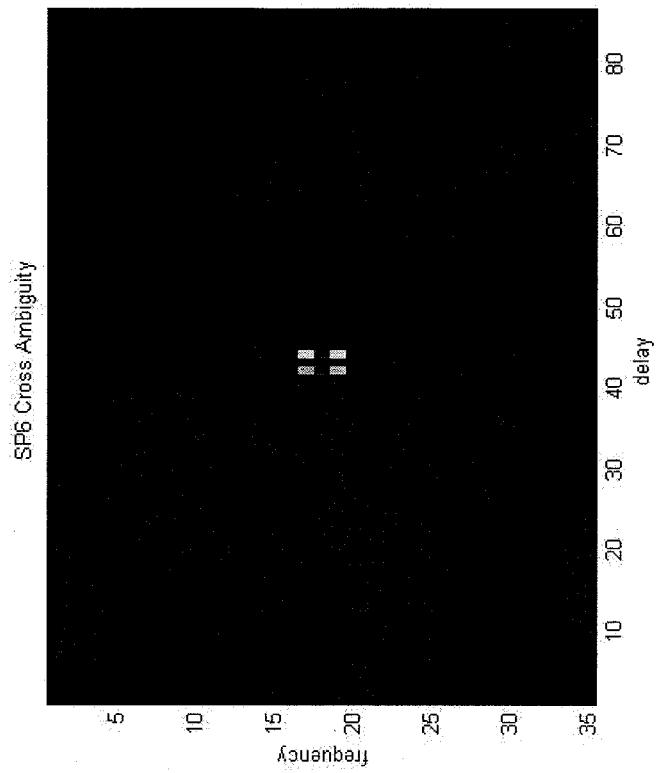
FIGS. 37A and 37B are embodiments of schematic diagrams illustrating images, generated from a structured randomly permutated Barker pulse signal, of the two moving targets.
Figure 37A:
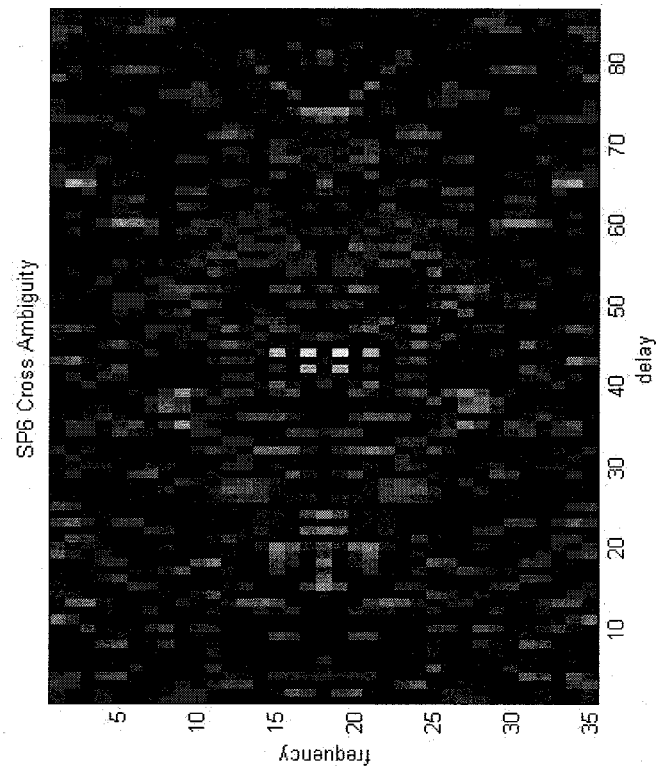

FIGS. 37A and 37B illustrate the effects of applying the structured random permutation technique to a Barker code, namely "SP6." As illustrated in FIG. 37A, the cross ambiguity of this SP6 pulse results in some amount of noise. However, by simply setting the threshold maximum value at 0.5, substantially all of the noise is removed thereby producing a substantially clean image of the two vertical lines.

Figure 38B:
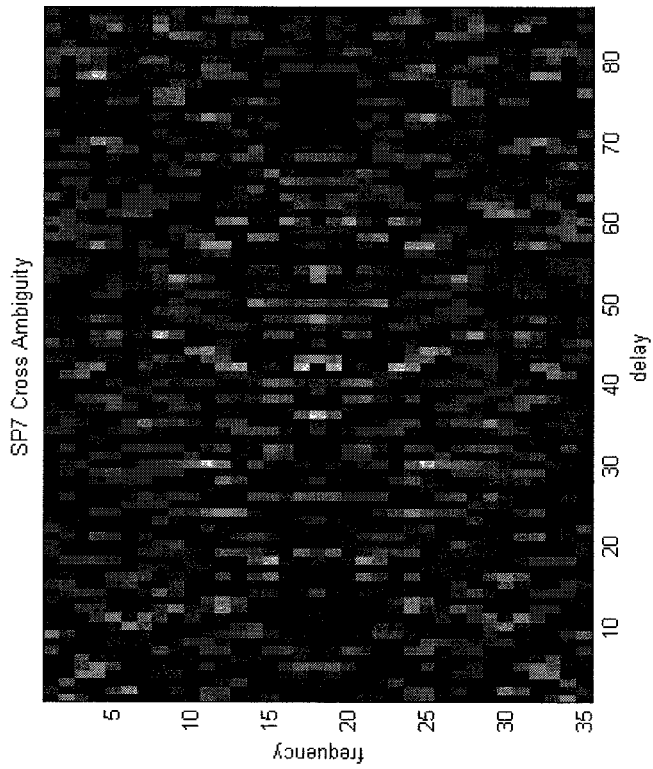
FIGS. 38A and 38B are embodiments of schematic diagrams illustrating images, generated by a structured randomly permutated PRN pulse signal, of the two moving targets.
Figure 38A:
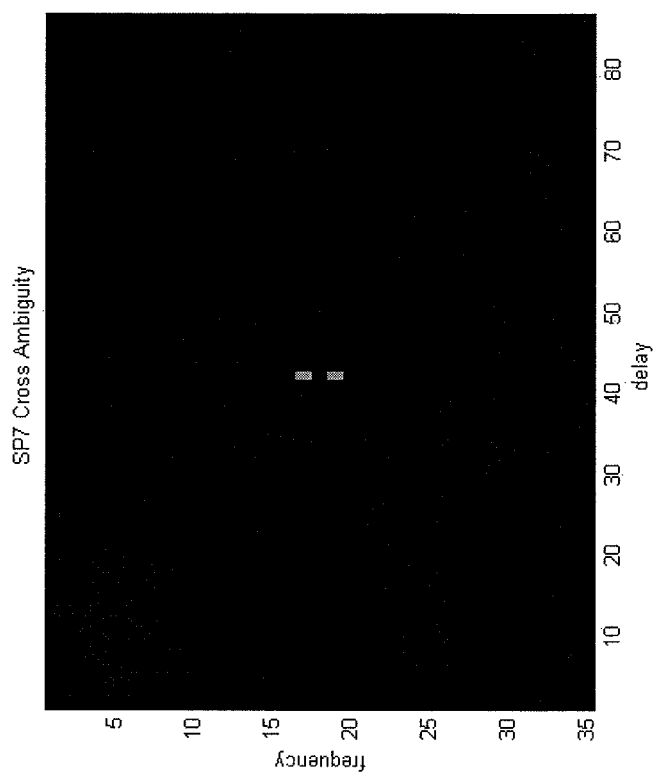

FIGS. 38A and 38B illustrate the effects of applying the structured random permutation technique to a pseudo random number code, namely "SP7." As illustrated in FIG. 38A, the cross ambiguity of an SP7 pulse results in some amount of noise. However, by setting the threshold maximum value at 0.5, substantially all of the noise is reduced, thereby producing a cleaner image as illustrated in FIG. 38B. However, as shown in FIG. 38B, only one of the two vertical lines is obtained.

Figure 39B:
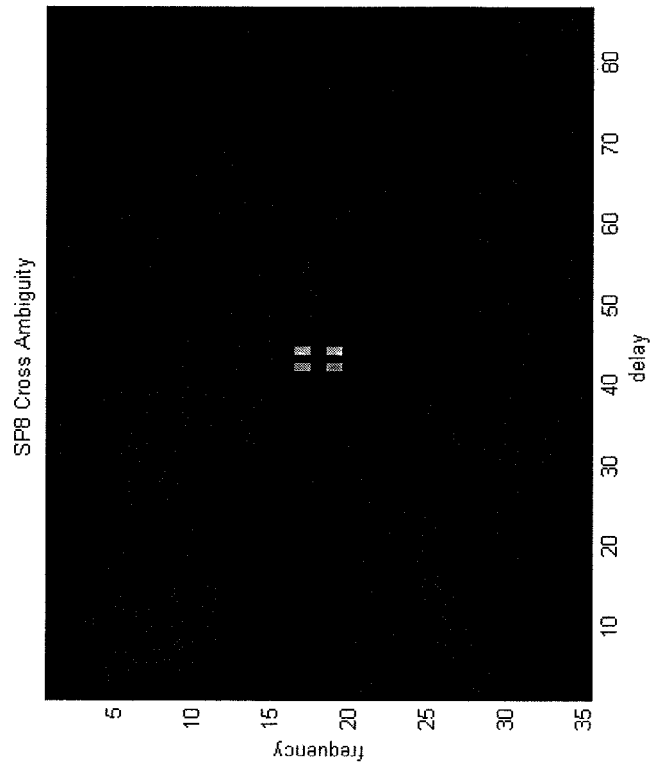
FIGS. 39A and 39B are embodiments of schematic diagrams illustrating images, generated by a structured randomly permutated NLFM pulse signal, of the two moving targets.
Figure 39A:
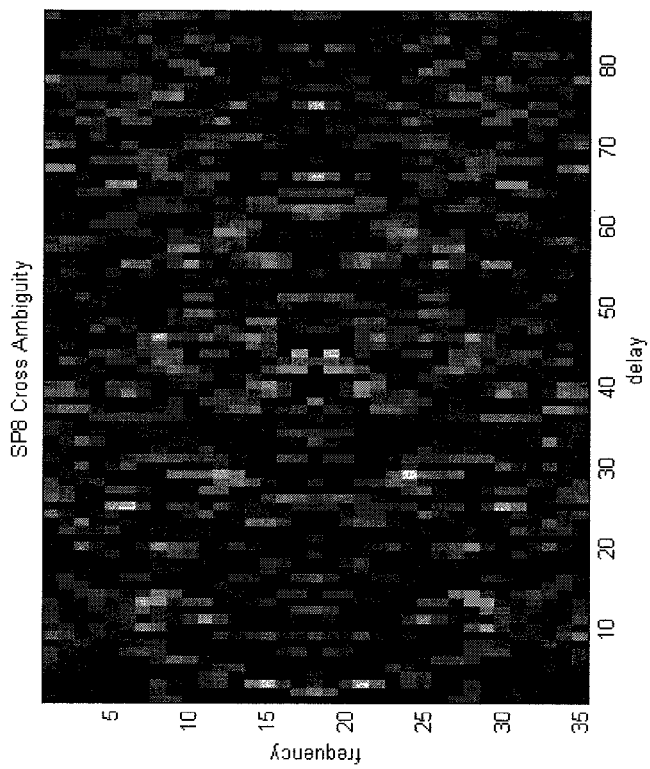

FIGS. 39A and 39B illustrate the effects of applying the structured random permutation technique to an NLFM signal, namely "SP8." As shown in FIG. 39A, a cross ambiguity of the SP8 pulse results in some amount of noise. However, by setting the threshold maximum value at 0.5, substantially all of the noise is removed, thereby producing a substantially clean image of the two vertical lines as illustrated in FIG. 39B.

From the experimental results illustrated in FIGS. 26 through 39B, the pulse compression techniques of SP3, SP4, SP5, SP6, and SP8 detect location of the two moving targets and can isolate the two targets substantially better than the LFM, NLFM, Barker, and PRN pulse compression techniques. Further, SP1 and SP2 perform marginally better than these traditional pulse compression techniques, while SP7 appears not to be able to resolve both moving targets but appears only to be able to identify one of the moving targets after reducing the noise.

Figure 40:
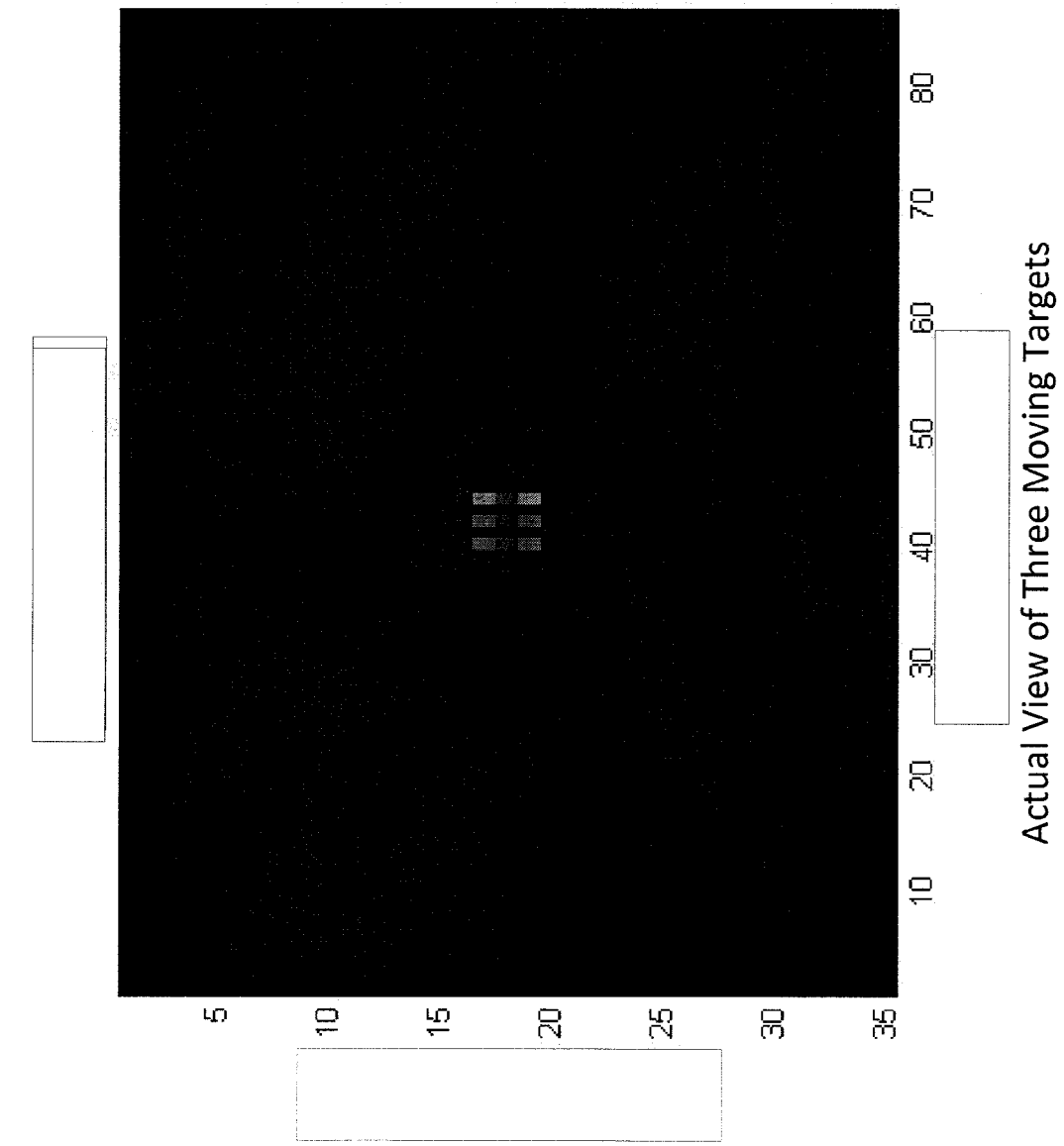
FIG. 40 is an embodiment of a schematic diagram illustrating an original view of three moving targets.

Performance of Structured Randomly Permutated Pulse Compression Generating Systems—Three In another experiment, three moving targets were analyzed. The three moving targets can be spaced apart 1% of the pulse width at 700 miles per hour in the presence of three decibel of noise. FIG. 40 illustrates an actual view of these three moving targets. As shown in FIG. 40, three vertical lines are present in the center of the screen, depicting the location of distance of separation between the three moving objects.

FIGS. 41A through 45B represent the cross ambiguities of an uncompressed and/or compressed radio signal by one or more existing pulse compression techniques.

Figure 41B:
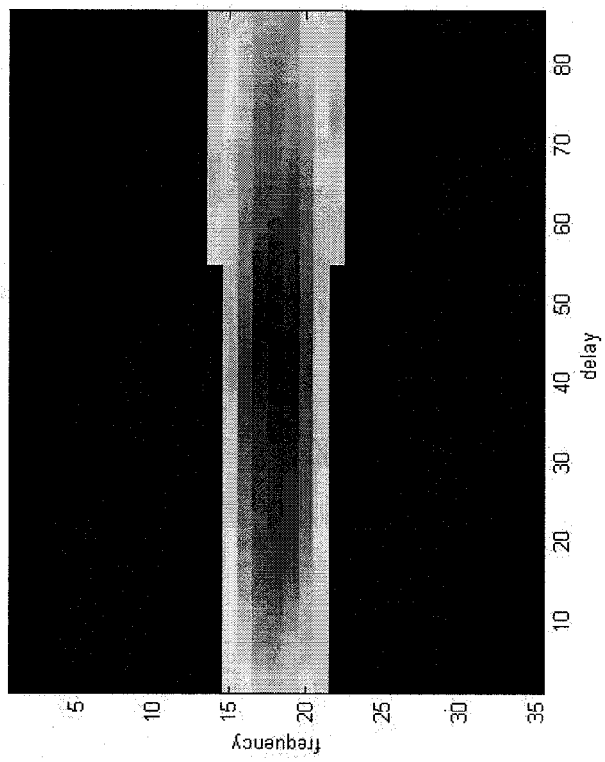
FIGS. 41A and 41B are embodiments of schematic diagrams illustrating images, generated by a rectangular pulse signal, of the three moving targets.
Figure 41A:
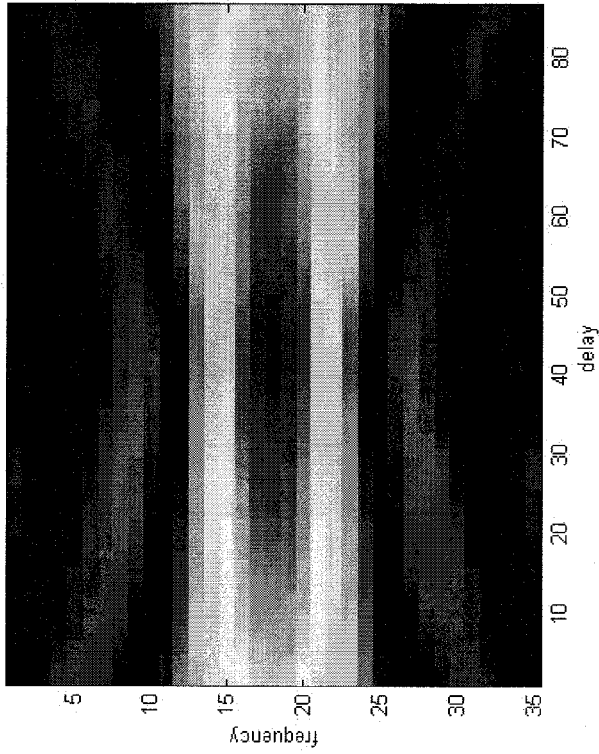

More specifically, FIGS. 41A and 41B illustrate the cross ambiguity of a rectangular pulse. As shown in FIG. 41A, the cross ambiguity of a rectangular pulse of three moving objects presents a substantial amount of noise and a smeared image of the three vertical lines. Even after setting the threshold maximum value at 0.5, although some of the noise is removed, the three vertical lines are still smeared as shown in FIG. 41B thereby making it difficult if not impossible to ascertain the location of the three moving objects and/or isolate one from another.

Figure 42A:
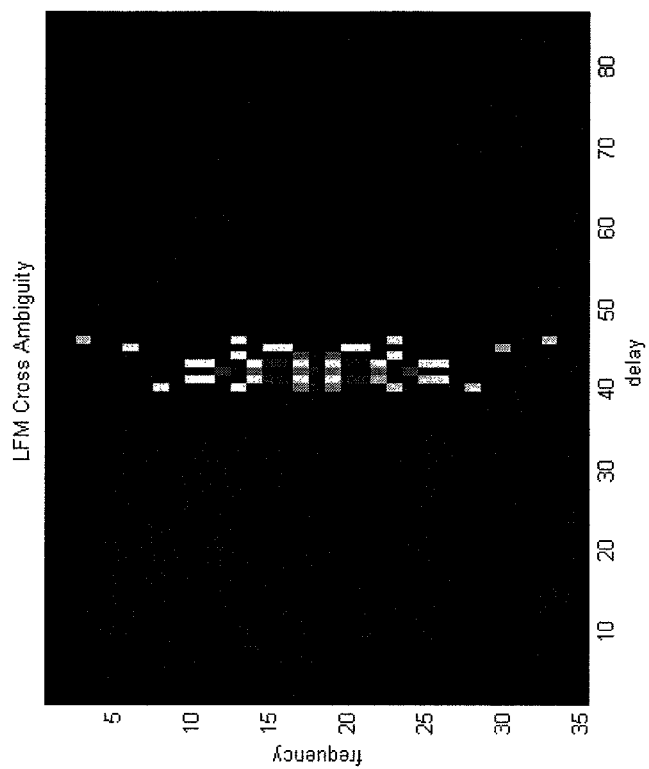
FIGS. 42A and 42B are embodiments of schematic diagrams illustrating images, generated by a LFM pulse signal, of the three moving targets.
Figure 42B:
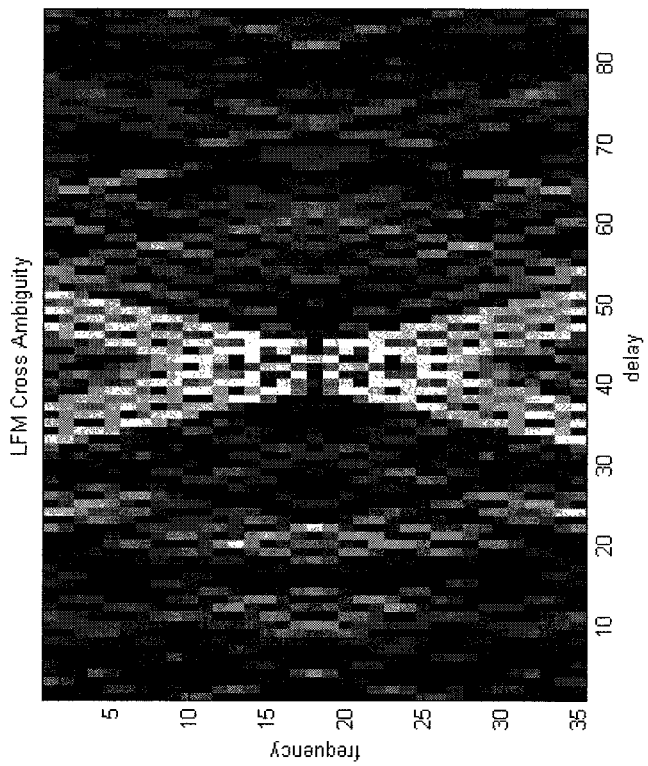

FIGS. 42A and 42B illustrate the cross ambiguity of an LFM pulse. As shown in FIG. 42A, the cross ambiguity of an LFM pulse generates a substantial amount of noise. Even after setting the threshold value at a maximum of 0.5, a substantial amount of noise is still present as shown in FIG. 42B. Again, it is difficult if not impossible to ascertain the location of the three moving objects and/or isolate one from another.

Figure 43B:
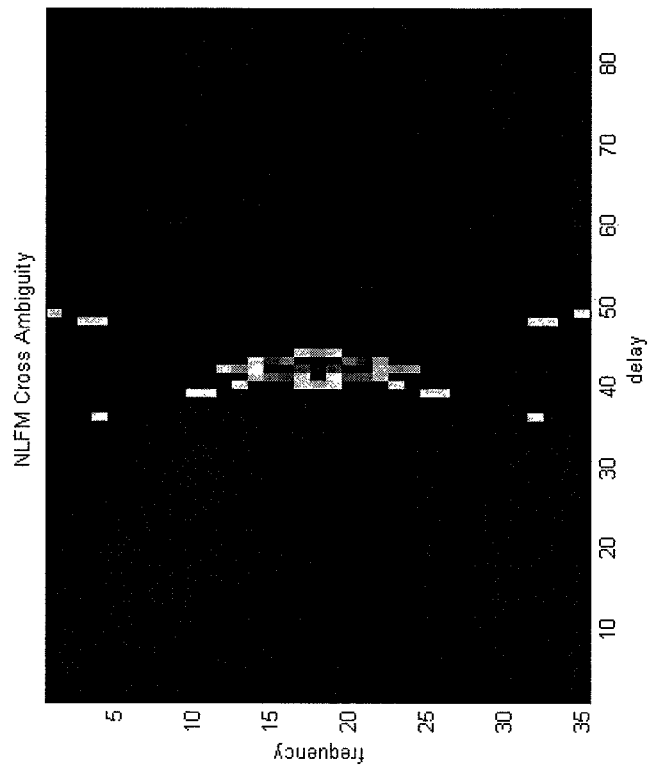
FIGS. 43A and 43B are embodiments of schematic diagrams illustrating images, generated by a NLFM pulse signal, of the three moving targets.
Figure 43A:
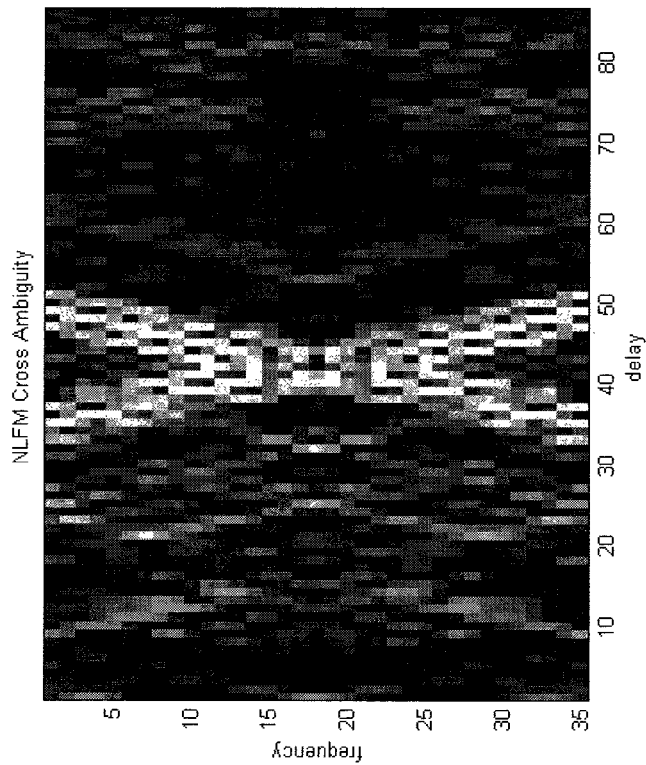

FIGS. 43A and 43B illustrate the cross ambiguity of an NLFM pulse. As shown in FIG. 43A, the cross ambiguity of an NLFM pulse of the three moving objects results in a substantial amount of noise. Even after setting the threshold maximum value at 0.5, a substantial amount of noise is still present as shown in FIG. 43B.

Figure 44B:
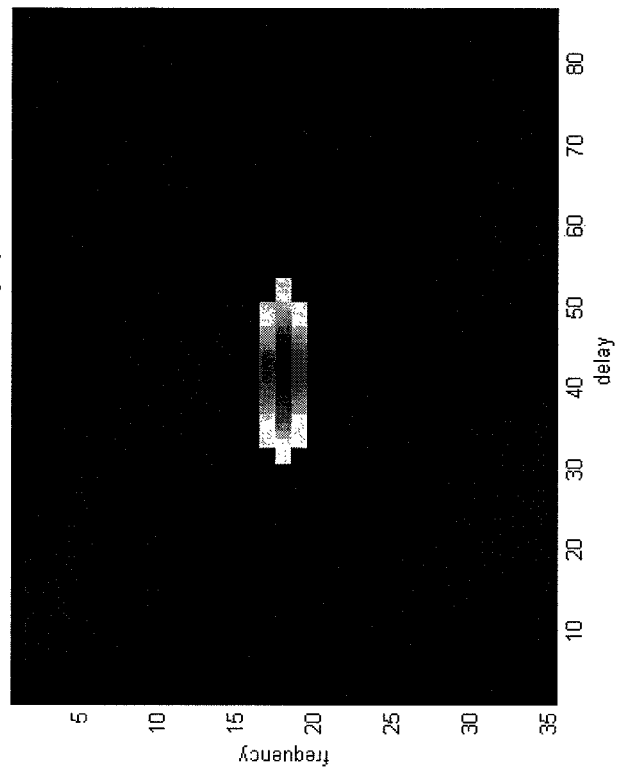
FIGS. 44A and 44B are embodiments of schematic diagrams illustrating images, generated by a Barker pulse signal, of the three moving targets.
Figure 44A:
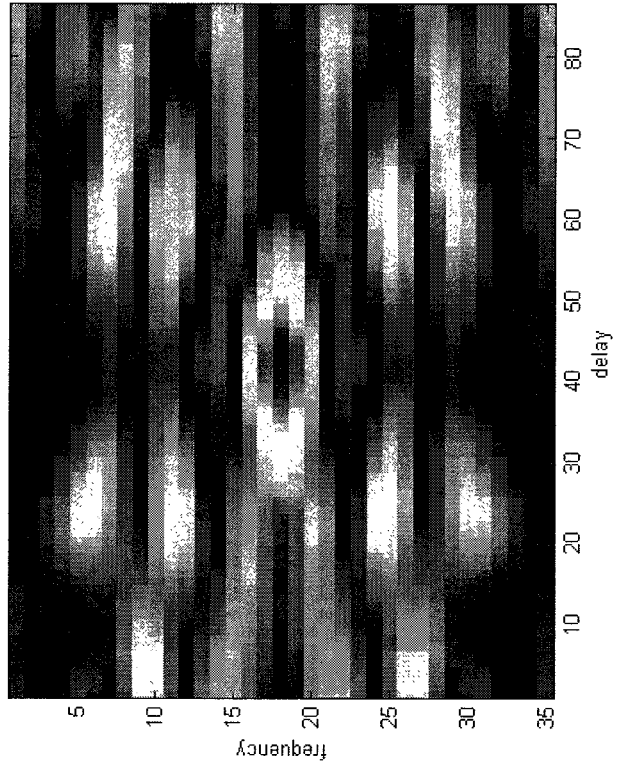

FIGS. 44A and 44B illustrate the cross ambiguity of a Barker pulse. As shown in FIG. 44A, a substantial amount of noise is present in the cross ambiguity of a Barker pulse. Also, the three vertical lines are substantially smeared. Even after setting the threshold maximum value at 0.5, the three vertical lines still appear smeared as shown in FIG. 44B.

Figure 45B:
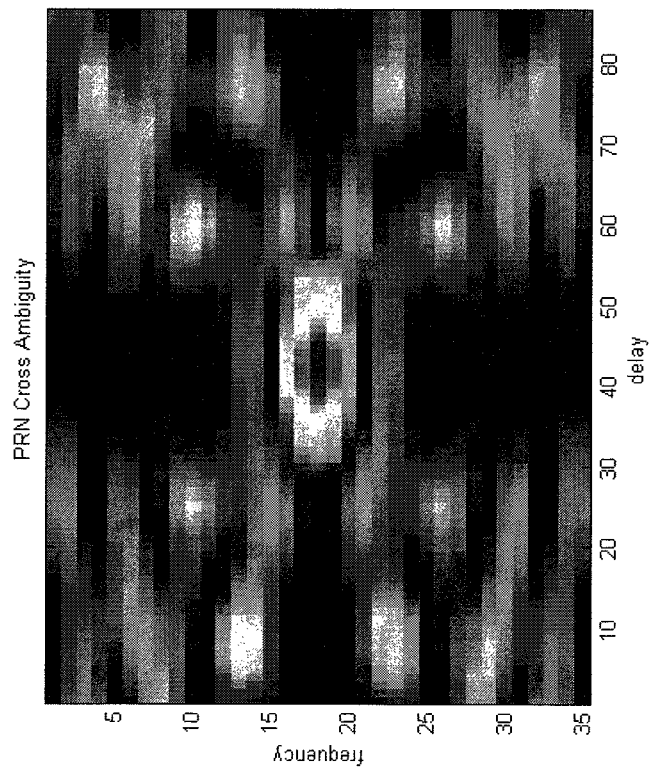
FIGS. 45A and 45B are embodiments of schematic diagrams illustrating images, generated by a PRN pulse signal, of the three moving targets.
Figure 45A:
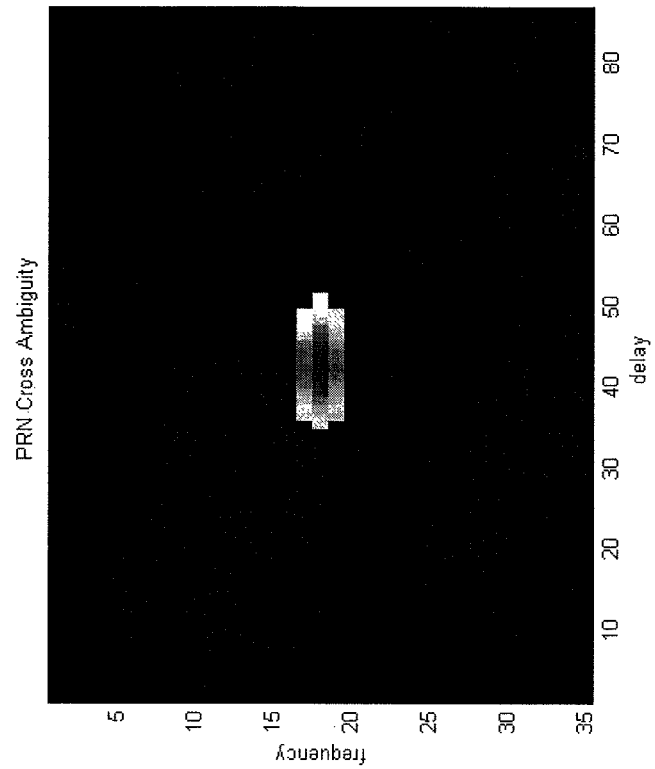

FIGS. 45A and 45B illustrate the cross ambiguity of a PRN pulse. Similarly, as shown in FIG. 45A, a cross ambiguity of a PRN pulse results in a substantial amount of noise and the three vertical lines being smeared. Even after setting the threshold maximum value at 0.5, the three vertical lines still appeared smeared as shown in FIG. 45B.

FIGS. 46A through 53B illustrate the effects of applying the structured random permutation technique to an uncompressed radio signal and/or a radio signal that has already been compressed by one or more existing pulse compression methods.

Figure 46B:
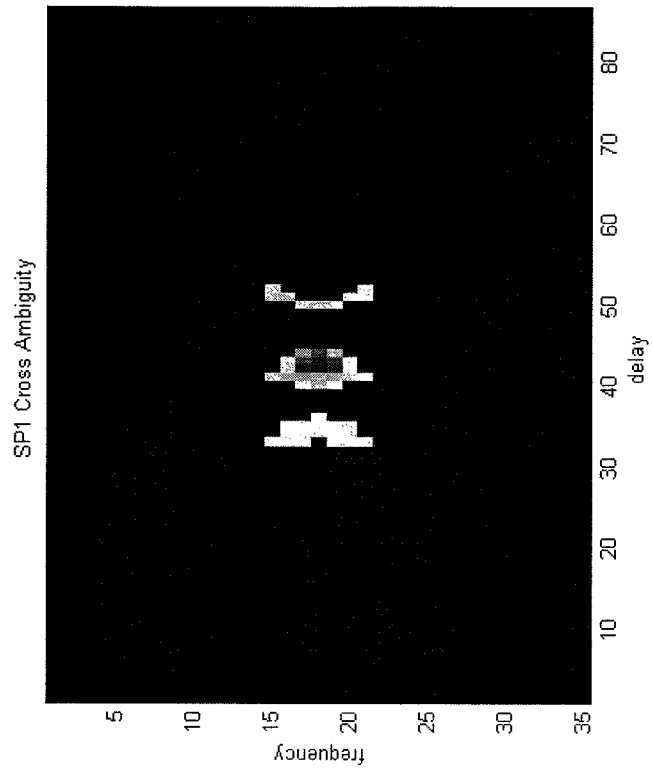
FIGS. 46A and 46B are embodiments of schematic diagrams illustrating images, generated by a chirp signal that increases as a logarithmic function of the frequency of the time samples in the input signal, of the three moving targets.
Figure 46A:
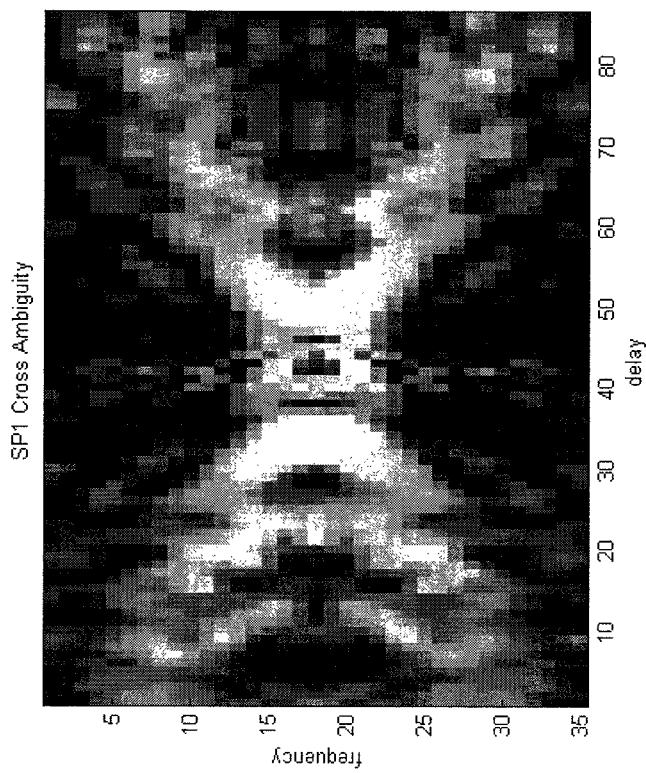

FIGS. 46A and 46B illustrate a cross ambiguity of an SP1 pulse as defined above. As shown in FIG. 46A, a cross ambiguity of an SP1 pulse results in a substantial amount of noise and some degree of smearing of the three vertical lines. However, by setting the threshold maximum value at 0.5, substantially all of the noise can be removed as illustrated in FIG. 46B. Further, although not completely vertical, the three vertical lines can still be separated by the human eye as further illustrated in FIG. 46B.

Figure 47B:
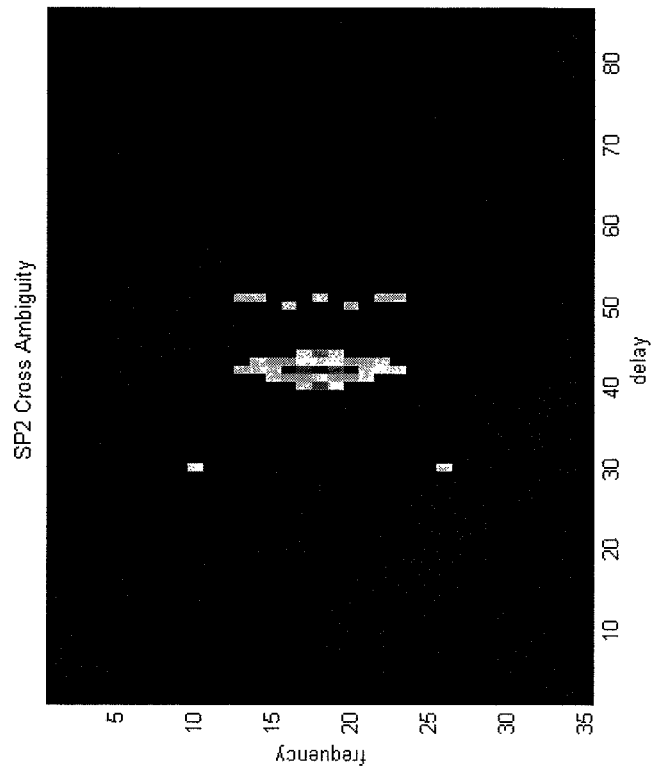
FIGS. 47A and 47B are embodiments of schematic diagrams illustrating images, generated by a chirp signal that is inversely proportional to the frequency of the time samples in the input signal, of the three moving targets.
Figure 47A:
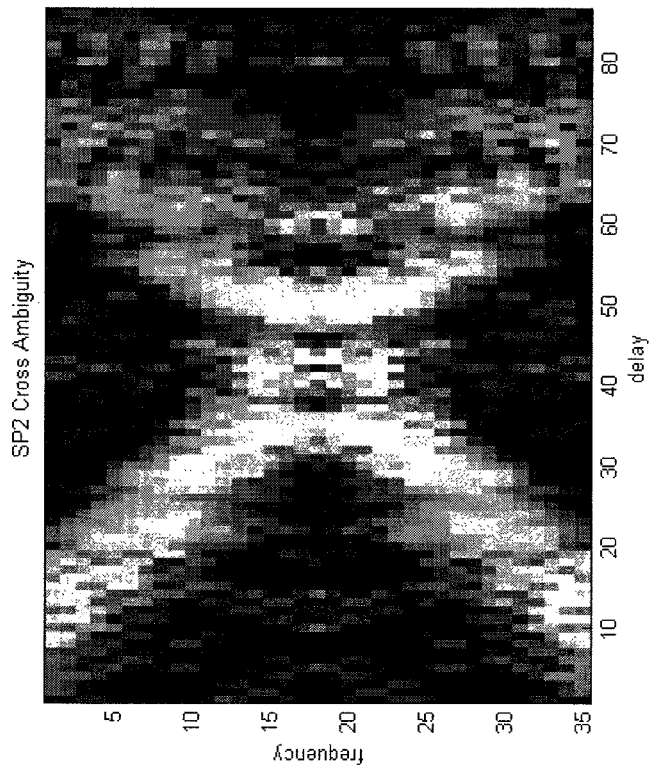

FIGS. 47A and 47B illustrate the cross ambiguity of an SP2 pulse as defined above. As shown in FIG. 47A, the cross ambiguity of an SP2 pulse of three moving objects comprises a substantial amount of noise and some smearing of the three vertical lines. However, by setting the threshold maximum value at 0.5, a substantial amount of the noise can be removed as shown in FIG. 47B. Further, although the three vertical lines are not completely vertical, it is still possible to ascertain the three moving objects depicted by the three vertical lines in FIG. 47B.

Figure 48B:
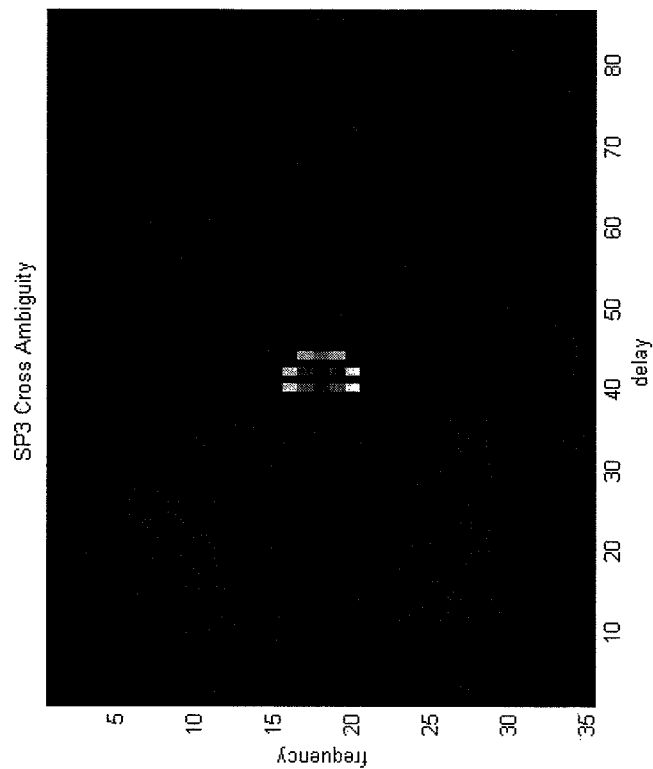
FIGS. 48A and 48B are embodiments of schematic diagrams illustrating images, generated from a chirp signal produced by a random permutation of the input signal, of the three moving targets.
Figure 48A:
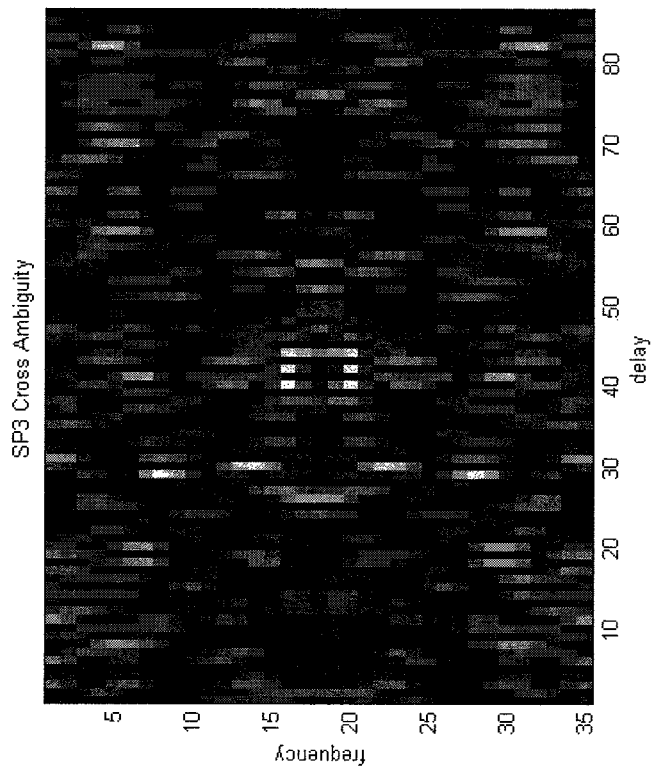

FIGS. 48A and 48B illustrate the cross ambiguity of an SP3 pulse as defined above. As shown in FIG. 48A, the cross ambiguity of an SP3 pulse results in some amount of noise. However, by setting the threshold maximum value at 0.5, substantially all of this noise can be removed thereby resulting in a substantially clean image of the three vertical lines representing the three moving objects as shown in FIG. 48B. Further, as shown in FIG. 48B, the three vertical lines in the center are substantially vertical and substantially separated from one another. Therefore, it is possible to determine the location of the three moving objects and also isolate one of them from another by simply viewing the cross ambiguity image.

Figure 49B:
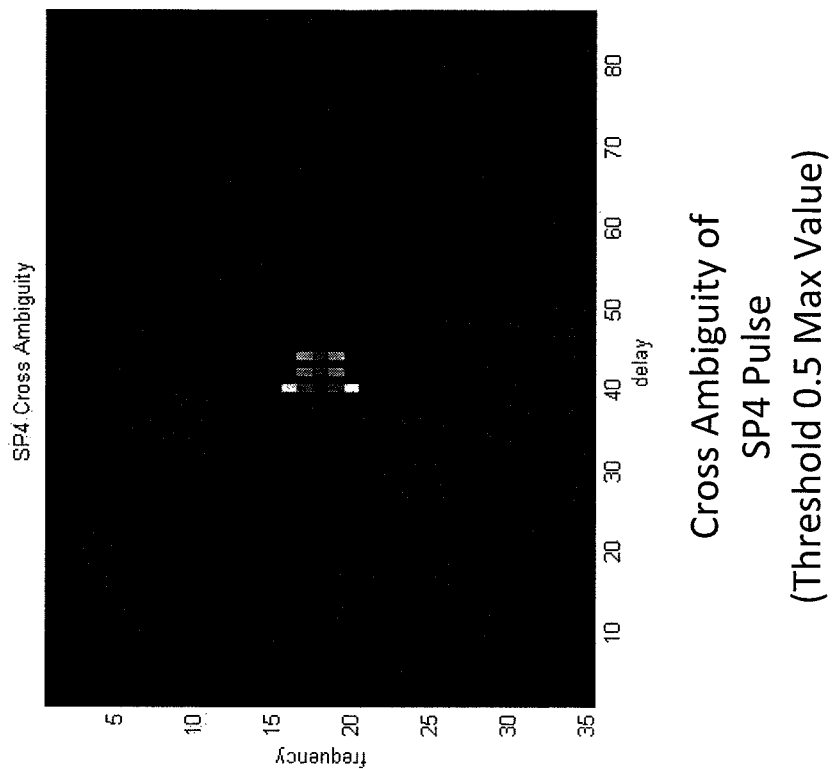
FIGS. 49A and 49B are embodiments of schematic diagrams illustrating images, generated by a structured randomly permutated LFM pulse signal, of the three moving targets.
Figure 49A:
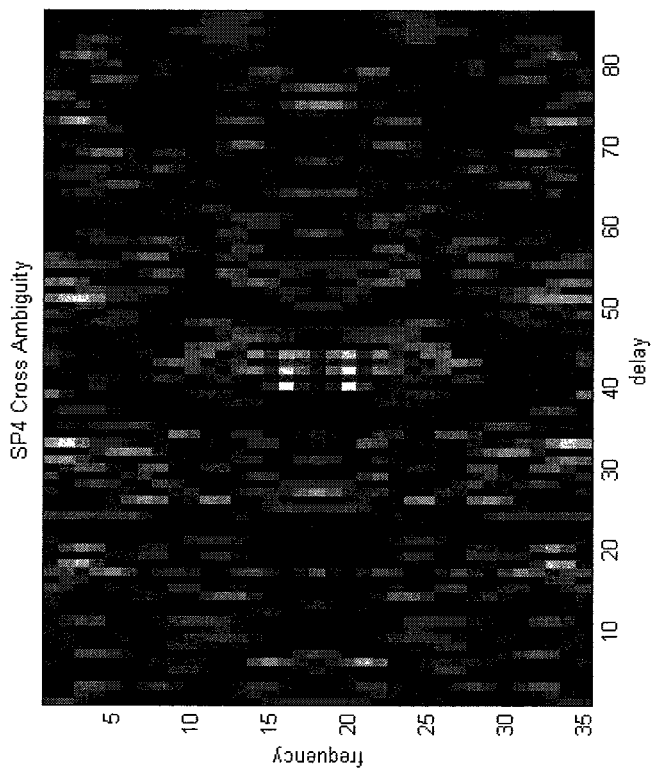

FIGS. 49A and 49B illustrate a cross ambiguity of an SP4 pulse as defined above. As shown in FIG. 49A, a cross ambiguity of an SP4 pulse results in some amount of noise. However, by setting the threshold maximum value at 0.5, substantially all of the noise can be removed as shown in FIG. 49B. Further, as shown in FIG. 49B, the three vertical lines are substantially vertical and substantially separated from one another. Therefore, it is possible to determine the location of the three moving objects and also isolate one object from another.

Figure 50B:
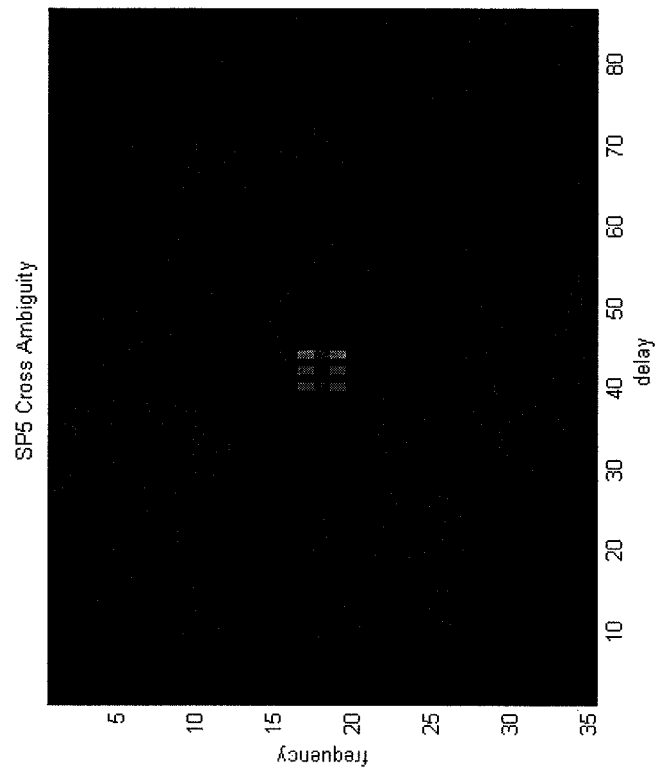
FIGS. 50A and 50B are embodiments of schematic diagrams illustrating images, generated by a structured randomly permutated rectangular pulse signal, of the three moving targets.
Figure 50A:
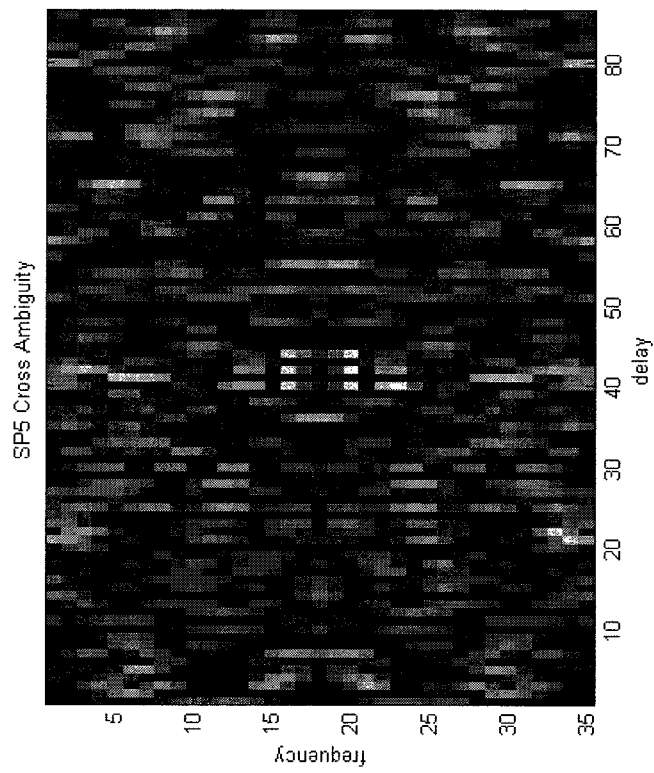

FIGS. 50A and 50B illustrate the cross ambiguity of an SP5 pulse as defined above. As shown in FIG. 50A, a cross ambiguity of an SP5 pulse results in some amount of noise. However, by setting the threshold maximum value at 0.5, substantially all of the noise can be removed as shown in FIG. 50B. Further, as shown in FIG. 50B, the three vertical lines are substantially vertical and are substantially isolated from one another. Therefore, one can very easily determine the location of the three moving objects from the three vertical lines and also isolate one object from another.

Figure 51B:
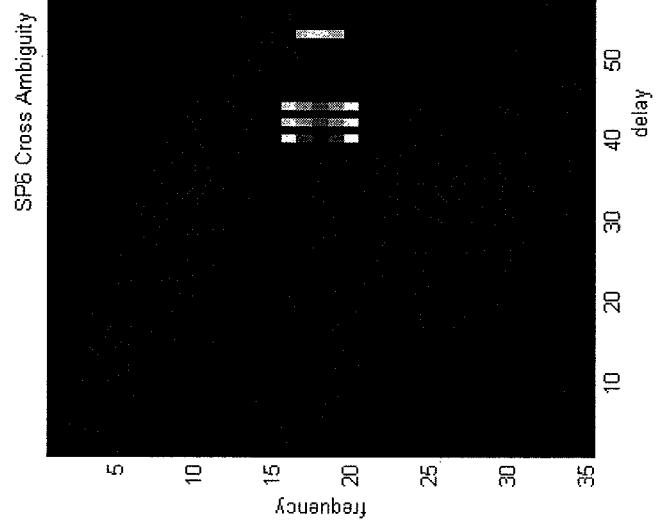
FIGS. 51A and 51B are embodiments of schematic diagrams illustrating images, generated by a structured randomly permutated Barker pulse signal, of the three moving targets.
Figure 51A:
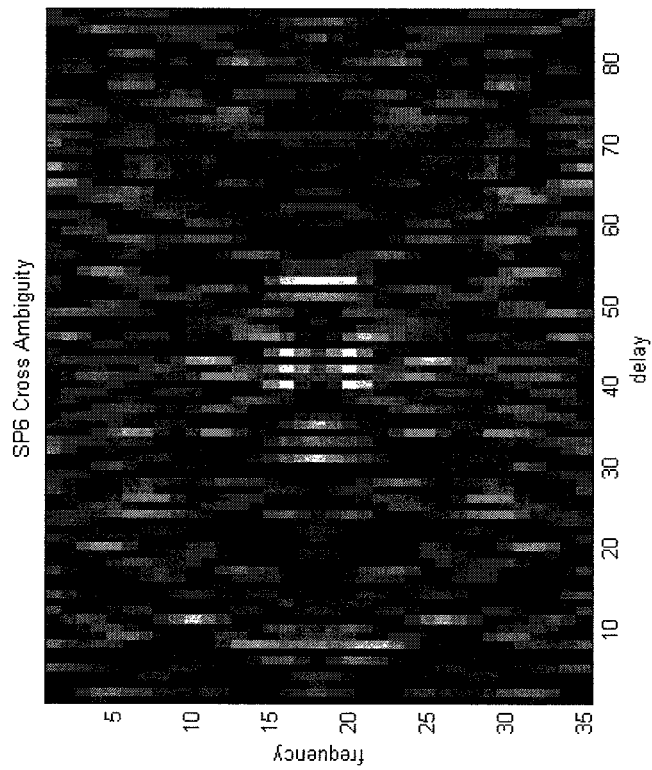

FIGS. 51A and 51B illustrate a cross-ambiguity of an SP6 pulse as defined above. As shown in FIG. 51A, a cross ambiguity of an SP6 pulse results in some amount of noise. However, by setting the threshold maximum value at 0.5, substantially all of the noise can be removed as shown in FIG. 51B. Further, as shown in FIG. 51B, the three vertical lines are substantially vertical and are separated from one another. However, a fourth vertical line is present in FIG. 51B to the right of the three vertical lines which can potentially create some confusion to a user.

Figure 52B:
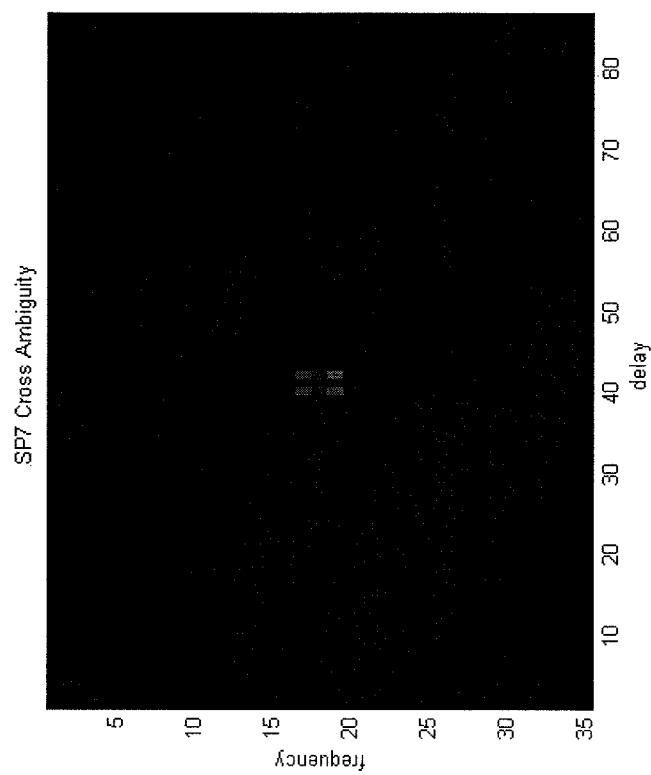
FIGS. 52A and 52B are embodiments of schematic diagrams illustrating images, generated by a structured randomly permutated PRN pulse signal, of the three moving targets.
Figure 52A:
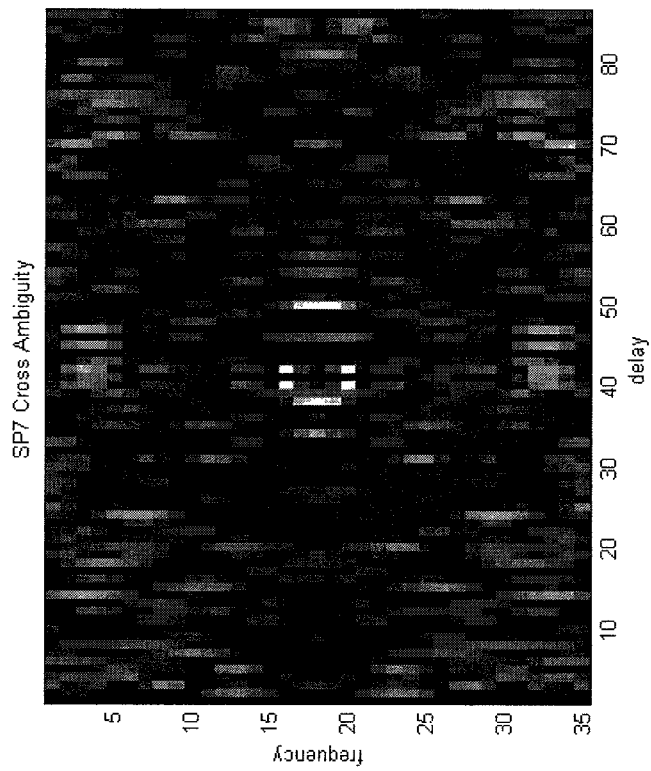

FIGS. 52A and 52B illustrate a cross ambiguity image of an SP7 pulse as defined above. As shown in FIG. 52A, some amount of noise is present in the cross ambiguity of an SP7 pulse. However, by setting the threshold maximum value at 0.5, substantially all of the noise can be removed as shown in FIG. 52B. Further, although not all three vertical lines are clearly represented, at least two vertical lines are clearly present in FIG. 52B and are also substantially separated from one another.

Figure 53B:
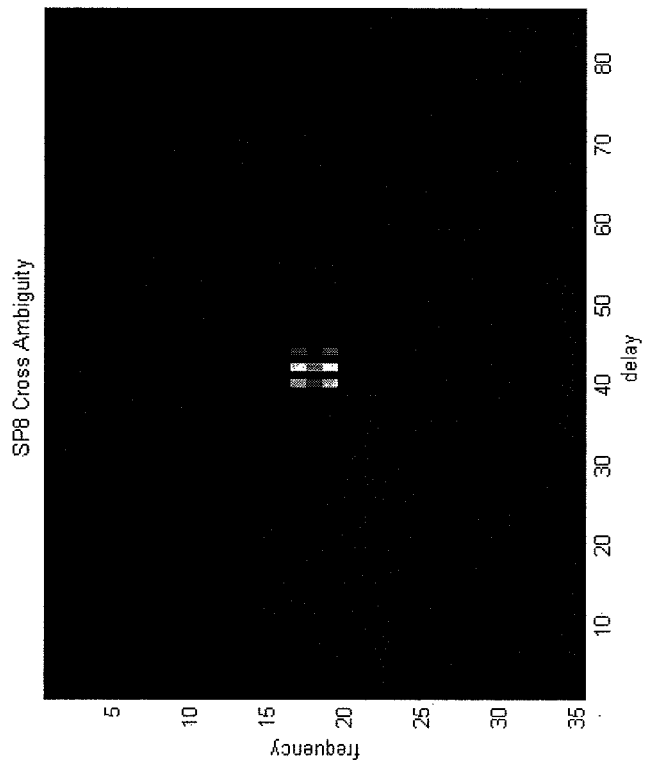
FIGS. 53A and 53B are embodiments of schematic diagrams illustrating images, generated by a structured randomly permutated NLFM pulse signal, of the three moving targets.
Figure 53A:
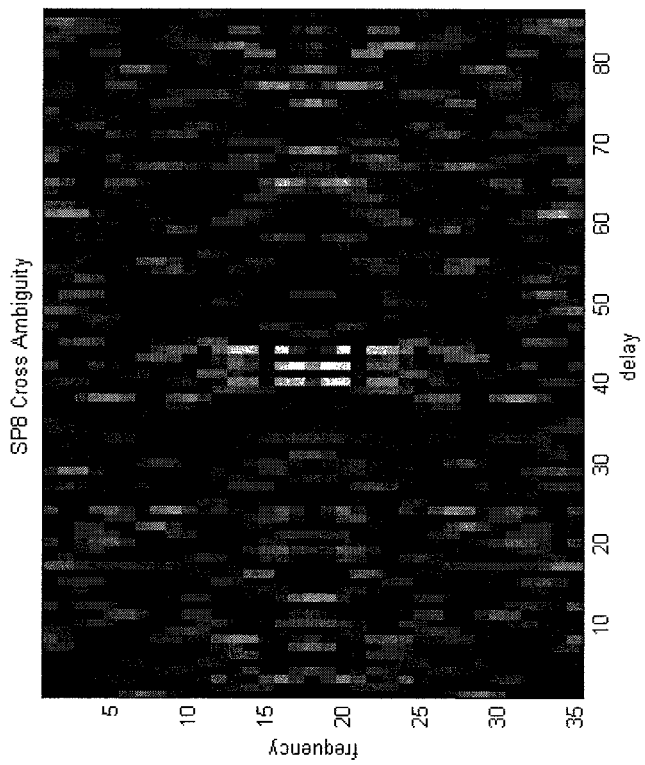

FIGS. 53A and 53B illustrate a cross ambiguity of an SP8 pulse as defined above. As shown in FIG. 53A, a cross ambiguity of an SP8 pulse results in some amount of noise. However, this noise can be substantially removed by setting the threshold maximum value at 0.5 as shown in FIG. 53B. Further, as shown in FIG. 53B, the three vertical lines are substantially vertical and are separated from one another. Accordingly, a user can easily determine the location of the three moving objects and also isolate one from another.

From the results illustrated in FIGS. 40 through 53B, the pulse compression techniques of SP3, SP4, SP5, SP6, and SP8 detect location of the three moving targets and can isolate the three targets substantially better than the LFM, NLFM, Barker, and PRN pulse compression techniques. Further, SP1 and SP2 perform marginally better than these traditional pulse compression techniques, while SP7 fails to resolve the three moving targets.

Figure 54:
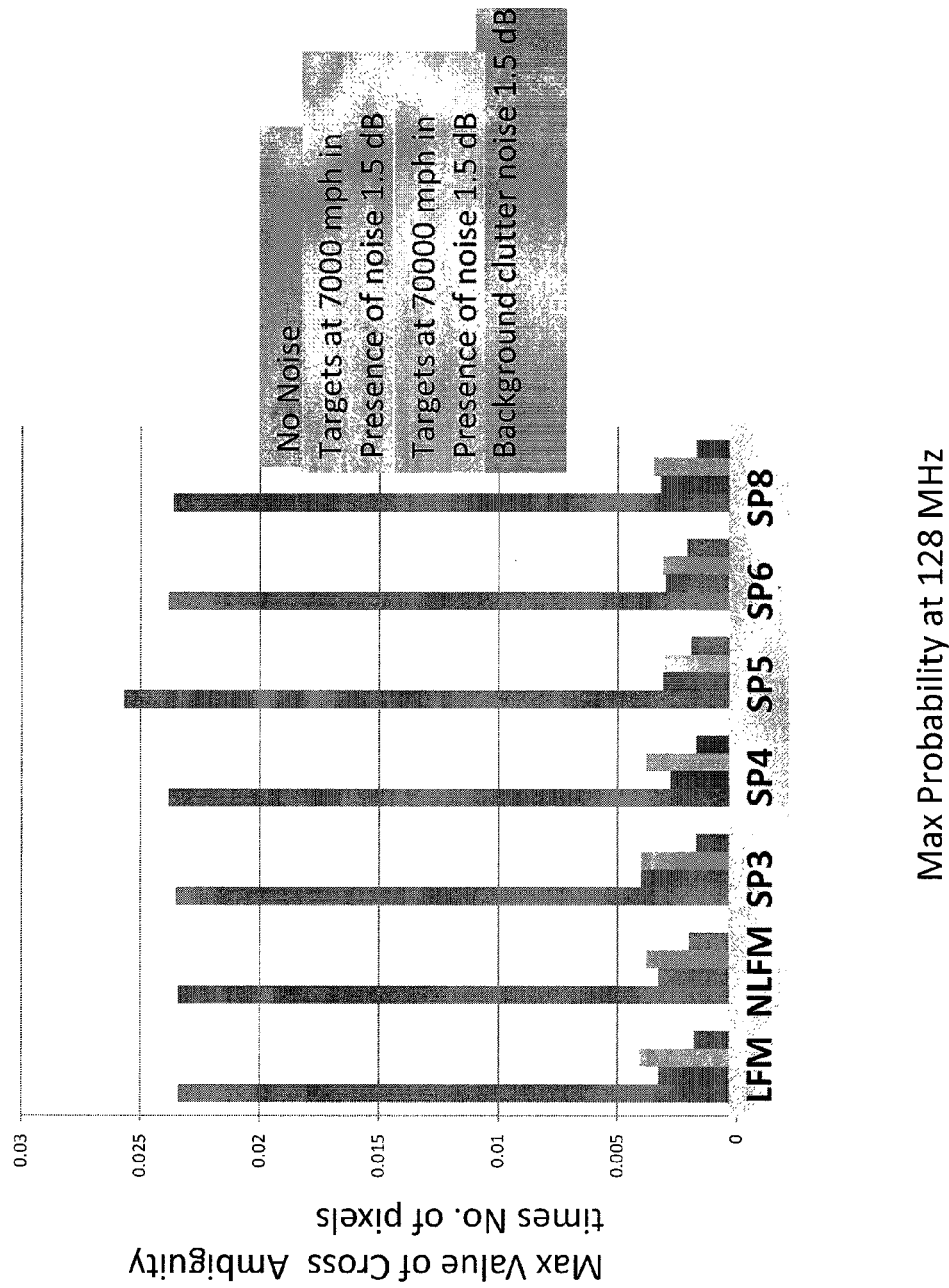
FIG. 54 is an embodiment of a chart illustrating the probability of detection of the target utilizing various pulse signals.

Performance of Structured Randomly Permutated Pulse Compression Generating Systems—Maximum Probability and Ratio of Maximum Value of Cross Ambiguity to Second Non-Target Maximum Peak FIG. 54 illustrates a comparison of the maximum probability parameter as defined above for LFM, NLFM, SP3, SP4, SP5, SP6 and SP8 pulse compression techniques. As illustrated, the maximum probability of pulse compression techniques SP3 through SP8, which are different types of structured randomly permutated pulse compression techniques, are similar if not higher than the maximum probability of LFM and NFLM. These maximum probabilities were taken at 128 megahertz. Accordingly, it is shown that these structured randomly permutated pulse compression techniques can at least equally effectively detect a target whether the target is moving or is stationary. Further, the maximum probability is significantly reduced in the presence of noise and when the targets are moving. Also, the maximum probability is significantly higher for targets than for background clutter modeled by correlating the radar pulse against random noise.

Figure 55:
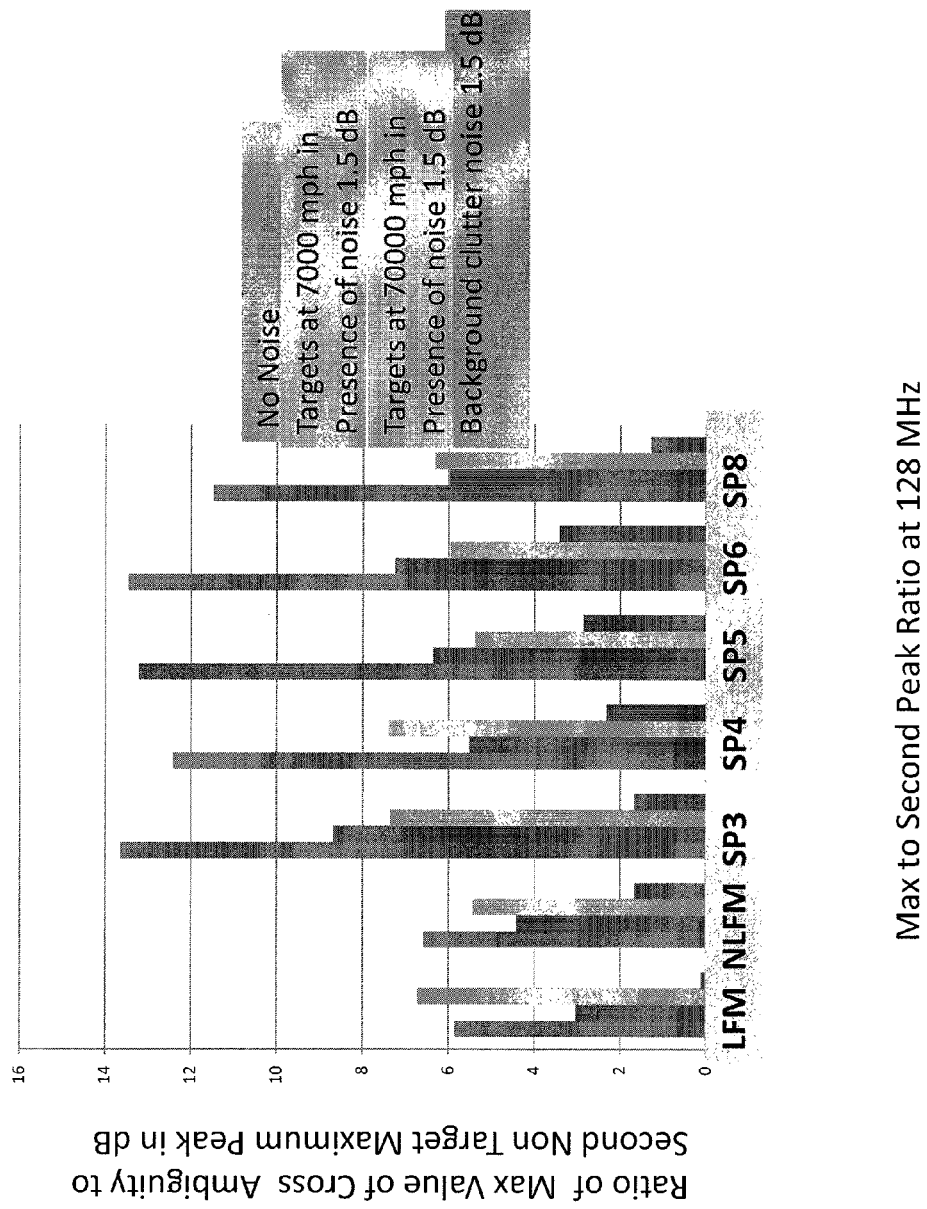
FIG. 55 is an embodiment of a chart illustrating a comparison between the detection of the target versus noise detection using various pulse signals.

FIG. 55 compares the ratio of maximum value of cross ambiguity to second non-target maximum peak in decibels as defined above among different types of pulse compression techniques. These pulse compression techniques used as points of comparison include LFM, NLFM, SP3, SP4, SP5, SP6 and SP8 as defined above. This parameter can indicate the detection of the target versus noise detection using various pulse compression techniques. Larger differences between the level of detection of the target and noise detection, or the ratio of maximum value of cross ambiguity to second non-target maximum peak, generally correspond to clearer images of one or more targets that can be produced by a particular pulse compression technique.

As illustrated in FIG. 55 the difference between the maximum value of cross ambiguity and second non-target maximum peak is substantially higher for the structured random permutation pulse compression techniques namely SP3, SP4, SP5, SP6 and SP8 compared to traditional pulse compression techniques such as LFM and NLFM. For example, the above ratio for a structured random permutation pulse compression system can be about 200% higher than that of a traditional pulse compression technique. Further, this parameter is significantly reduced in the presence of noise and when the targets are moving.

Figure 56:
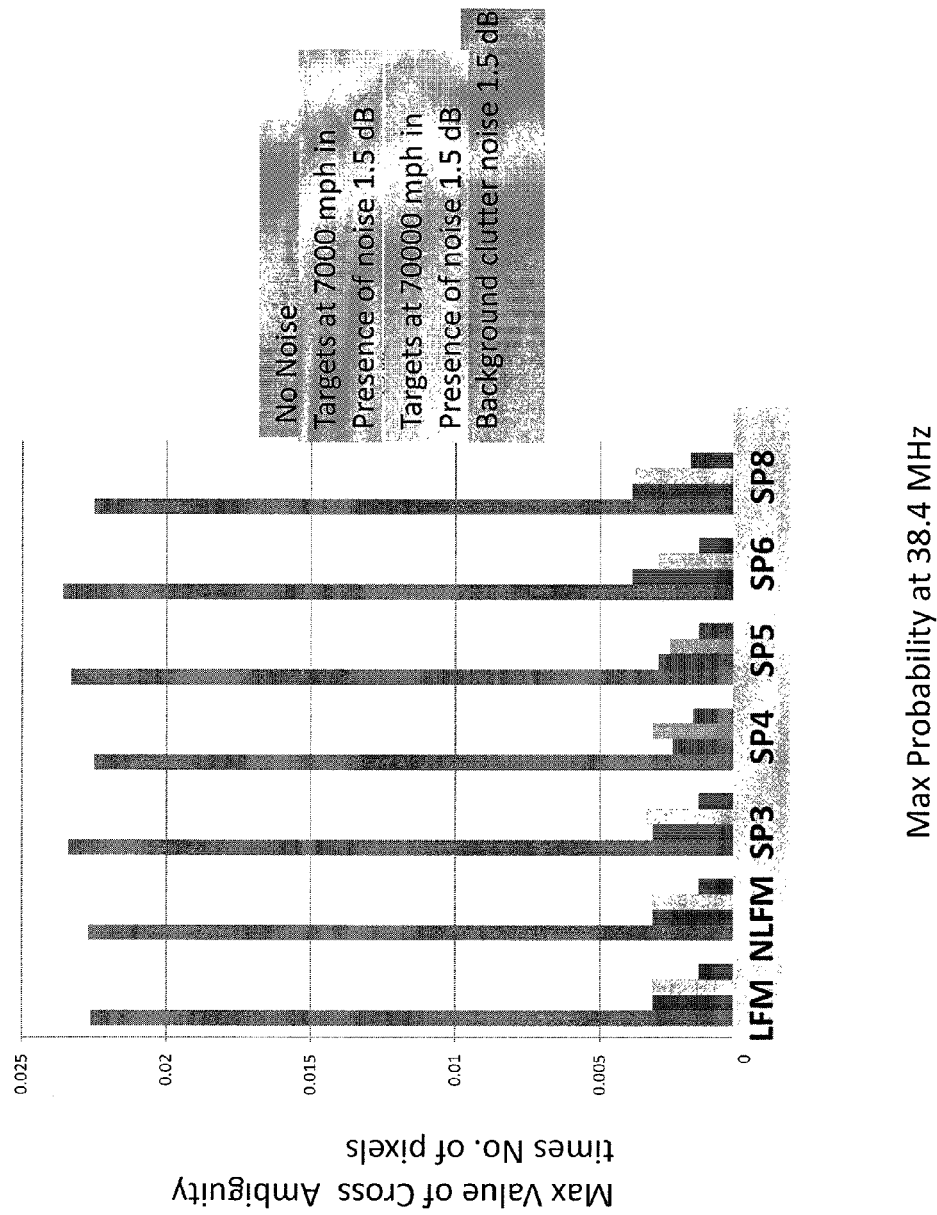
FIG. 56 is an embodiment of a chart illustrating the probability of detection of the target using various pulse signals.

FIG. 56 illustrates another comparison of maximum value of cross ambiguity as defined above among different pulse compression techniques. However in FIG. 56 the maximum probability is taken at 38.4 megahertz. Again as shown in FIG. 56 the maximum value of cross ambiguity is higher if not similar and/or equal for the structured random permutation techniques SP3, SP4, SP5, SP6 and SP8 when compared to traditional pulse compression techniques such as LFM and NLFM.

Figure 57:
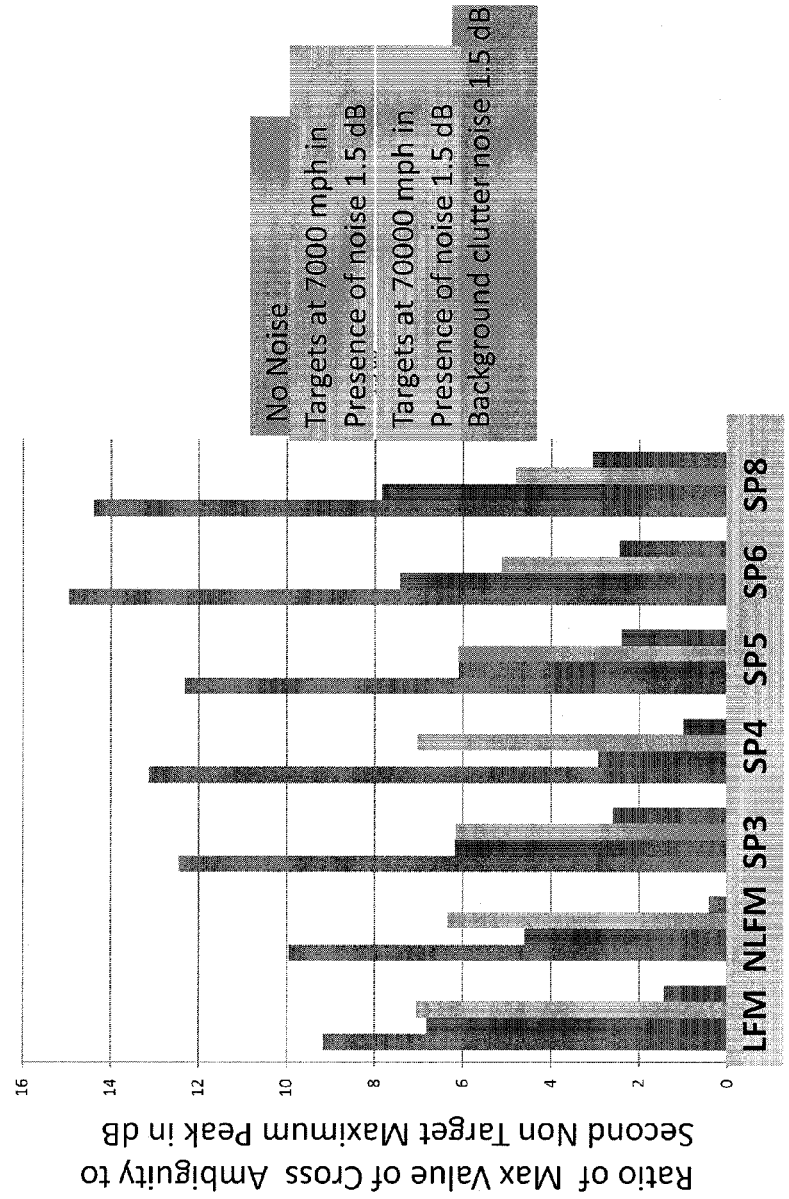
FIG. 57 is an embodiment of a chart illustrating a comparison of detecting the target versus noise detection using various pulse signals.

FIG. 57 illustrates a comparison of the ratio of maximum value of cross ambiguity to second nontarget maximum peak in decibels among traditional pulse compression techniques and structured random permutation pulse compression techniques. These maximum to second peak ratios were taken at 38.4 megahertz. As shown the ratio of maximum value of cross ambiguity to second nontarget maximum peak for the structured random permutation techniques SP3, SP4, SP5, SP6 and SP8 were substantially higher than the ratios for traditional pulse compression techniques such as LFM and NLFM. For example, the above ratio for a structured random permutation pulse compression system can be about 200% higher than that of a traditional pulse compression technique.

From the results of the experiments as illustrated in FIGS. 26 through 57 it can be seen that the structured random permutation pulse compression methods, for example SP3, SP4, SP5, SP6 and SP8, have superior range and Doppler resolution compared to traditional pulse compression methods including standard LFM and NLFM methods commonly used in RADAR applications. Also, the probability of detection for these structured random permutation pulse compression methods is significantly higher, for example five to six decibels, over LFM and NLFM compression techniques even when the targets are moving extremely fast and in the presence of significant noise.

The structured random permutation pulse compression method systems and features thereof described herein are not limited to applying such methods and systems to the pulse compression methods explicitly described herein but can further be applied to any pulse compression method that is currently known or to be developed in the future.

Further, the foregoing systems, methods, and techniques of structured random permutation pulse compression described above can be used in the context of and/or combined with radar systems, for tracking planes, automobiles, ships, and/or the like, as such radar systems and their components are described above. In addition, the foregoing systems, methods, and techniques can further be utilized and/or combined with ultrasound technology as described above. These foregoing systems, methods, and techniques of structured random permutation pulse compression can also be used for missile defense, imaging cells and/or other biological samples, and/or detection of underwater objects, for example via SONAR.

Computing System

Figure 58:
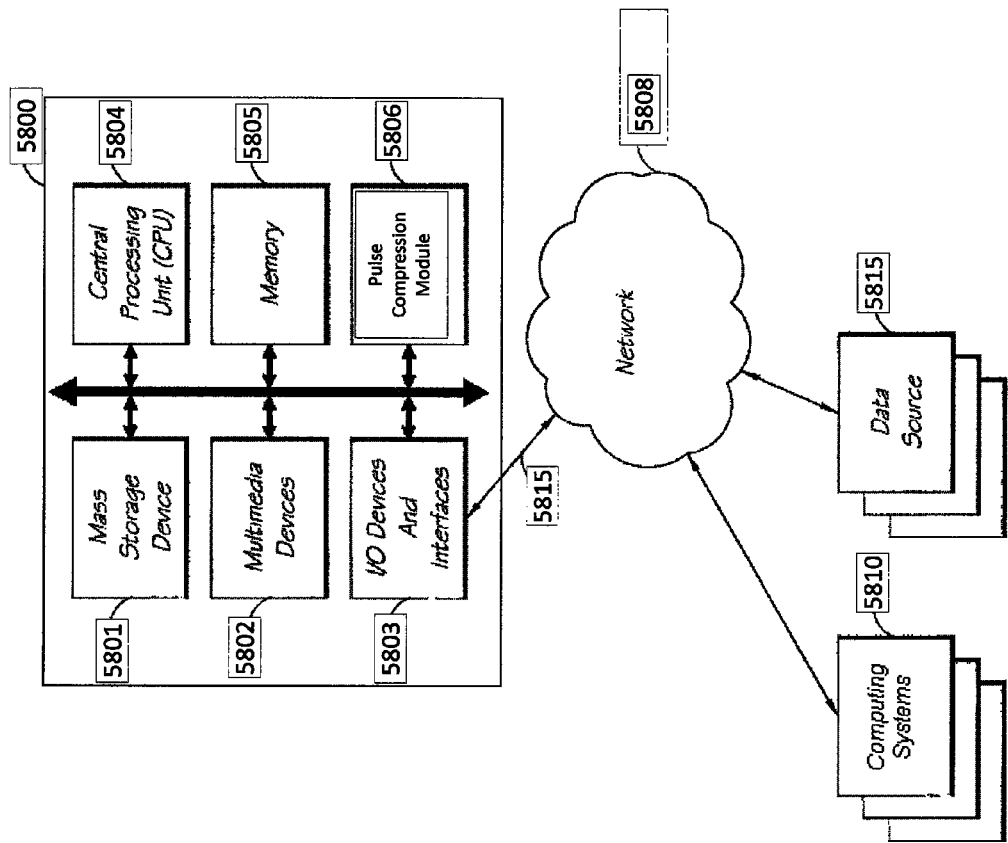
FIG. 58 is a block diagram depicting one embodiment of a computer hardware system configured to run software for implementing one or more embodiments of the pulse compression systems described herein.

In some embodiments, the computer clients and/or servers described above take the form of a computing system 5800 illustrated in FIG. 58, which is a block diagram of one embodiment of a computing system that is in communication with one or more computing systems 5810 and/or one or more data sources 5815 via one or more networks 5808. The computing system 5800 may be used to implement one or more of the systems and methods described herein. In addition, in one embodiment, the computing system 5800 may be configured to apply one or more of the structured random permutation pulse compression techniques described herein. While FIG. 58 illustrates one embodiment of a computing system 5800, it is recognized that the functionality provided for in the components and modules of computing system 5800 may be combined into fewer components and modules or further separated into additional components and modules.

Pulse Compression Module

In one embodiment, the system 5800 comprises a pulse compression module 5806 that carries out the functions described herein with reference to modulating a RADAR signal, including any one of the structured random permutation techniques described above. The pulse compression module 5806 may be executed on the computing system 5800 by a central processing unit 5804 discussed further below.

In general, the word "module," as used herein, refers to logic embodied in hardware or firmware, or to a collection of software instructions, possibly having entry and exit points, written in a programming language, such as, for example, COBOL, CICS, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

Computing System Components

In one embodiment, the computing system 5800 also comprises a mainframe computer suitable for controlling and/or communicating with large databases, performing high volume transaction processing, and generating reports from large databases. The computing system 5800 also comprises a central processing unit ("CPU") 5804, which may comprise a conventional microprocessor. The computing system 5800 further comprises a memory 5805, such as random access memory ("RAM") for temporary storage of information and/or a read only memory ("ROM") for permanent storage of information, and a mass storage device 5801, such as a hard drive, diskette, or optical media storage device. Typically, the modules of the computing system 5800 are connected to the computer using a standards based bus system. In different embodiments, the standards based bus system could be Peripheral Component Interconnect (PCI), Microchannel, SCSI, Industrial Standard Architecture (ISA) and Extended ISA (EISA) architectures, for example.

The computing system 5800 comprises one or more commonly available input/output (I/O) devices and interfaces 5803, such as a keyboard, mouse, touchpad, and printer. In one embodiment, the I/O devices and interfaces 5803 comprise one or more display devices, such as a monitor, that allows the visual presentation of data to a user. More particularly, a display device provides for the presentation of GUIs, application software data, and multimedia presentations, for example. In the embodiment of FIG. 58, the I/O devices and interfaces 5803 also provide a communications interface to various external devices. The computing system 5800 may also comprise one or more multimedia devices 5802, such as speakers, video cards, graphics accelerators, and microphones, for example.

Computing System Device/Operating System

The computing system 5800 may run on a variety of computing devices, such as, for example, a server, a Windows server, a Structure Query Language server, a Unix server, a personal computer, a mainframe computer, a laptop computer, a cell phone, a personal digital assistant, a kiosk, an audio player, and so forth. The computing system 5800 is generally controlled and coordinated by operating system software, such as z/OS, Windows 95, Windows 98, Windows NT, Windows 2000, Windows XP, Windows Vista, Windows 7, Linux, BSD, SunOS, Solaris, or other compatible operating systems. In Macintosh systems, the operating system may be any available operating system, such as MAC OS X. In other embodiments, the computing system 5800 may be controlled by a proprietary operating system. Conventional operating systems control and schedule computer processes for execution, perform memory management, provide file system, networking, and I/O services, and provide a user interface, such as a graphical user interface ("GUI"), among other things.

Network

In the embodiment of FIG. 58, the computing system 5800 is coupled to a network 5808, such as a LAN, WAN, or the Internet, for example, via a wired, wireless, or combination of wired and wireless, communication link 5815. The network 5808 communicates with various computing devices and/or other electronic devices via wired or wireless communication links. In the embodiment of FIG. 58, the network 5808 is communicating with one or more computing systems 5810 and/or one or more data sources 5815.

Access to the pulse compression module 5806 of the computer system 5800 by computing systems 5810 and/or by data sources 5815 may be through a web-enabled user access point such as the computing systems' 5810 or data source's 5815 personal computer, cellular phone, laptop, or other device capable of connecting to the network 5808. Such a device may have a browser module is implemented as a module that uses text, graphics, audio, video, and other media to present data and to allow interaction with data via the network 5808.

The browser module may be implemented as a combination of an all points addressable display such as a cathode-ray tube (CRT), a liquid crystal display (LCD), a plasma display, or other types and/or combinations of displays. In addition, the browser module may be implemented to communicate with input devices 5803 and may also comprise software with the appropriate interfaces which allow a user to access data through the use of stylized screen elements such as, for example, menus, windows, dialog boxes, toolbars, and controls (for example, radio buttons, check boxes, sliding scales, and so forth). Furthermore, the browser module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 5800 may comprise a physical or logical connection established between a remote microprocessor and a mainframe host computer for the express purpose of uploading, downloading, or viewing interactive data and databases on-line in real time. The remote microprocessor may be operated by an entity operating the computer system 5800, including the client server systems or the main server system, an/or may be operated by one or more of the data sources 5815 and/or one or more of the computing systems. In some embodiments, terminal emulation software may be used on the microprocessor for participating in the micro-mainframe link.

In some embodiments, computing systems 5810 who are internal to an entity operating the computer system 5800 may access the pulse compression module 5806 internally as an application or process run by the CPU 5804.

User Access Point

In an embodiment, a user access point or user interface 5806 comprises a personal computer, a laptop computer, a cellular phone, a GPS system, a Blackberry® device, a portable computing device, a server, a computer workstation, a local area network of individual computers, an interactive kiosk, a personal digital assistant, an interactive wireless communications device, a handheld computer, an embedded computing device, or the like.

Other Systems

In addition to the systems that are illustrated in FIG. 58, the network 5808 may communicate with other data sources or other computing devices. The computing system 5800 may also comprise one or more internal and/or external data sources. In some embodiments, one or more of the data repositories and the data sources may be implemented using a relational database, such as DB2, Sybase, Oracle, CodeBase and Microsoft® SQL Server as well as other types of databases such as, for example, a signal database, an object-oriented database, and/or a record-based database.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. For all of the embodiments described herein the steps of the methods need not be performed sequentially. Thus, it is intended that the scope of the present invention herein disclosed should not be limited by the particular disclosed embodiments described above.

What is claimed is:

1. An ultrasound-based diagnostic medical imaging system, the system comprising:
    at least one transducer, the transducer configured to be placed near a tissue surface, the transducer comprising a piezoelectric crystal configured to produce ultrasound waves for transmission into the tissue surface and to receive ultrasound waves reflected from structures below the tissue surface;
    a modulator configured to be connected to the piezoelectric crystal, the modulator configured to generate an output signal by modulating an input signal according to a structured random permutation pulse compression sequence, the modulator further configured to transmit the output signal through the piezoelectric crystal;
    a data processing controller configured to be connected to the transducer, the data processing controller configured to receive the reflected ultrasound waves through the transducer, the data processing controller further configured to correlate the reflected ultrasound waves with the produced ultrasound waves; and
    an image generator configured to generate an image based on the correlation of the reflected sound waves with the produced ultrasound waves.

2. The ultrasound-based diagnostic medical imaging system of claim 1, wherein the input signal is a linear frequency modulation signal.

3. The ultrasound-based diagnostic medical imaging system of claim 1, wherein the input signal is a rectangular pulse.

4. The ultrasound-based diagnostic medical imaging system of claim 1, wherein the input signal is a barker code modulating a rectangular pulse.

5. The ultrasound-based diagnostic medical imaging system of claim 1, wherein the input signal is a pseudo random number code modulating a rectangular pulse.

6. The ultrasound-based diagnostic medical imaging system of claim 1, wherein the input signal is a non-linear frequency modulation signal.

7. The ultrasound-based diagnostic medical imaging system of claim 1, wherein the data processing controller is further configured to exclude values of the reflected ultrasound waves above a threshold value prior to correlating the reflected ultrasound waves with the produced ultrasound waves.

8. An ultrasound-based diagnostic medical imaging system, the system comprising:
    at least one transducer configured to be placed proximate a tissue surface, the transducer comprising a piezoelectric crystal configured to produce ultrasound waves for transmission into the tissue surface and to receive ultrasound waves reflected from below the tissue surface;
    a modulator configured to connect to the piezoelectric crystal, the modulator configured to generate an output signal by modulating an input signal according to a structured random permutation pulse compression sequence, the modulator further configured to transmit the output signal through the piezoelectric crystal; and
    a data processing controller configured to communicate with the transducer, the data processing controller configured to receive the reflected ultrasound waves through the transducer, the data processing controller further configured to correlate the reflected ultrasound waves with the produced ultrasound waves and communicate the correlation with an image generator.

9. The ultrasound-based diagnostic medical imaging system of claim 8, wherein the input signal is a linear frequency modulation (LFM) signal.

10. The ultrasound-based diagnostic medical imaging system of claim 8, wherein the input signal is a rectangular pulse.

11. The ultrasound-based diagnostic medical imaging system of claim 8, wherein the input signal is a barker code modulating a rectangular pulse.

12. The ultrasound-based diagnostic medical imaging system of claim 8, wherein the input signal is a pseudo random number code modulating a rectangular pulse.

13. The ultrasound-based diagnostic medical imaging system of claim 8, wherein the input signal is a non-linear frequency modulation signal.

14. The ultrasound-based diagnostic medical imaging system of claim 8, wherein the data processing controller is further configured to exclude values of the reflected ultrasound waves above a threshold value prior to correlating the reflected ultrasound waves with the produced ultrasound waves.

15. An ultrasound-based diagnostic medical imaging system, the system comprising:
    at least one transducer, the transducer configured to be placed on a tissue surface, the transducer comprising a piezoelectric crystal configured to produce ultrasound waves for transmission into the tissue surface and to receive reflected ultrasound waves bounced off structures below the tissue surface;
    a modulator configured to be connected to the piezoelectric crystal, the modulator configured to generate an output signal by modulating an input signal according to a structured random permutation pulse compression sequence, the modulator further configured to transmit the output signal through the piezoelectric crystal;

a data processing controller configured to be connected to the transducer, the data processing controller configured to receive the reflected ultrasound waves through the transducer, the data processing controller further configured to correlate the reflected ultrasound waves with the produced ultrasound waves;

an image generator configured to generate an image based on the correlation of the reflected sound waves with the produced ultrasound waves; and a display configured to display the generated image to a user.

16. The ultrasound-based diagnostic medical imaging system of claim 15, wherein the input signal is a linear frequency modulation (LFM) signal.

17. The ultrasound-based diagnostic medical imaging system of claim 15, wherein the input signal is a rectangular pulse.

18. The ultrasound-based diagnostic medical imaging system of claim 15, wherein the input signal is a barker code modulating a rectangular pulse.

19. The ultrasound-based diagnostic medical imaging system of claim 15, wherein the input signal is a pseudo random number code modulating a rectangular pulse.

20. The ultrasound-based diagnostic medical imaging system of claim 15, wherein the input signal is a non-linear frequency modulation signal.

\* \* \* \* \*